(12) United States Patent
Song et al.

(10) Patent No.: US 9,885,018 B1
(45) Date of Patent: Feb. 6, 2018

(54) HIGH EFFICIENCY REPROGRAMMING OF FIBROBLASTS INTO CARDIOMYOCYTES

(71) Applicant: The Regents of the University of Colorado, a body corporate, Denver, CO (US)

(72) Inventors: Kunhua Song, Centennial, CO (US); Yuanbiao Zhao, Denver, CO (US); Pilar Londono, Highlands Ranch, CO (US); Timothy McKinsey, Broomfield, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 15/072,122

(22) Filed: Mar. 16, 2016

Related U.S. Application Data

(60) Provisional application No. 62/133,716, filed on Mar. 16, 2015.

(51) Int. Cl.
| | | |
|---|---|---|
| *C12N 5/077* | (2010.01) | |
| *A61K 48/00* | (2006.01) | |
| *A61K 31/713* | (2006.01) | |
| *A61K 38/17* | (2006.01) | |
| *A61K 45/06* | (2006.01) | |

(52) U.S. Cl.
CPC .......... *C12N 5/0657* (2013.01); *A61K 31/713* (2013.01); *A61K 38/1709* (2013.01); *A61K 45/06* (2013.01); *A61K 48/00* (2013.01); *C12N 2501/15* (2013.01); *C12N 2501/60* (2013.01); *C12N 2501/65* (2013.01); *C12N 2501/727* (2013.01); *C12N 2501/73* (2013.01); *C12N 2501/999* (2013.01); *C12N 2506/1307* (2013.01)

(58) Field of Classification Search
None
See application file for complete search history.

(56) References Cited

U.S. PATENT DOCUMENTS

| | | | | |
|---|---|---|---|---|
| 9,017,661 | B2* | 4/2015 | Nam ................... | C07K 14/4702 424/93.2 |
| 9,523,079 | B2* | 12/2016 | Nam ................... | C07K 14/4702 |
| 2010/0010073 | A1* | 1/2010 | Thum .................. | C12N 15/113 514/44 R |
| 2014/0011281 | A1* | 1/2014 | Dzau ................... | A61K 27/3804 435/456 |
| 2015/0290237 | A1* | 10/2015 | Liu ......................... | A61K 48/00 514/44 R |
| 2015/0297611 | A1* | 10/2015 | Dzau .............. | C12Y 201/01043 514/218 |
| 2016/0186141 | A1* | 6/2016 | Cao ...................... | A61K 31/519 424/93.7 |
| 2016/0215263 | A1* | 7/2016 | Keller .................. | C12N 5/0657 |
| 2016/0251624 | A1* | 9/2016 | Wang ................... | C12N 5/0657 |
| 2016/0362705 | A1* | 12/2016 | Abraham ............... | A61K 35/12 |

OTHER PUBLICATIONS

Nam et al., Proc Natl Acad Sci U S A. Apr. 2, 2013;110(14):5588-5593.*
Willems, E. et al. Small molecule-mediated TGF-b type II receptor degradation promotes cardiomyogenesis in embryonic stem cells. Cell Stem Cell 11,242-252 (2012).
Efe, J. A. et al. Conversion of mouse fibroblasts into cardiomyocytes using a direct reprogramming strategy. Nat. Cell Biol. 13, 215-222 (2011).
Wang, H. et al. Small molecules enable cardiac reprogramming of mouse fibroblasts with a single factor, Oct 4. Cell Rep. 6, 951-960 (2014).
Bao, W. et al. Inhibition of Rho-kinase protects the heart against ischemia/reperfusion injury. Cardiovasc. Res. 61, 548-558 (2004).
Lee, T. I. et al. Control of developmental regulators by Polycomb in human embryonic stem cells. Cell 125, 301-313 (2006).
Wu, T. D. & Nacu, S. Fast and SNP-tolerant detection of complex variants and splicing in short reads. Bioinformatics 26, 373-881 (2010).
Li, H. et al. The Sequence alignment/map (SAM) format and SAMtools. Bioinformatics 25, 2078-2079 (2009).
Kharchenko, P. K., Tolstorukov, M. Y. & Park, P. J. Design and analysis of ChIP-seq experiments for DNA-binding proteins. Nat. Biotechnol. 26, 1351-1359 (2008).
Heinz, S. et al. Simple combinations of lineage-determining transcription factors prime cis-regulatory elements required for macrophage and B cell identities. Mol. Cell 38, 576-589 (2010).
Kent et al. The human genome browser at UCSC. Genome Res. 12, 996-1006 (2002).
Larson, E. D., St Clair, J. R., Sumner, W. A., Bannister, R. A. & Proenza, C. Depressed pacemaker activity of sinoatrial node myocytes contributes to the age-dependent decline in maximum heart rate. Proc. Natl Acad. Sci. USA 110, 18011-18016 (2013).
Lopez, A. D., Mathers, C. D., Ezzati, M., Jamison, D. T. & Murray, C. J. Global and regional burden of disease and risk factors, 2001: systematic analysis of population health data. Lancet 367, 1747-1757 (2006).
Laflamme, M. A. & Murry, C. E. Regenerating the heart. Nat. Biotechnol. 23, 845-856 (2005).
Mercola, M., Ruiz-Lozano, P. & Schneider, M. D. Cardiac muscle regeneration: lessons from development. Genes Dev. 25, 299-309 (2011).
Porter, K. E. & Turner, N. A. Cardiac fibroblasts: at the heart of myocardial remodeling. Pharmacol. Ther. 123, 255-278 (2009).
Tomasek, J. J., Gabbiani, G., Hinz, B., Chaponnier, C. & Brown, R. A. Myofibroblasts and mechano-regulation of connective tissue remodelling. Nat. Rev. Mol. Cell Biol. 3, 349-363 (2002).
Davis, J. & Molkentin, J. D. Myofibroblasts: trust your heart and let fate decide. J. Mol. Cell Cardiol. 70, 9-18 (2014).
Weber, K. T., Sun, Y., Bhattacharya, S. K., Ahokas, R. A. & Gerling, I. C. Myofibroblast-mediated mechanisms of pathological remodelling of the heart. Nat. Rev. Cardiol. 10, 15-26 (2013).

(Continued)

*Primary Examiner* — Daniel C Gamett
(74) *Attorney, Agent, or Firm* — Michael M. McGaw; Smith & Hopen, P.A.

(57) ABSTRACT

Pro-fibrotic signaling potently antagonizes cardiac reprogramming. Inhibition of pro-fibrotic signaling using small molecules that target the transforming growth factor-β/SMAD, or Rho kinase leads to conversion of approximately 60% of fibroblasts into beating cardiomyocytes. Conversely, over-activation of these pro-fibrotic signaling networks inhibits cardiac reprogramming. Using the disclosed methods, fibroblasts are converted to spontaneously contracting cardiomyocytes in less than two weeks.

13 Claims, 49 Drawing Sheets

(56) References Cited

OTHER PUBLICATIONS

Davis, R. L., Weintraub, H. & Lassar, A. B. Expression of a single transfected cDNA converts fibroblasts to myoblasts. Cell 51, 987-1000 (1987).
Takahashi, K. & Yamanaka, S. Induction of pluripotent stem cells from mouse embryonic and adult fibroblast cultures by defined factors. Cell 126, 663-676 (2006).
Vierbuchen, T. et al. Direct conversion of fibroblasts to functional neurons by defined factors. Nature 463, 1035-1041 (2010).
Huang, P. et al. Induction of functional hepatocyte-like cells from mouse fibroblasts by defined factors. Nature 475, 386-389 (2011).
Ieda, M. et al. Direct reprogramming of fibroblasts into functional cardiomyocytes by defined factors. Cell 142, 375-386 (2010).
Song, K. et al. Heart repair by reprogramming non-myocytes with cardiac transcription factors. Nature 485, 599-604 (2012).
Addis, R. C. et al. Optimization of direct fibroblast reprogramming to cardiomyocytes using calcium activity as a functional measure of success. J. Mol. Cell Cardiol. 60, 97-106 (2013).
Qian, L. et al. In vivo reprogramming of murine cardiac fibroblasts into induced cardiomyocytes. Nature 485, 593-598 (2012).
Mathison, M. et al. In vivo cardiac cellular reprogramming efficacy is enhanced by angiogenic preconditioning of the infarcted myocardium with vascular endothelial growth factor. J. Am. Heart Assoc. 1, e005652 (2012).
Mathison, M. et al. 'Triplet' polycistronic vectors encoding Gata4, Mef2c, and Tbx5 enhances postinfarct ventricular functional improvement compared with singlet vectors. J. Thorac. Cardiovasc. Surg. 148, 1656-1664 (2014).
Chen, J. X. et al. Inefficient reprogramming of fibroblasts into cardiomyocytes using gata4, mef2c, and tbx5. Circ. Res. 111, 50-55 (2012).
Muraoka, N. et al. MiR-133 promotes cardiac reprogramming by directly repressing Snai1 and silencing fibroblast signatures. EMBO J. 33, 1565-1581 (2014).
Wang, L. et al. Stoichiometry of Gata4, Mef2c, and Tbx5 influences the efficiency and quality of induced cardiac myocyte reprogramming. Circ. Res. 116, 237-244 (2015).
Hirai, H., Katoku-Kikyo, N., Keirstead, S. A. & Kikyo, N. Accelerated direct reprogramming of fibroblasts into cardiomyocyte-like cells with the MyoD transactivation domain. Cardiovasc. Res. 100, 105-113 (2013).
Hirai, H. & Kikyo, N. Inhibitors of suppressive histone modification promote direct reprogramming of fibroblasts to cardiomyocyte-like cells. Cardiovasc. Res. 102, 188-190 (2014).
Ifkovits, J. L., Addis, R. C., Epstein, J. A. & Gearhart, J. D. Inhibition of TGFb signaling increases direct conversion of fibroblasts to induced cardiomyocytes. PLoS ONE 9, e89678 (2014).
Parker, M. W. et al. Fibrotic extracellular matrix activates a profibrotic positive feedback loop. J. Clin. Invest. 124, 1622-1635 (2014).
Dijke, P. & Arthur, H. M. Extracellular control of TGFbeta signalling in vascular development and disease. Nat. Rev. Mol. Cell Biol. 8, 857-869 (2007).
Kalluri, R. & Weinberg, R. A. The basics of epithelial-mesenchymal transition. J. Clin. Invest. 119, 1420-1428 (2009).
Mikkelsen, T. S. et al. Dissecting direct reprogramming through integrative genomic analysis. Nature 454, 49-55 (2008).
Onder, T. T. et al. Chromatin-modifying enzymes as modulators of reprogramming. Nature 483, 598-602 (2012).
Koche, R. P. et al. Reprogramming factor expression initiates widespread targeted chromatin remodeling. Cell Stem Cell 8, 96-105 (2011).
Chen, J. F. et al. The role of microRNA-1 and microRNA-133 in skeletal muscle proliferation and differentiation. Nat. Genet. 38, 228-233 (2006).
Liu, N. et al. MicroRNA-133a regulates cardiomyocyte proliferation and suppresses smooth muscle gene expression in the heart. Genes Dev. 22, 3242-3254 (2008).
Zhao, Y., Samal, E. & Srivastava, D. Serum response factor regulates a musclespecific microRNA that targets Hand2 during cardiogenesis. Nature 436, 214-220 (2005).
Rao, P. K., Kumar, R. M., Farkhondeh, M., Baskerville, S. & Ladish, H. F. Myogenic factors that regulate expression of muscle-specific microRNAs. Proc. Natl Acad. Sci. USA 103, 8721-8726 (2006).
Wystub, K., Besser, J., Bachmann, A., Boettger, T. & Braun, T. miR-1/133a clusters cooperatively specify the cardiomyogenic lineage by adjustment of myocardin levels during embryonic heart development. PLoS Genet. 9, e1003793 (2013).
Ladewig, J. et al. Small molecules enable highly efficient neuronal conversion of human fibroblasts. Nat. Methods 9, 575-578 (2012).
Xu, Y. et al. Revealing a core signaling regulatory mechanism for pluripotent stem cell survival and self-renewal by small molecules. Proc. Natl Acad. Sci. USA 107, 8129-8134 (2010).
Feng, Y. et al. Discovery of substituted 4-(pyrazol-4-yl)-phenylbenzodioxane-2-carboxamides as potent and highly selective Rho kinase (Rock-II) inhibitors. J. Med. Chem. 51, 6642-6645 (2008).
Tojo, M. et al. The ALK-5 inhibitor A-83-01 inhibits Smad signaling and epithelial-to-mesenchymal transition by transforming growth factor-beta. Cancer Sci. 96, 791-800 (2005).
Sawyer, J. S. et al. Synthesis and activity of new aryl- and heteroaryl-substituted pyrazole inhibitors of the transforming growth factor-beta type I receptor kinase domain. J. Med. Chem. 46, 3953-3956 (2003).
Uhl, M. et al. SD-208, a novel transforming growth factor beta receptor I kinase inhibitor, inhibits growth and invasiveness and enhances immunogenicity of murine and human glioma cells in vitro and in vivo. Cancer Res. 64, 7954-7961 (2004).
Tan, S. M., Zhang, Y., Connelly, K. A., Gilbert, R. E. & Kelly, D. J. Targeted inhibition of activin receptor-like kinase 5 signaling attenuates cardiac dysfunction following myocardial infarction. Am. J. Physiol. Heart Circ. Physiol. 298, H1415-H1425 (2010).
Maltsev, V. A., Wobus, A. M., Rohwedel, J., Bader, M. & Hescheler, J. Cardiomyocytes differentiated in vitro from embryonic stem cells developmentally express cardiac-specific genes and ionic currents. Circ. Res. 75, 233-244 (1994).
Nagashima, M. et al. Alternation of inwardly rectifying background K. channel during development of rat fetal cardiomyocytes. J. Mol. Cell Cardiol. 33, 533-543 (2001).
Stadtfeld, M., Maherali, N., Borkent, M. & Hochedlinger, K. A reprogrammable mouse strain from gene-targeted embryonic stem cells. Nat. Methods 7, 53-55 (2010).
Liu, Y. & Schwartz, R. J. Reprogrammed cardiac fibroblasts to the rescue of heart failure. Circ. Res. 111, 831-832 (2012).
Hansson, E. M. & Chien, K. R. Reprogramming a broken heart. Cell Stem Cell 11, 3-4 (2012).
Wamstad, J. A. et al. Dynamic and coordinated epigenetic regulation of developmental transitions in the cardiac lineage. Cell 151, 206-220 (2012).
Paige, S. L. et al. A temporal chromatin signature in human embryonic stem cells identifies regulators of cardiac development. Cell 151, 221-232 (2012).
Olson, E. N. Gene regulatory networks in the evolution and development of the heart. Science 313, 1922-1927 (2006).
Sandbo, N. et al. Delayed stress fiber formation mediates pulmonary myofibroblast differentiation in response to TGF-b. Am. J. Physiol. Lung Cell Mol. Physiol. 301, L656-L666 (2011).

\* cited by examiner

HIGH EFFICIENCY REPROGRAMMING OF FIBROBLASTS INTO CARDIOMYOCYTES

CROSS-REFERENCE TO RELATED APPLICATIONS

This application claims the benefit of U.S. Provisional Application No. 62/133,716, filed Mar. 16, 2015.

BACKGROUND OF THE INVENTION

1. Field of Invention

This invention relates to treatment of heart disease. More specifically, this invention relates to the conversion of fibrobalsts into cardiomyocytes through the suppression of pro-fibrotic signaling.

2. Brief Description of the Related Art

Heart disease is often caused by the loss or dysfunction of cardiomyocytes. [Lopez, A. D., et al. *Lancet* 367, 1747-1757 (2006)] The mammalian heart is composed of approximately 30% cardiomyocytes, which have limited capacity to regenerate [Laflamme, M. A., & Murry, C. E. *Nat. Biotechnol.* 23, 845-856 (2005); Mercola, M., et al., *Genes and Development* 25, 299-309 (2011)] and approximately 60% cardiac fibroblasts (CFs). [Porter, K. E., & Turner, N. A., *Pharmacol. Ther.* 123, 255-278 (2009)] In injured hearts, CFs are activated by pro-fibrotic signaling, including transforming growth factor-β/SMAD (TGF-β/SMAD), and Rho kinase pathways and express high levels of smooth muscle α-actin (αSMA) and extracellular matrix (ECM) proteins, leading to pathological fibrosis. [Tomasek, J. J., et al., *Nat. Rev. Mol. Cell Biol.* 3, 349-63 (2002); Davis, J., & Molkentin, J. D., *J. Mol. Cell Cardiol.* 70, 9-18 (2014); Weber, K. T., Sun, Y., et al., *Nat. Rev. Cardiol.* 10, 15-26 (2013)] Fibroblasts demonstrate plasticity, and can be reprogrammed into skeletal muscle cells, induced pluripotent stem (iPS) cells, neurons and hepatocytes. [Davis, R. L., et al., *Cell* 51, 987-1000 (1987); Takahashi, K. & Yamanaka, S., *Cell* 126, 663-676 (2006); Vierbuchen, T. et al., *Nature* 463, 1035-1041 (2010); Huang, P. et al., *Nature* 475, 386-9 (2011)] Recently, three transcription factors, GATA4, MEF2C, and Tbx5 (GMT) were shown to reprogram mouse fibroblasts into cardiomyocyte-like cells (iCMs), albeit at low efficiency. [Ieda, M. et al., *Cell* 142, 375-386 (2010)] Adding Hand2 in GMT (GHMT) enhanced reprogramming efficiency. [Song, K. et al., *Nature* 485, 599-604 (2012); Addis, R. C. et al., *J. Mol. Cell Cardiol.* 60, 97-106 (2013)] Interestingly, forced expression of GMT or GHMT in myocardium following myocardial infarction (MI) blunted cardiac dysfunction and diminished myocardial remodeling in mice and rats. [Song, K. et al., *Nature* 485, 599-604 (2012); Qian, L. et al., *Nature* 485, 593-598 (2012); Mathison, M. et al., *J. Am. Heart Assoc.* 1, e005652 (2012); Mathison, M. et al., *J. Thorac. Cardiovasc. Surg.* 148, 1656-1664 (2014)] Intense investigation has focused on enhancing cardiomyogenic reprogramming since GMT-mediated reprogramming is slow and inefficient. [Chen, J. X. et al., *Circ. Res.* 111, 50-5 (2012)] The present invention addresses this important shortcoming in the prior art by providing methods for reprogramming fibroblasts that are far more efficient and rapid than prior methodologies as will become apparent in the following disclosure.

BRIEF SUMMARY OF THE INVENTION

We demonstrate that pro-fibrotic signaling potently antagonizes cardiac reprogramming. Inhibition of pro-fibrotic signaling using small molecules that target the transforming growth factor-β/SMAD, or Rho kinase leads to conversion of approximately 60% of fibroblasts into beating cardiomyocytes. Conversely, over-activation of these pro-fibrotic signaling networks inhibits cardiac reprogramming. Using the disclosed methods, fibroblasts are converted to spontaneously contracting cardiomyocytes in less than two weeks. These findings provide new insights into the molecular mechanisms underlying cardiac conversion of fibroblasts, and will enhance efforts to generate cardiomyocytes for clinical applications.

In a first aspect the present invention provides a method of converting a fibroblast into a cardiomyocyte. The method includes the step of delivering either of the reprogramming factors miR-1 or miR-133 in combination with one or more of the reprogramming factors GATA4, Hand2, MEF2C, and Tbx5 to the fibroblast.

In certain embodiments all of the reprogramming factors (i.e. GATA4, Hand2, MEF2C, Tbx5, miR-1, and miR-133-collectively "GHMT2m"), will be delivered to the fibroblasts. In an advantageous embodiment GHMT2m will be delivered to the fibroblast along with the small molecule A83-01.

In other embodiments the reprogramming factors is GATA4, Hand2, MEF2C, Tbx5, and miR-133 will be delivered to the fibroblast, with or without the small molecule A83-01. In still other embodiments the reprogramming factors GATA4, Hand2, MEF2C, Tbx5, and miR-1 will be delivered to the fibroblast, with or without the small molecule A83-01.

In certain embodiments the method of the first aspect will include delivering a small molecule that targets RhoA-ROCK signaling to the fibroblast. The small molecule can be a ROCK inhibitor such as Y-27632, GW788388, Thiazovivin or SR-3677. The method can also include delivering a small molecule that targets TGF-β signaling. The small molecule can be a TGF-β inhibitor such as A 83-01, LY-364947, SD-208 or GW788388.

In a second aspect the present invention provides a second method of converting a fibroblast into a cardiomyocyte. The method includes the step of delivering to the fibroblast a combination of reprogramming factors selected from the group consisting of GATA4, Hand2, MEF2C, and Tbx5 (GHMT) and a small molecule that inhibits TGF-β signaling or a small molecule that targets RhoA-ROCK signaling. The ROCK inhibitor can be Y-27632, GW788388, Thiazovivin or SR-3677. The TGF-β inhibitor can be A 83-01, LY-364947, SD-208 or GW788388.

In a third aspect the present invention provides a third method of converting a fibroblast into a cardiomyocyte. The method includes the step of contacting the fibroblast with the reprogramming factors miR-1, miR-133, GATA4, Hand2, MEF2C, and Tbx5 and the small molecule A83-01. In certain embodiments the method will further include contacting the fibroblast with Y27632.

In a fourth aspect the present invention provides a method of treating myocardial infarction in a subject. The method includes the step of delivering to the heart of the subject reprogramming factors GATA4, Hand2, MEF2C, Tbx5, miR-1, and miR-133 expression cassettes in combination with a small molecule that inhibits TGF-β signaling or a small molecule that targets RhoA-ROCK signaling. The small molecule that targets RhoA-ROCK signaling can be Y-27632, GW788388, Thiazovivin or SR-3677. The small molecule that inhibits TGF-β signaling can be A 83-01, LY-364947, SD-208 or GW788388. The expression cassettes can be within replicable vectors. Furthermore, in certain embodiments the replicable vectors can be viral vectors, adenoviral vectors or retroviral vectors. Alternatively, the replicable vectors can be non-viral vectors. In certain embodiments the non-viral vectors can be disposed in a lipid delivery vehicle.

In an advantageous embodiment the expression cassettes are delivered 24 hours to one month following myocardial infarction. The expression cassettes can be delivered multiple times. For example, can be delivered 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 times. Moreover, the expression cassettes can be delivered daily. Additionally, the expression cassettes can be delivered via intracardiac injection.

BRIEF DESCRIPTION OF THE DRAWINGS

For a fuller understanding of the invention, reference should be made to the following detailed description, taken in connection with the accompanying drawings, in which:

FIG. 1 is a pair of graphs illustrating the dynamic changes of pro-fibrotic signaling pathways in reprogramming cells. The graphs show messenger RNA expression of pro-fibrotic markers, including Col1a1 and Fn-EDA. Samples were harvested from 3 independent experiments and measured in duplicate. Data are presented as mean±SD. Gene expression was normalized to GAPDH.

FIG. 2 is an image showing immunoblot analysis of phospho-Smad2, αSMA, Snail, and Slug in GFP- or GHMT-infected MEFs at day 5 and day 7 (n=3).

FIG. 3 is an image of an immunoblot showing phospho-Smad2 and αSMA expression in GHMT-infected MEFs at day 5, day 7 and day 14 (n=3). GAPDH serves as a loading control.

FIG. 4 is a graph showing the quantification of cTnT+, cTnTlow and cTnThigh cells shown in FIG. 5 (n=4 for GFP, n=5 for 2 m, n=11 for GHMT and GHMT2m). Data are presented as mean+ standard deviation (SD). n.s, not significant. Within each set (cTnT+, cTnTlow and cTnThigh) the samples are presented in the following order from left to right; GFP, 2 m, GHMT, GHMT2m.

FIG. 5 is a set of four graphs showing flow cytometry analysis for cTnT+ cells at day 7-post viral infection. Numbers embedded in each graph indicate the percentages of cTnT-, cTnTlow and cTnThigh cells shown from left to right. 2 m (miR-1+miR-133); GHMT2m (GHMT+miR-1+miR-133); FSC, forward scatter.

FIG. 6 is a set of eight representative immunofluorescence images of MEFs stained for cardiomyocyte markers, cTnT (red (appearing as larger light objects in gray scale and only visible in right two images), upper), and α-actinin (red (appearing as larger light object in gray scale and only visible in right two images), lower). MEFs were infected with retroviruses carrying the indicated factors and cultured for 2 weeks. White boxes are enlarged in insets. Scale bars, 400 µm.

FIG. 7 is a graph showing time course of spontaneously contracting cells induced by indicated factors (n=5 for GHMT, n=4 for GHMTm1, n=5 for GHMTm133 and n=7 for GHMTm2). GHMTm1 (GHMT+miR-1); GHMTm133 (GHMT+miR-133). Data are presented as mean±SDT. At t=30 the plots are in the following order from high to low: GHMT2m, GHMTm1, GHMTm133 and GHMT.

FIG. 8 is a graph showing the population of spontaneously contracting cells induced by indicated factors by 4 weeks (n=4). Data are presented as mean+STD.

FIG. 9 is image showing immunoblots. MEFs were infected with indicated retroviral cocktails, then treated with TGF-β1 (10 ng/ml) for 4 days. Samples were immunoblotted with antibodies to phospho-Smad2, Smad2, Slug and GAPDH.

FIG. 10 is a pair of graphs showing qPCR analysis of the indicated genes. MEFs were infected with indicated retroviral cocktails, then treated with TGF-β1 (10 ng/ml) for 4 days. Withon each replicate, control is on the left and TGF-β1 is on the right.

FIG. 11 is a pair of images showing immunostaining of αSMA+ stress fibers in MEFs overexpressing the indicated factors in the absence of presence of TGF-β1 at day 7. Infected MEFs were treated with TGF-β1 for the 5 days. The number embedded in each image indicates the percentage of cells with stress fibers. Scale bar, 200 µm. Data are presented as mean±SD.

FIG. 12 is a set of six representative immunofluorescence images of MEFs stained for cTnT (red (appearing as larger light objects in gray scale and not visible in the LacZ images)). MEFs were infected with retroviruses carrying the indicated factors and fixed at day 14. White boxes are enlarged in insets. Scale bars, 400 µm. n=3.

FIG. 13 is a graph showing the cTnT+ cells (%) based upon the images in FIG. 12.

FIG. 14 is a set of six representative immunofluorescence images of MEFs stained for α-actinin (red (appearing as larger light objects in gray scale and not visible in the LacZ images)). MEFs were infected with retroviruses carrying the indicated factors and fixed at day 14. White boxes are enlarged in insets. Scale bars, 400 µm. n=3.

FIG. 15 is a graph showing the α-actinin+ cells (%) based upon the images in FIG. 14.

FIG. 16 is a pair of graphs showing qPCR analysis of the indicated cardiac genes in reprogramming cells treated with TGF-β1 or water for 4 days. Non-infected MEFs served as a control. Gene expression was normalized to GAPDH. In each replicate, the bar representing the control is on the left and TGF-β1 is on the right.

FIG. 17 is a graph the time course of spontaneously beating cells in the indicated cultures. n=4. The individual plots at t=30 days are in the following order form high to low: GHMT2m, GHMT, GHMT2m/TGF-β1 coextensive with GHMT/TGF-β1.

FIG. 18 is a set of six representative immunofluorescence images of MEFs stained for cTnT (red—appearing as larger light objects in gray scale and not visible in the GFP images) at day 14. MEFs were infected with retroviruses carrying the indicated factors and treated with Y-27632 (30 µM). The number embedded in each plot indicates the percentage of positive cells for indicated cardiac markers. White boxes are enlarged in insets. Scale bars, 400 µm.

FIG. 19 is a set of six representative immunofluorescence images of MEFs stained for α-actinin (red—appearing as larger light objects in gray scale and not visible in the GFP images) at day 14. MEFs were infected with retroviruses carrying the indicated factors and treated with Y-27632 (30 µM). The number embedded in each plot indicates the percentage of positive cells for indicated cardiac markers. White boxes are enlarged in insets. Scale bars, 400 μm.

FIG. 20 is a graph illustrating the time course of spontaneously contracting cells in GHMT-infected cultures treated with Y-27632 (10, 30 μM) or water (n=3). Data are presented as mean. The upper line plot at t=32 days is GHMT/Y27632 (30 μM), the middle line plot is GHMT/Y27632 (10 μM), and the lower line plot is GHMT.

FIG. 21 is a graph illustrating the time course of spontaneously contracting cells in GHMT2m-infected cultures treated with Y-27632 (30 μM) or water (n=3). Data are presented as mean. The upper line plot at t=12 days is GHMT2m/Y27632 (30 μM) and the lower line plot is GHMT2m (i.e. water-treated).

FIG. 22 is a graph depicting the fractions of beating cells at day 12. n=3.

FIG. 23 is a graph depicting spontaneously beating cells induced by GHMT2m in the presence of the indicated inhibitors of ROCK (n=3). GHMT2m-MEFs were treated with Thiazovivin (2.5 μM), SR-3677 (5 μM), respectively for 7 days. Beating cells were counted at day 9.

FIGS. 24-30: Inhibitors of TGF-β signaling decrease pro-fibrotic gene expression and enhance cardiac reprogramming.

FIG. 25 is a pair of graphs showing the quantification of cTnT+ and α-actinin+ cells in FIGS. 24A and 24B. n=3. Control is on the left and A83-01 is on the left in each replicate.

FIG. 26 is a graph depicting the time course of spontaneously contracting cells in GHMT-infected cultures treated with A83-01 (0.5 μM) or DMSO (n=3). Data are presented as mean±SD. The upper line plot at t=day 31 is GHMT/A 83-01 and the lower plot running roughly along the x-axis is GHMT.

FIG. 27 is a graph depicting the time course of spontaneously contracting cells in GHMT2m-infected cultures treated with A83-01 or DMSO (n=3). Data are presented as mean±SD. The upper line plot at t=day 11 is GHMT2m/A 83-01 and the lower plot is GHMT.

FIG. 28 is a histogram depicting the percentage of spontaneously beating cells in GHMT2m-infected MEFs treated with indicated drugs or DMSO at day 11 (n=3). Data are presented as mean+SD.

FIG. 29 is a histogram depicting the spontaneously beating cells induced by GHMT2m in the presence of the indicated inhibitors of TGF-β signaling. GHMT2m-MEFs were treated with GW788388 (3 μM), LY-364947 (1.5 μM), and SD-208 (1 μM) respectively for 7 days (n=3). Beating cells were counted at day 9. Data are presented as mean+SD.

FIG. 30 is a heat map comparing gene expression in MEFs, GHMT (4F), GHMT2m+A83-01 (6FA) and primary cardiomyocytes NMCM. RNAs were harvested from indicated samples followed by deep sequencing.

FIG. 31 is a pair of images showing immunofluorescence staining of cTnT (red—gray areas in gray scale) and cardiac gap junction connexin-43 (green—light-white linear areas in gray scale at the arrow heads) in GHMT2m-infected cultures treated with A83-01 or Y27632 at day 14. cTnT+ cell A connects to cell B, cell C and cell D via connexin-43 (white arrows). Scale bar, 100 μm.

FIG. 32 is a graph depicting a representative action potential elicited in an induced cardiomyocyte by a 200 pA, 20 ms current injection (arrow; stimulus artifact deleted for clarity) in an amphotericin perforated-patch current-clamp recording.

FIG. 33 is a set of six representative immunofluorescence images of MEFs stained for cTnT (red—appearing as large light gray bodies in the middle and right images) and Myl7 or Myl2 (green—appearing as light to white bodies in the left images) at day 14. White boxes are enlarged in insets. Scale bars, 400 μm.

FIG. 34 is a set of graphs depicting spontaneous action potentials fired by induced cardiomyocytes by GHMT2m plus A83-01 at day 9. Representative group 1 or group 2 spontaneous action potentials recorded using Amphotericin B perforated patch technique. A single action potential from the three second recording window is expanded on the right.

FIG. 35, part A, is a set of six representative immunofluorescence images/panels of adult cardiac fibroblasts (ACFs) stained for cTnT (red—appearing as large light gray bodies in the middle and right images) (b) by 4 weeks. White boxes are enlarged in insets. Scale bars, 400 μm. FIG. 35, part B, shows the quantification of positive cells is shown in the right panels of part A. n=3.

FIG. 36, part A, is a set of six representative immunofluorescence images of adult cardiac fibroblasts (ACFs) stained for α-actinin (red—appearing as large light gray bodies in the middle and right images) by 4 weeks. White boxes are enlarged in insets. Scale bars, 400 μm. FIG. 36, part B, shows the quantification of positive cells is shown in the right panels of part A. n=3.

FIG. 37 is a histogram showing the percentage of spontaneously beating cells in ACFs treated with indicated combinations by 5 weeks (n=3). Data are presented as mean+SD. The left bar in each replicate represents DMSO and the right bar represents A83-01.

FIG. 38 is a set of images and a graph. Part A shows four representative immunofluorescence images of adult tail-tip fibroblasts (ATTFs) stained for α-actinin (red—appearing light gray in the gray scale and evident only in the two images on the right). ATTFs expressing the indicated factors were treated with A83-01 or DMSO for 2 weeks. Scale bars, 100 μm. Quantification of positive cells is shown in the histogram in part B. The left bar in each replicate represents DMSO and the right bar represents A83-01. n=3.

FIG. 39 is a set of images and a graph. Part A shows four representative immunofluorescence images of adult tail-tip fibroblasts (ATTFs) stained for cTnT (red—appearing light gray in the gray scale and evident only in the two images on the right). ATTFs expressing the indicated factors were treated with A83-01 or DMSO for 2 weeks. Scale bars, 100 μm. Quantification of positive cells is shown in the histogram in part B. The left bar in each replicate represents DMSO and the right bar represents A83-01. n=3.

FIG. 40 is a graph of the time course of spontaneously contracting cells in GHMT2m-ATTFs treated with A83-01 (0.5 μM) or DMSO (n=3). Data are presented as mean±SD. The upper plot line in the graph at t=33 days is GHMT2m/A 83-01 and the lower plot line is GHMT2m.

FIG. 41 is a histogram showing the percentage of spontaneously beating cells in ATTFs treated with indicated combinations by 5 weeks (n=3). Data are presented as mean+SD.

FIG. 43 is a set of graphs showing the time course of cTnT expression induced by GHMT. The scheme of factor-mediated cardiac reprogramming is shown in the timeline in the upper illustration. To prepare the samples shown in the remainder of the graphs/plots, MEFs were prepared from C57Bl6 embryos at embryonic day 14.5 (E14.5). The number embedded in each plot indicates percentage of cTnT+ cells.

FIG. 44 is a histogram that shows the quantification of cTnT+ cells analyzed by flow cytometry in a (n=2). Data are presented as mean+SD.

FIG. 45 is a pair of plots that show flow cytometry analysis for expression of reprogramming factors in MEFs. MEFs were infected with retroviruses encoding GFP or GHMT (each factor tagged with Myc) and analyzed at day 6. The percentage of cells positive for Myc expression in each group is shown.

FIG. 46 is a set of four histograms addressing messenger RNA expression of myofibroblast markers, including αSMA, Col1a1, Fn-EDA and Col3a1. Samples were harvested from 4 independent experiments and measured in duplicate. A representative pattern is shown. Data are presented as mean+SD.

FIG. 47 is a set of four histograms. The time course of expression of the indicated genes in GFP- and GHMT-MEFs was determined by qPCR. A representative pattern from two independent experiments is shown.

FIG. 48 is a histogram detailing the results of qPCR analysis for expression of epithelial-to mesenchymal transition (EMT) markers, Snail and Slug, in GFP- and GHMT-MEFs at day 5 and day 7. A representative pattern from two independent experiments is shown. In each replicate the day 5 sample is on the left and the day 7 sample is on the right.

FIG. 49 is a bar graph and Venn diagram illustrating the number of cardiomyocyte-exclusive or MEF-exclusive H3K4me2 peaks gained or lost during reprogramming. Venn diagram of represented peaks within reprogramming cells at day 7 versus MEFs and primary neonatal mouse ventricular cardiomyocytes (NMVM).

FIG. 50 is a set of graphs. ChIP-Seq tracks showing a gain of H3K4me2 at the locus of the miR-133a-1 and miR-1-2 cluster at the early stages of reprogramming. However, increased H3K4me2 was not detected at miR-499 and miR-208 loci at the same time point.

FIG. 51 is a set of three histograms addressing qPCR analysis of the indicated cardiac genes in MEFs. MEFs were infected with retroviruses carrying the indicated factors and cultured for 7 days.

FIG. 52 is a set of plots detailing the results of flow cytometry analysis for cTnT+ cells at day 7. The number embedded in each plot indicates the percentage of cTnThigh cells. 2 m (miR-1+miR-133); GHMTm1 (GHMT+miR-1); GHMTm133 (GHMT+miR-133); GHMT2m (GHMT+miR-1+miR-133).

FIG. 53 is a histogram showing the quantification of cTnThigh cells shown in FIG. 52. (n=4 for GFP, n=5 for 2 m, n=4 for GHMTm1 and GHMTm133, n=11 for GHMT and GHMT2m). Data are presented as mean+SD. n.s, not significant.

FIG. 54 is a histogram showing the results of qPCR analysis of Fn-EDA in Y-27632 treated reprogramming cells at day 7. Gene expression was normalized to GAPDH.

FIG. 56 is an image showing an immunoblot. Expression of αSMA, Snail, Slug and GAPDH protein in MEFs overexpressing the indicated factors in the absence of presence of Y-27632 at day 7. Infected MEFs were treated with Y-27632 at 10 μM for 2 days, and then at 30 μM for the other two days.

FIG. 56 is a pair of images showing immunostaining of αSMA+ stress fibers in MEFs overexpressing the indicated factors in the absence of presence of Y-27632 at day 7. Infected MEFs were treated with Y-27632 at 10 μM for 2 days, and then at 30 μM for the other two days. The number embedded in each plot indicates the percentage of cells with stress fibers. Scale bar, 400 μm. Data are presented as mean±SD.

FIG. 57 is a set of six histograms showing the results of qPCR analysis for expression of indicated cardiac genes in reprogramming cells at day 7. MEFs infected with retroviruses carrying the indicated factors were treated with Y-27632 or water for 5 days. Gene expression was normalized to GAPDH.

FIG. 58 is an image of an immunoblt. MEFs were infected with the indicated retroviral cocktails, then treated with A83-01 (0.5 μM) or DMSO until samples were harvested. Cell lysates at day 7 were immunoblotted with antibodies to phospho-Smad2, Smad2, Slug, αSMA and GAPDH.

FIG. 59 is a set of three histograms showing the results of qPCR analysis of the indicated gene expression at day 7 (n=4). Gene expression was normalized to GAPDH.

FIG. 60 is a pair of images showing immunostaining of αSMA+ stress fibers in MEFs overexpressing the indicated factors in the absence of presence of A83-01 at day 7. Infected MEFs were treated with A83-01 for 5 days. The number embedded in each plot indicates the percentage of cells with stress fibers. Scale bar, 200 μm. Data are presented as mean±SD.

FIG. 61 is a set of plots showing flow cytometry analysis for cTnT expression in infected MEFs at day 7. MEFs were infected with the indicated retroviral cocktails, then treated with the TGF-β inhibitor, A83-01 (0.5 μM) or DMSO from day 3 to day 7. The number embedded in each plot indicates the percentage of cTnThigh cells.

FIG. 64 is a set of eight images showing the expression of GFP in MEFs delivered by AAV. GFP is evident as lighter shaded areas in the GFP samples.

FIG. 65 is a set of four representative immunofluorescence images of MEFs stained for cTnT (red, upper—appearing as large gray bodies only in the AAV-GHMG2m image), and α-actinin (red, lower—appearing as large gray bodies only in the AAV-GHMG2m image). MEFs were infected with AAV-GHMT2m and treated with A83-01 or DMSO for 12 days. Scale bars, 100 μm.

FIG. 66 shows the results of qPCR analysis for expression of the indicated cardiac genes in ACFs. ACFs were infected with indicated retroviruses and treated with A83-01 or DMSO for 4 weeks. Gene expression was normalized to GAPDH. TTFs were used as a negative control. U.D, undetected.

FIG. 67 shows the results of qPCR analysis for expression of the indicated cardiac genes in TTFs. TTFs were infected with indicated retroviruses and treated with A83-01 or DMSO for 4 weeks. Gene expression was normalized to GAPDH. TTFs were used as a negative control. U.D, undetected.

DETAILED DESCRIPTION OF THE PREFERRED EMBODIMENT

Direct reprogramming of fibroblasts into cardiomyocytes by forced expression of cardiomyogenic factors has recently been demonstrated, suggesting a novel therapeutic strategy for cardiac repair. However, current reprogramming approaches are inefficient. Here, we demonstrate that pro-fibrotic signaling potently antagonizes cardiac reprogramming. Inhibition of pro-fibrotic signaling using small molecules that target the transforming growth factor-β/SMAD, or Rho kinase leads to conversion of approximately 60% of fibroblasts into beating cardiomyocytes. Conversely, over-activation of these pro-fibrotic signaling networks inhibits cardiac reprogramming. Using the disclosed methods, fibroblasts are converted to spontaneously contracting cardiomyocytes in less than two weeks. These findings provide new insights into the molecular mechanisms underlying cardiac conversion of fibroblasts, and will enhance efforts to generate cardiomyocytes for clinical applications.

Figure 42:
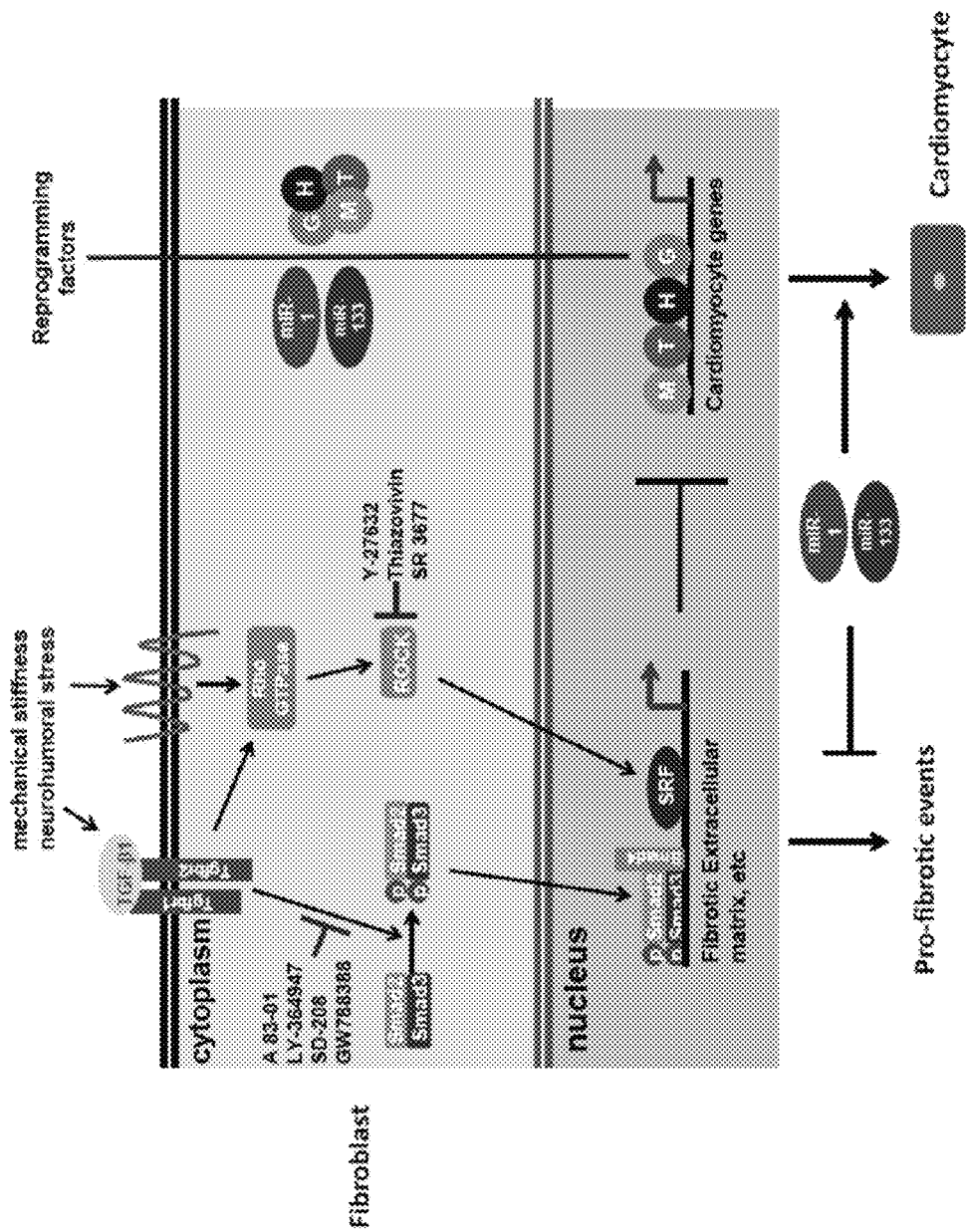
FIG. 42 is an illustration depicting a model for inhibition of cardiomyogenesis by signaling cascades that promote fibrotic events. Pro-fibrotic events are governed by TGF-β and/or ROCK signaling. Phosphorylated Smad2 and Smad3 translocate into nucleus to activate profibrotic genes. Activated ROCK promotes pro-fibrotic events by enhancing actin assembly and activation of pro-fibrotic genes. Profibrotic events serve as barriers to GHMT-mediated cardiac reprogramming. Small molecules that inhibit pro-fibrotic events by targeting either TGF-β signaling or RhoA-ROCK signaling are able to enhance reprogramming of fibroblasts into beating cardiomyocytes. mir-1 and miR-133 enhance cardiac reprogramming by attenuating pro-fibrotic gene expression and other unknown mechanisms.

Direct conversion of fibroblasts into cardiac muscle represents a promising approach for cardiac regeneration and would benefit patients with ischemic heart disease. [Liu, Y., & Schwartz, R. J., *Circ. Res.* 111, 831-2 (2012); Hansson, E. M., & Chien, K. R. *Cell Stem Cell* 11, 3-4 (2012)] Here, highly effective methods for reprogramming fibroblasts into functional cardiomyocytes are disclosed, and it is demonstrated that pro-fibrotic signaling serves as a major barrier to cardiac lineage reprogramming (FIG. 42). Over-activation of pro-fibrotic signaling by TGF-β1 inhibits cardiac reprogramming. Conversely, inhibition of myofibroblast differentiation using small molecules that target either RhoA-ROCK or TGF-β signaling dramatically enhanced the ability of cardiogenic factors to reprogram mouse fetal and adult fibroblast into beating cardiomyocytes (FIG. 42). These findings can be translated into clinical applications, and also provide a novel and facile system to study cardiomyogenesis.

Activation of lineage specific genes by transcription factors largely depends on chromatin alterations. During differentiation of ES cells into cardiomyocytes, promoters of cardiomyocyte genes are gradually marked by H3K4me3 associated with gene activation and expression. [Wamstad, J. A. et al., *Cell* 151, 206-20 (2012); Paige, S. L. et al., *Cell* 151, 221-32 (2012)] Cardiomyogenesis is regulated by a transcriptional cascade, and the first wave of cardiogenic factors induces the second wave of factors. [Olson, E. N., *Science* 313, 1922-7 (2006)] Overexpression of GHMT likely leads to active histone mark(s) at regulatory regions of key factors promoting cardiomyogenesis in fibroblasts. ChIP-Seq revealed that active histone mark, H3K4me2, significantly increased at the regulatory region of the miR-1-2 and miR-133a-1 cluster. MiR-1 and miR-133 promote cardiac muscle formation by several mechanisms, including inhibiting αSMA expression. Our data reveal that miR-1 and miR-133 enhance cardiac reprogramming at least in part, by attenuating pro-fibrotic gene expression (FIG. 42).

Pro-fibrotic event is induced by sequential regulation of signaling pathways. [Sandbo, N. et al., *Am. J. Physiol. Lung Cell Mol. Physiol.* 301, L656-66 (2011)] Activation of TGF-β signaling occurs early, whereas, the delayed activation of RhoAROCK pathway helps to maintain myofibroblast phenotype. It was observed that Y-27632, a ROCK inhibitor, inhibited expression of pro-fibrotic markers less efficiently than A83-01, a TGF-β signaling inhibitor (FIGS. 54-63), and this correlated with the generation of induced cardiomyocytes.

TGF-β signaling plays a critical role in diverse biological processes including cell growth, differentiation and development. Here, it is demonstrated that TGF-β signaling inhibits GHMT-mediated cardiac reprogramming by promoting fibrotic events. These findings may be related to the effect of TGF-β inhibition on the specification and differentiation of cardiomyocytes from mesoderm cells. Thus, cardiomyogenesis occurring during differentiation of ES cells or GHMT-mediated reprogramming of fibroblasts likely occurs via common mechanisms.

Here, it is shown that cardiomyocyte lineage factors GHMT and A83-01 induced approximately 4400 beating cells from 5,000 MEFs by week 4. The combination of GHMT2m (GHMT2m is a combination of genes: GATA4, Hand2, MEF2C, Tbx5, miR-1, miR-133) and A83-01 induced approximately 7000 contracting cells from 5,000 MEFs at day 11, or approximately 500 beating cells from 5,000 TTFs by one month. In these studies, spontaneously contracting cells did not form colonies, suggesting that GHMT/GHMT2m might induce beating cardiomyocytes from fibroblasts through a path different from pluripotent factors mediated cardiac reprogramming. Therefore, these studies provide an additional approach to efficiently convert fibroblasts into spontaneously beating cardiomyocytes.

Loss of cardiomyocytes, cardiac hypertrophy and fibrosis are major factors contributing to pathological ventricular remodeling in patients post-MI. Treatment with GW788388 (FIG. 29) significantly decreased TGF-β activity, cardiac fibrosis and ventricular remodeling with attenuation of systolic dysfunction in rats following MI. The ROCK inhibitor Y-27632 (FIGS. 18-23) can result in decreased infarct size and remodeling in mice following ischemia/reperfusion injury. These small molecules enhance GHMT/GHMT2m-mediated cardiomyocyte conversion by blocking pro-fibrotic signaling, and highlight the potential of a strategy that combines reprogramming factors with anti-fibrotic compounds as a means of regenerating cardiac tissue post-MI.

Figure 43:
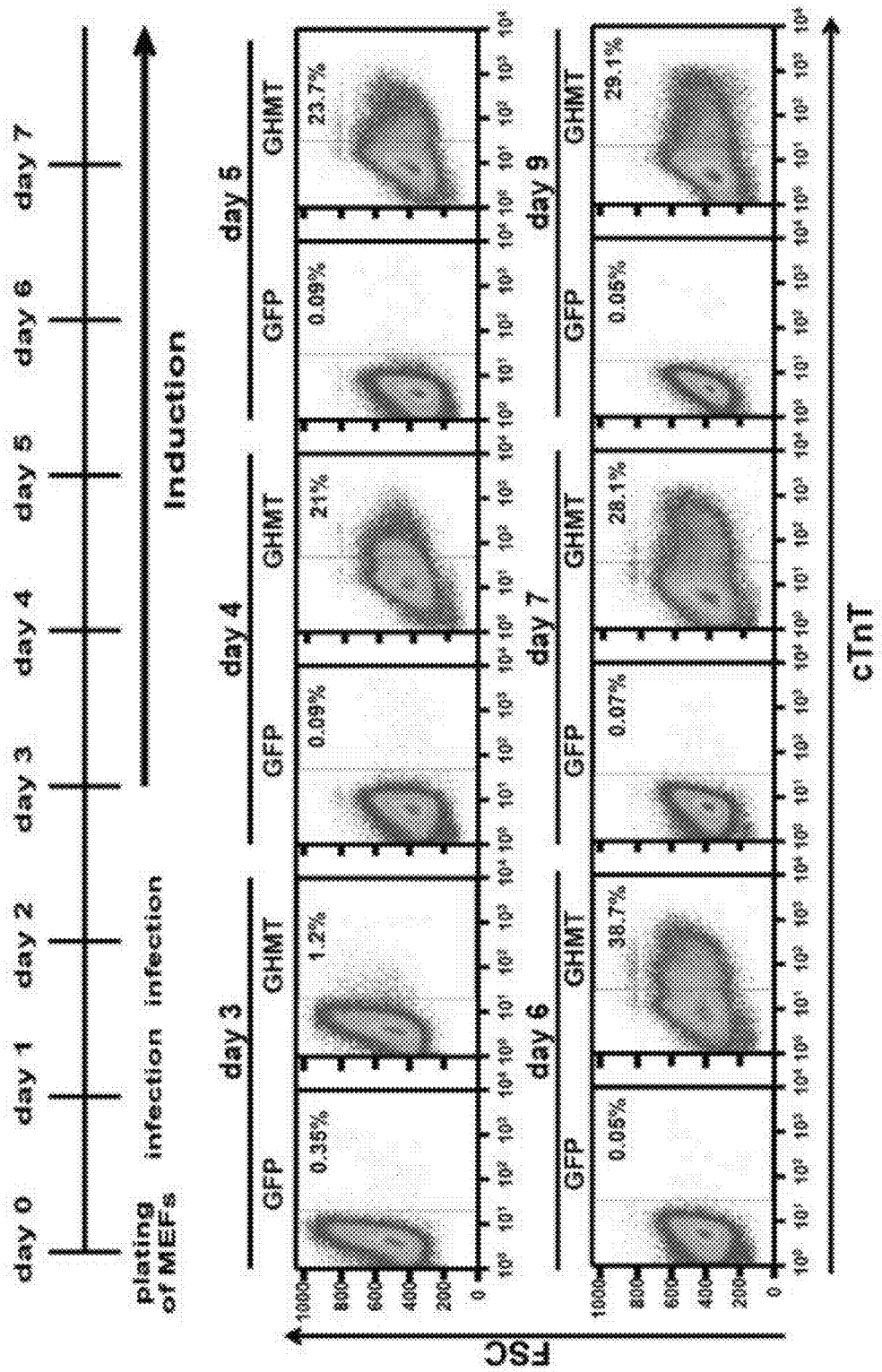
FIGS. 43-45. Induction of cTnT expression by GHMT.
Figure 44:
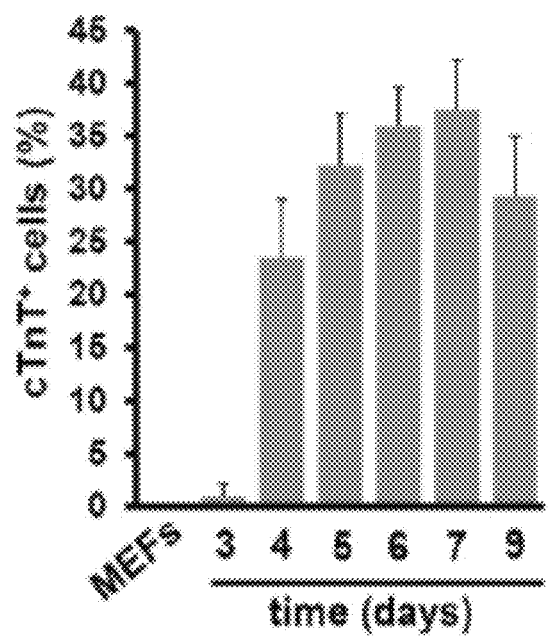
Figure 45:
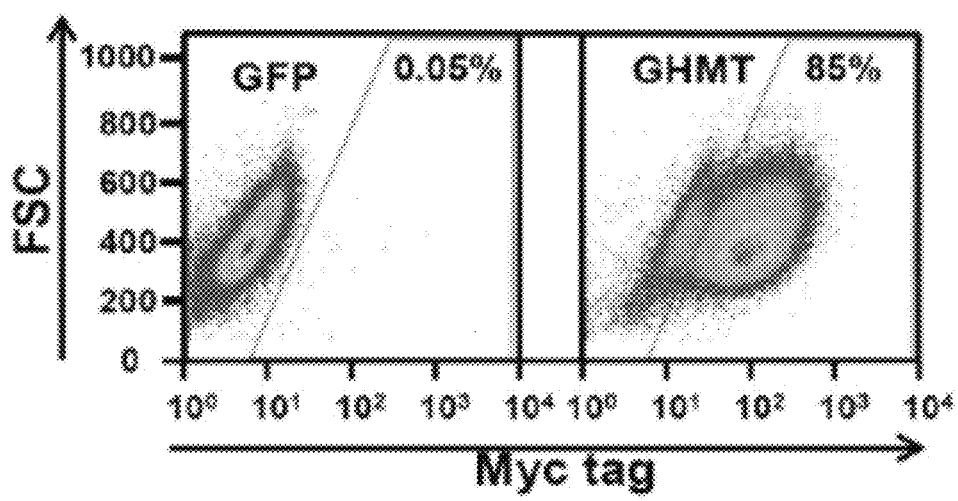

Example 1—Dynamic Changes of Pro-Fibrotic Events Occur During GHMT-Mediated Reprogramming After expression of GHMT, the fraction of cells positive for cardiac troponin T (cTnT), a cardiomyocyte marker, increased with time and reached approximately 37% at day 6 (FIGS. 43 and 44). After one month, about 200 (n=6) beating cells per $cm^2$ were observed, which is about 0.3% of total cells in dishes. GHMT retroviruses infected more than 80% of MEFs (FIG. 2), but less than 1% of infected cells were reprogrammed into beating cardiomyocytes, suggesting endogenous barriers to cardiac reprogramming.

To search for these endogenous barriers, RNA sequencing (RNA-Seq) for genes regulated by GHMT overexpression at day 7 was performed. Gene ontology analysis was used to determine biological functions of genes that were up-regulated more than 2-fold by GHMT. RNA-Seq results showed that gene ontologies related to heart development are enriched among genes up-regulated by GHMT (Table 1). Surprisingly, several ECM ontologies were identified that are among genes up-regulated by GHMT at day 7 (Table 1). Testing was conducted to determine if activation of ECM expression by pro-fibrotic signaling in GHMT-infected fibroblasts suppresses conversion of the cells into cardiomyocytes.

TABLE 1

Dynamic changes of pro-fibrotic signaling pathways in reprogramming cells.

| Genes | | GO Description | Enrichment Score | P-value |
|---|---|---|---|---|
| Up-regulated in GHMT at Day 7 | Cardiac Development | contractile fiber part | 42.03 | 5.57E−19 |
| | | muscle system process | 31.15 | 2.97E−14 |
| | | Z disc | 30.84 | 4.03E−14 |
| | | regulation of heart contraction | 25.5 | 8.45E−12 |
| | | regulation of cardiac muscle contraction | 17.43 | 2.68E−08 |
| | | Cardiac muscle contraction | 16.23 | 8.92E−08 |
| | | Myofibril assembly | 13.07 | 2.11E−06 |
| | | Positive regulation of heart growth | 13.39 | 1.53E−06 |
| | | Cardiac conduction | 12.72 | 2.99E−06 |
| | | Cell communication involved in cardiac conduction | 12.5 | 3.71E−06 |
| | | Cardiac muscle tissue morphogenesis | 11.14 | 1.46E−05 |
| | | Cardiac muscle cell action potential | 10.82 | 1.99E−05 |
| | | Regulation of heart rate | 10.51 | 2.72E−05 |
| | | Ventricular cardiac muscle cell action potential | 9.98 | 4.63E−05 |
| | | Regulation of cardiac muscle contraction by calcium ion signaling | 9.87 | 5.16E−05 |
| | | Cardiac muscle cell development | 9.77 | 5.70E−05 |
| | Fibrotic Events | Extracellular region part | 33.23 | 3.69E−15 |
| | | Extracellular organelle | 26.76 | 2.40E−12 |
| | | Extracellular vesicular exosome | 26.76 | 2.40E−12 |
| | | Extracellular membrane-bounded organelle | 26.76 | 2.40E−12 |
| | | Basement membrane | 21.5 | 4.60E−10 |
| | | Extracellular matrix | 19.2 | 4.57E−09 |
| | | Extracellular matrix organization | 13.24 | 1.78E−06 |
| | | Extracellular structure organization | 13.04 | 2.17E−06 |
| | | Collagen trimer | 10.41 | 3.02E−05 |

RNA-Seq analysis of MEFs and MEFs infected with GHMT at day 7. Genes up-regulated ≥1.5 folds in GHMT were used for gene ontology analysis.

Figure 1:
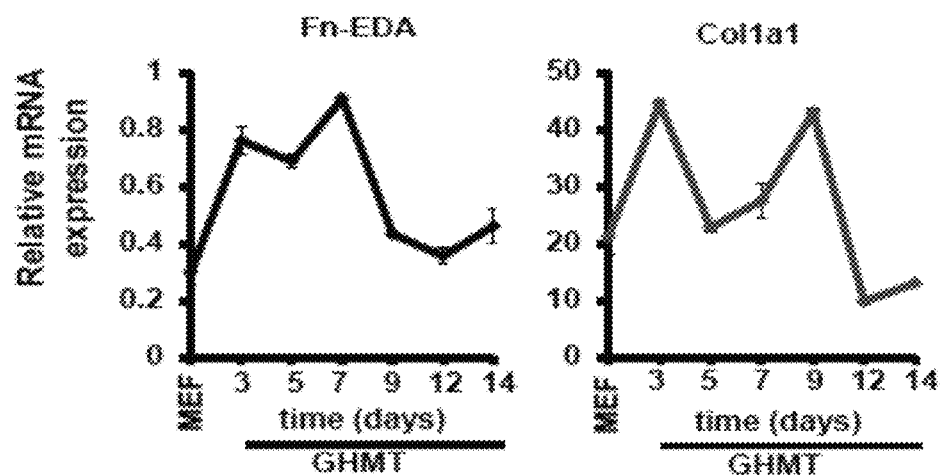
FIGS. 1-3: Dynamic changes of pro-fibrotic signaling pathways in reprogramming cells.
Figure 2:
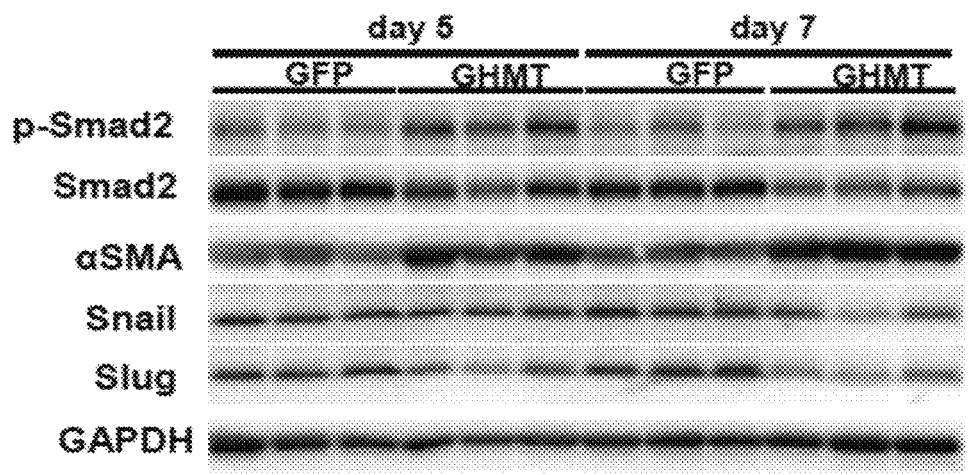
Figure 3:
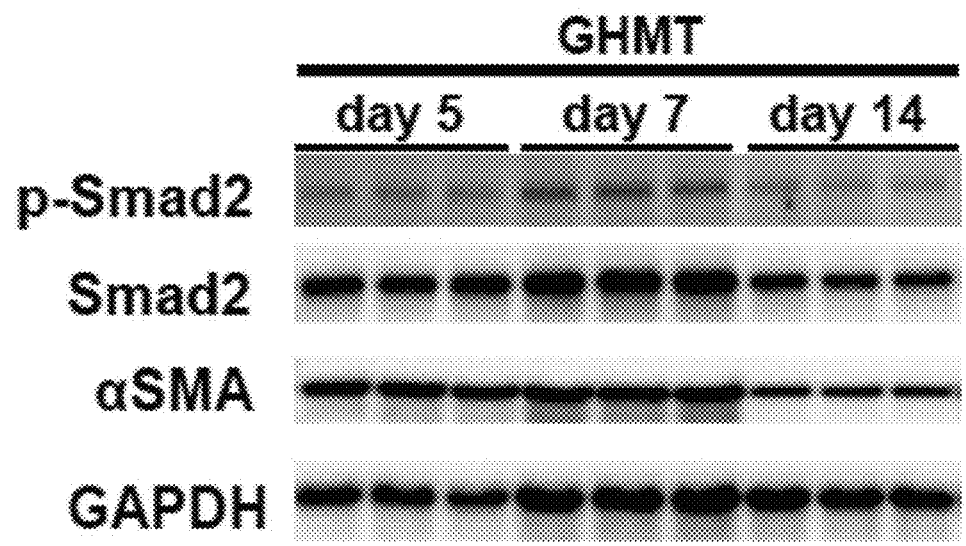
Figure 46:
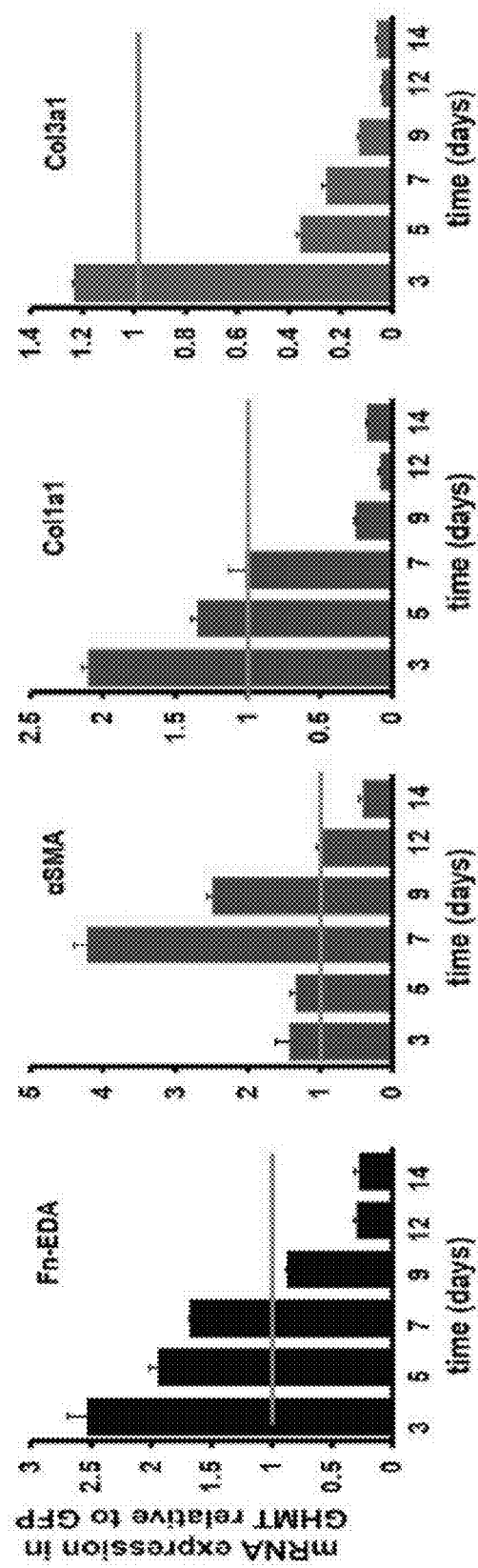
In FIGS. 46-48 the expression of TGF-β signaling components was analyzed at early stages of cardiac reprogramming.

To perform this testing, fibrotic markers in GHMT-infected MEFs were examined. Expression of ECM, such as Fn-EDA and Collagen I (Col1a1), was up-regulated after GHMT infection, but down-regulated 12 days post-infection (FIG. 1). The dynamic changes of αSMA expression were confirmed by immunoblotting (FIGS. 2-3). By day 14, expression of fibrotic genes in GHMT-infected cultures was approximately 50% of that in GFP-infected MEFs (FIG. 46). These data suggest that genes involved in fibrotic events are enhanced in GHMT-infected cells during the first week post-infection; however, the enhancement decreases after 12 days.

Figure 47:
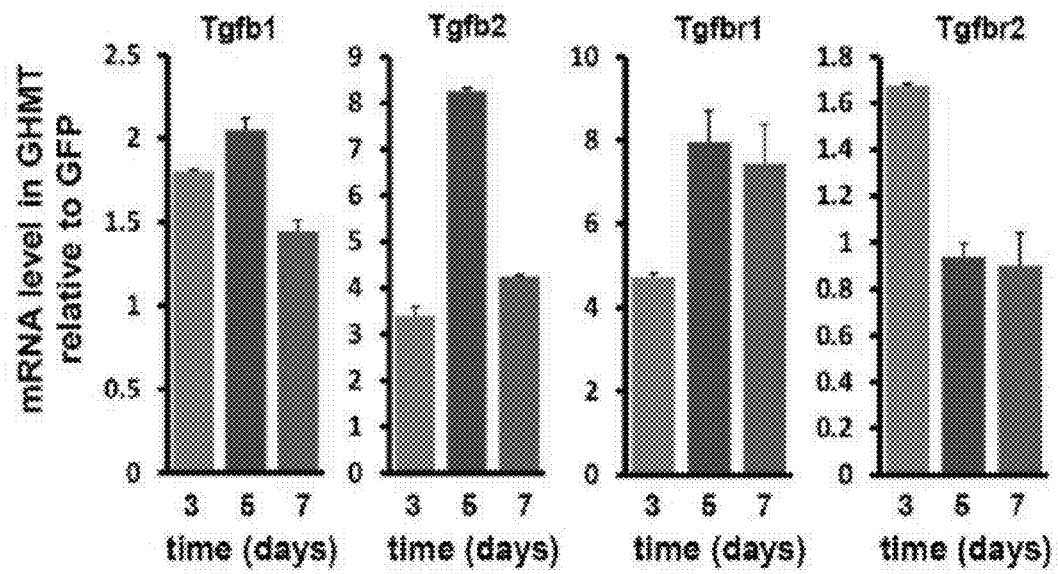
Figure 48:
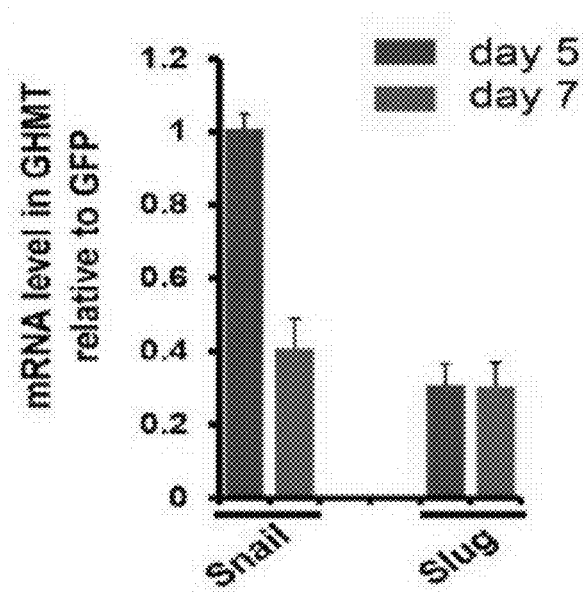

TGF-β signaling is an important pathway controlling fibrotic events. [Tomasek, J. J., et al., Nat. Rev. Mol. Cell Biol. 3, 349-63 (2002); Davis, J., & Molkentin, J. D., J. Mol. Cell Cardiol. 70, 9-18 (2014); Weber, K. T., Sun, Y., et al., Nat. Rev. Cardiol. 10, 15-26 (2013)] TGF-β family cytokines, such as TGF-β1/2, bind to type I and type II TGF-β receptors (Tgfbr1 and Tgfbr2), and activate target gene expression by phosphorylating Smad transcription factors, Smad2 and Smad3. [ten Dijke, P, & Arthur, H. M., Nat. Rev. Mol. Cell Biol. 8, 857-69 (2007)] To address whether increasing ECM expression during the early stages of reprogramming correlates with the activation of TGF-β signaling, the active form of Smad2 was analyzed with a phospho-specific antibody. Compared to GFP infected fibroblasts, higher levels of phospho-Smad2 were detected in GHMT infected cultures at day 5 and day 7 (FIG. 2). However, phospho-Smad2 and αSMA in GHMT MEFs were down-regulated at day 14, compared to days 5 and 7 (FIG. 3). In addition, expression of TGF-β signaling components, Tgfbr1 and Tgfb2, was significantly up-regulated in GHMT-cultures at days, 3, 5, and 7 (FIG. 47). In addition to SMADs, TGF-β signaling regulates downstream targets such as Snail and Slug transcription factors-38. Over-expression of GHMT down-regulated Snail by day 7 and Slug by day 5, at both the protein and mRNA level (FIG. 2 and FIG. 48). Taken together, these data indicate that TGF-β signaling and ECM expression are activated in GHMT-infected fibroblasts during the early stages of reprogramming.

Figure 49:
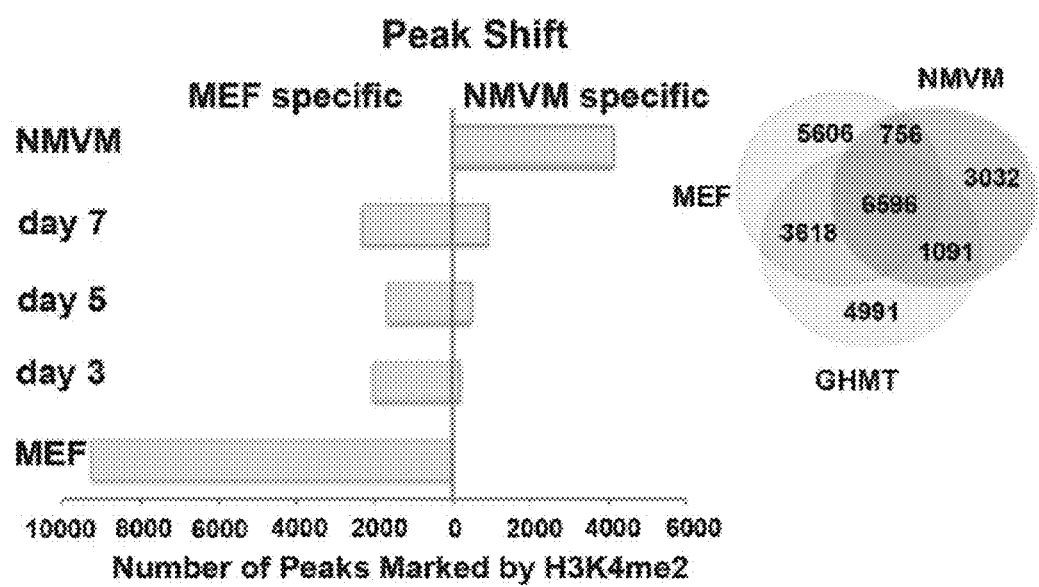
FIGS. 49-50: Active H3K4me2 marks the cluster of miR-133a-1 and miR-1-2 during early induction of reprogramming factors.

Example 2—H3K4 Dimethylation Marks the Locus of miR-1-2 and miR-133a-1 During Early Stages of GHMT-Mediated Reprogramming Studies on chromatin remodeling and histone modifications have led to improved reprogramming of fibroblasts into iPS cells. [Mikkelsen, T. S. et al., Nature 454, 49-55 (2008)] To gain insights into global genome changes, chromatin immunoprecipitation followed by deep sequencing (ChIP-Seq) was performed to mark H3K4 dimethylation (H3K4me2) in GHMT-infected MEFs. H3K4me2 marks both promoter and enhancer regions of active genes. [Koche, R. P. et al., Cell Stem Cell 8, 96-105 (2011)] H3K4me2 peaks shifted from a fibroblast toward a cardiomyocyte state post-expression of GHMT (FIG. 49). At day 7, 47% of a total of 16,296 H3K4me2 peaks identified in GHMT-expressing cultures were shared with peaks from primary cardiomyocytes. These shifts indicate cardiomyocyte identity caused by GHMT and suggest that expression of GHMT at early stages promotes chromatin changes required for cardiac reprogramming.

Figure 50:
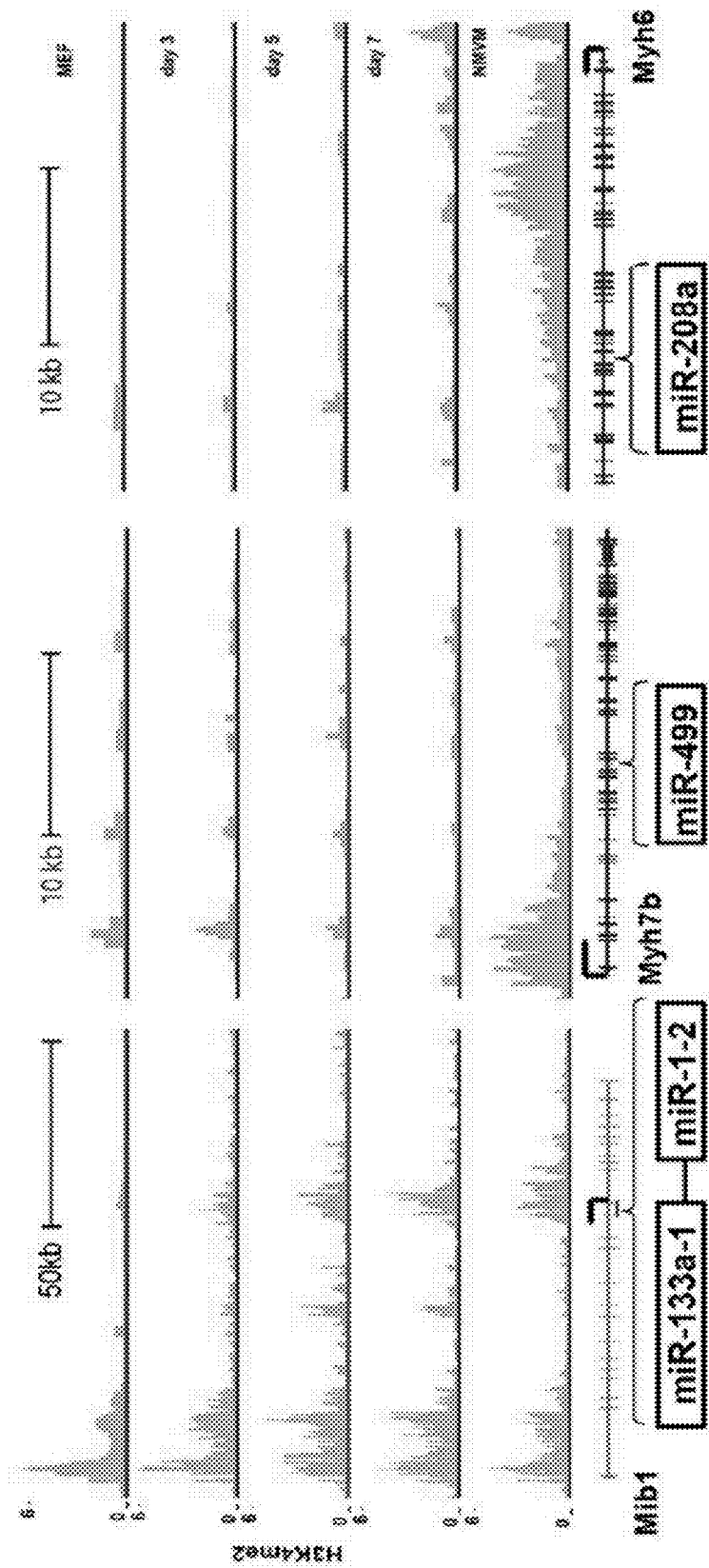

The muscle-specific microRNAs, miR-1 and miR-133, are regulators of skeletal and cardiac muscle cell differentiations. H3K4me2 levels at the miR-1-2/miR-133a-1 locus increased 3 days post GHMT infection and increased in magnitude with time (FIG. 50). Enhancers about 2 kb upstream of the miR-1-2/133a-1 cluster control expression of these two microRNAs in muscle cells. Thus, H3K4me2 peaks identified in GHMT-infected fibroblasts mark promoters and enhancers of the miR-1-2/133a-1 cluster, indicating activation of these two microRNAs. H3K4me2 peaks did not significantly increase at regulatory regions for other muscle-specific microRNAs, including miR-208 and miR-499, highlighting the potential importance of miR-1 and miR-133 for cardiac reprogramming.

Example 3—miR-1 and miR-133 Enhance Cardiac Reprogramming

Figure 4:
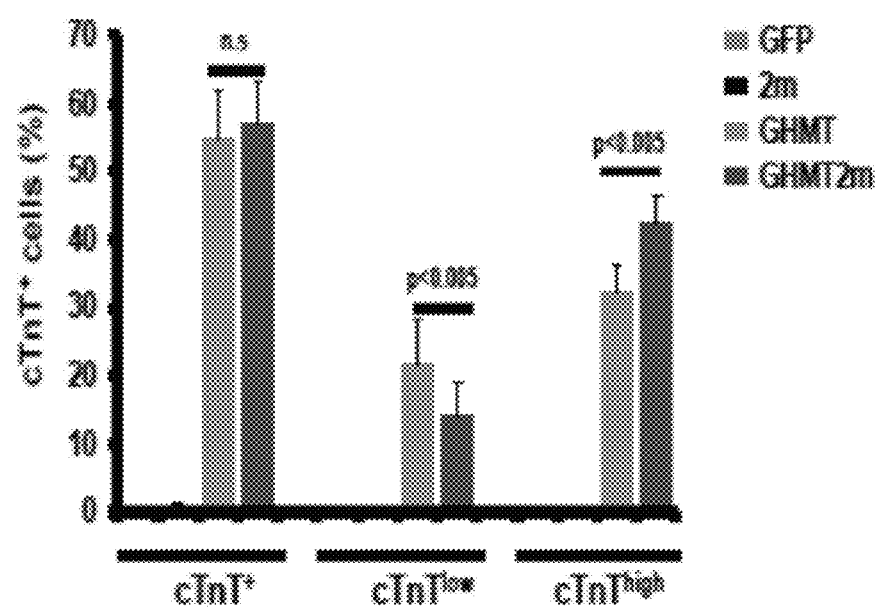
FIGS. 4-8: miR-1 and miR-133 enhance GHMT-mediated cardiac reprogramming.
Figure 5:
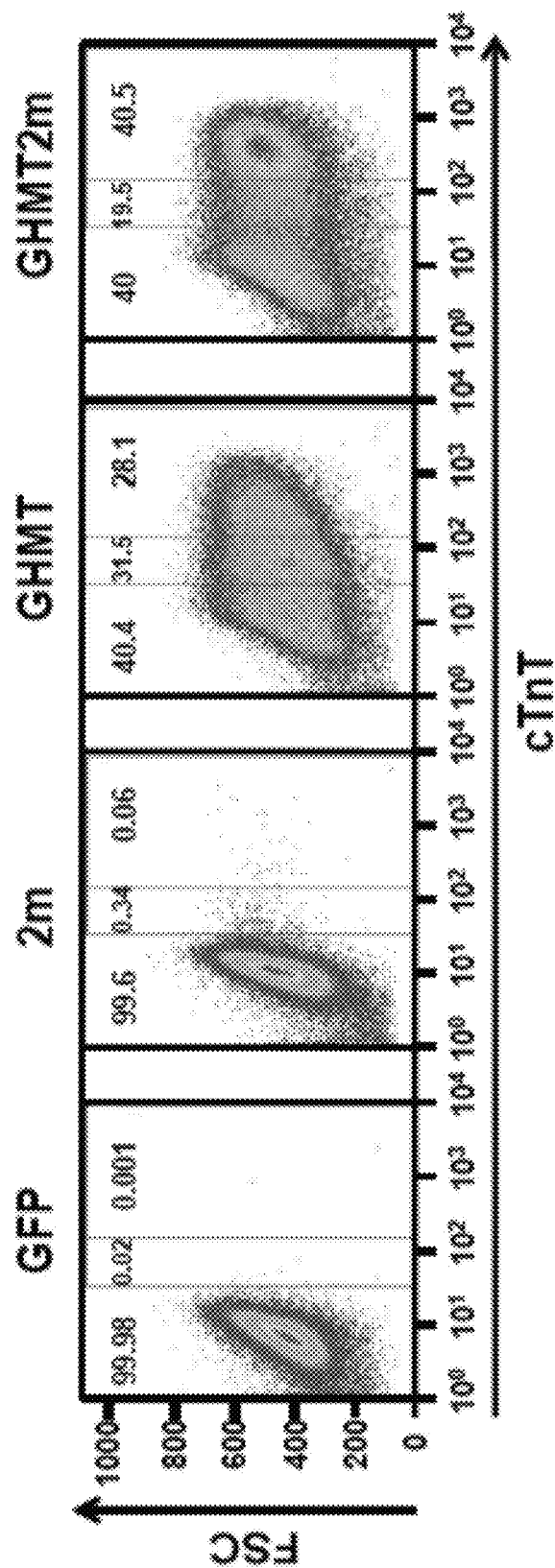

To determine whether miR-1 and miR-133 are able to enhance reprogramming, expression of cTnT by flow cytometry 7 days post-infection with retroviruses carrying GHMT and/or the microRNAs was examined. GHMT-induced expression of cTnT in about 54% of MEFs (FIGS. 4 and 5). The cTnT+ cells were divided into two classes, $cTnT^{low}$ and $cTnT^{high}$. When miR-1 and miR-133 (2 m) were delivered alone, less than 1% of cells became positive for cTnT. However, adding 2 m into GHMT (GHMT2m) significantly increased the $cTnT^{high}$ fraction from about 32% to about 42% (FIGS. 4 and 5). Next, the effects of 2 m on the assembly of sarcomeres was examined.

Figure 6:
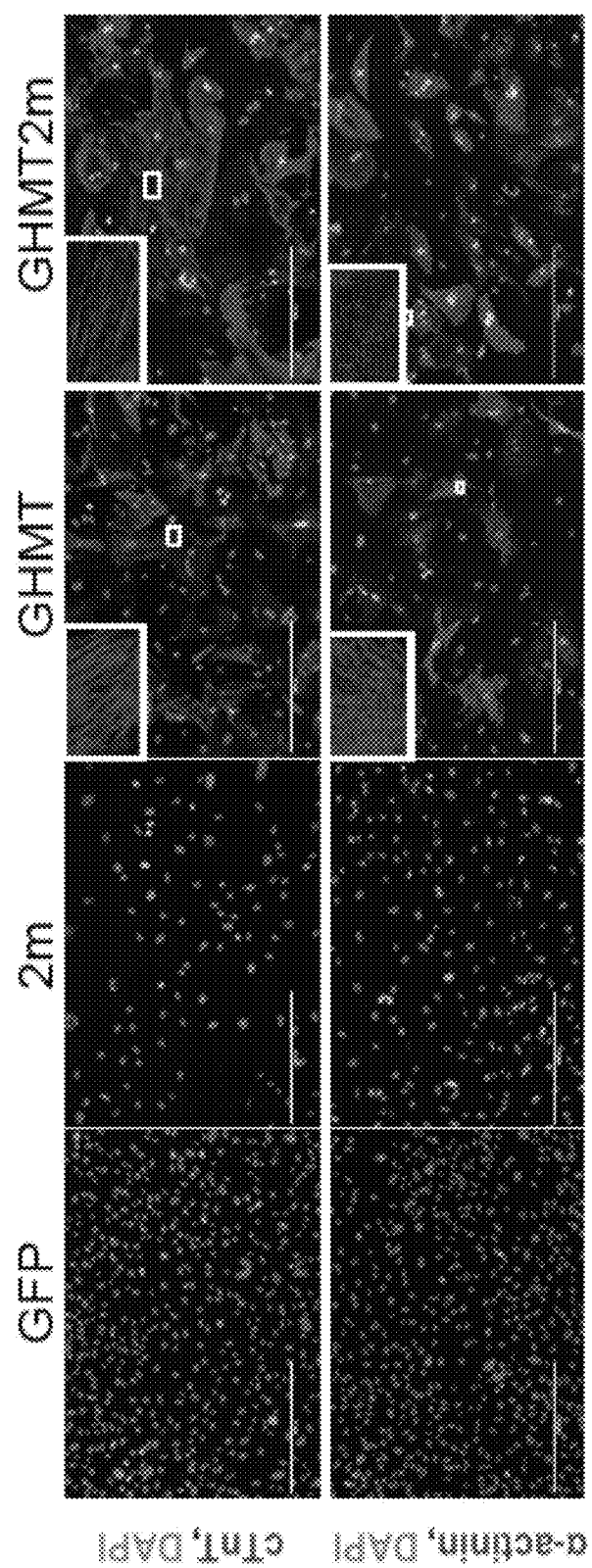
Figure 51:
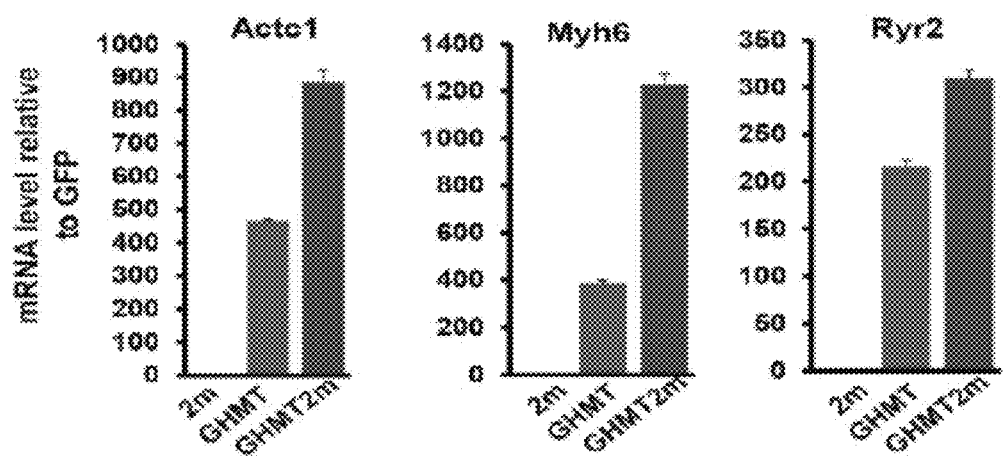
FIGS. 51-53: miR-1 and miR-133 enhance cardiac reprogramming.

Immunocytochemistry was performed with antibodies against cTnT and another sarcomeric protein, α-actinin. Two weeks post-infection, GHMT produced cells with strong immunostaining of α-actinin and cTnT (FIG. 6). More iCMs were observed in GHMT2m-infected cultures (FIG. 7), and expression of cardiomyocyte genes such as ACTC1, Myh6 and RyR2, was also enhanced by 2 m (FIG. 51). These data indicate that miR-1 and miR-133 promote expression of cardiac genes and assembly of sarcomeres.

Figure 52:
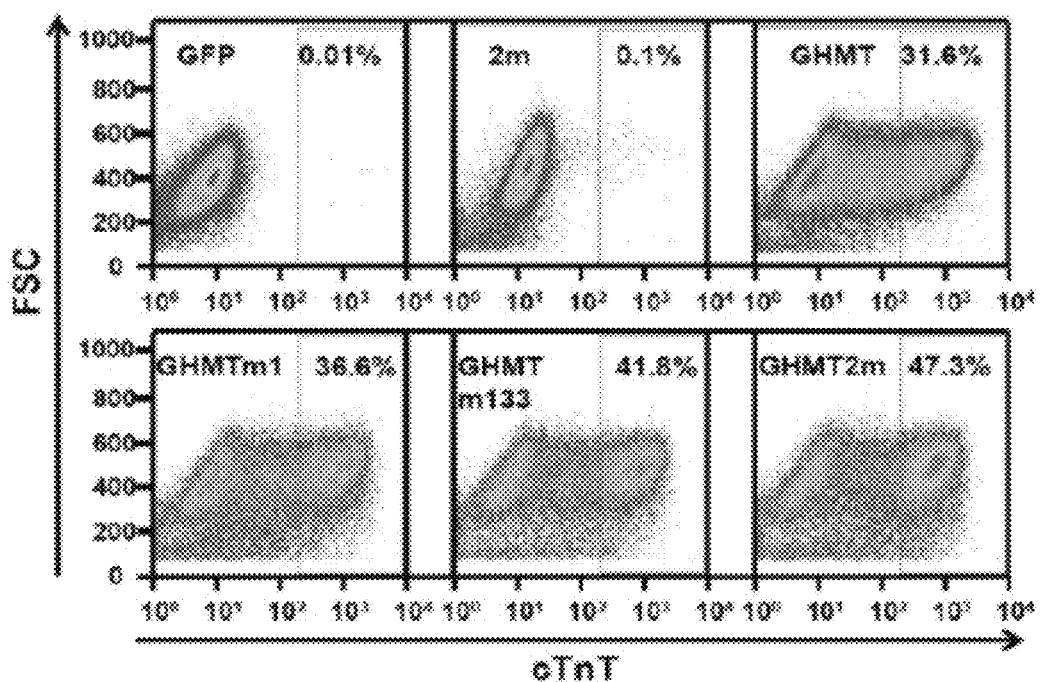
Figure 53:
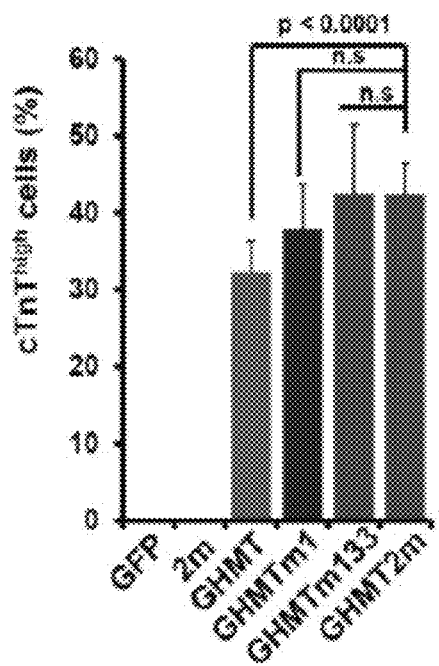
Figure 54:
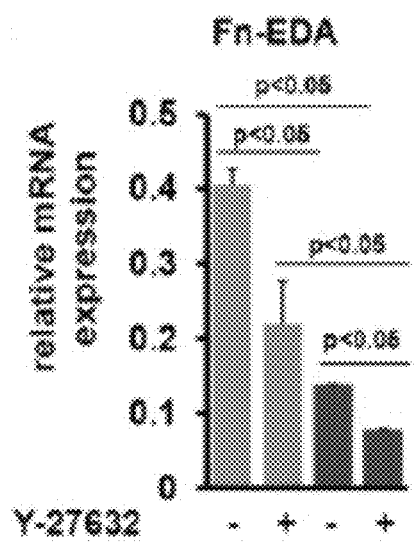
FIGS. 54-57: Y-27632 decreases Profibrotic gene expression and enhances cardiac reprogramming.
Figure 55:
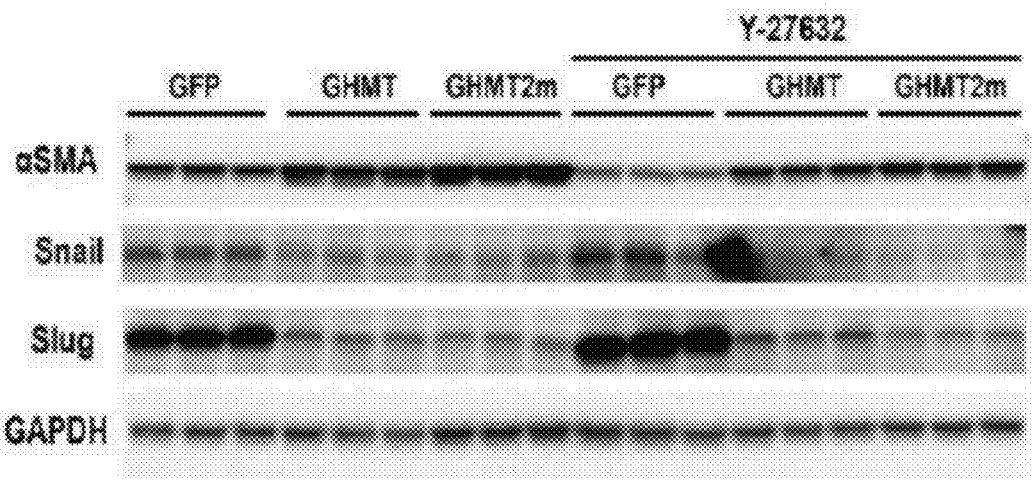
Figure 56:
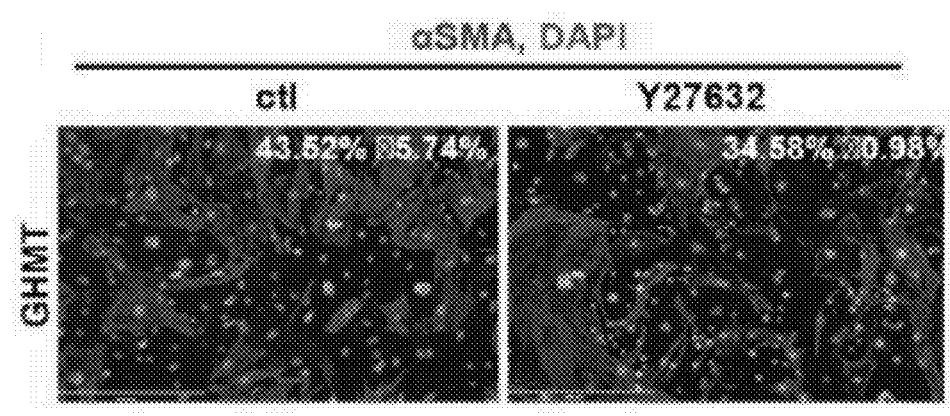

Experiments were performed to assess the relative impact of miR-1 and miR-133 for enhancing GHMT-mediated reprogramming. Depletion of either miR-1 or miR-133 from GHMT2m did not significantly reduce the percentage of $cTnT^{high}$ cells in cultures (FIGS. 52 and 53), suggesting that either miR-1 or miR-133 is sufficient to enhance expression of cTnT.

Figure 7:
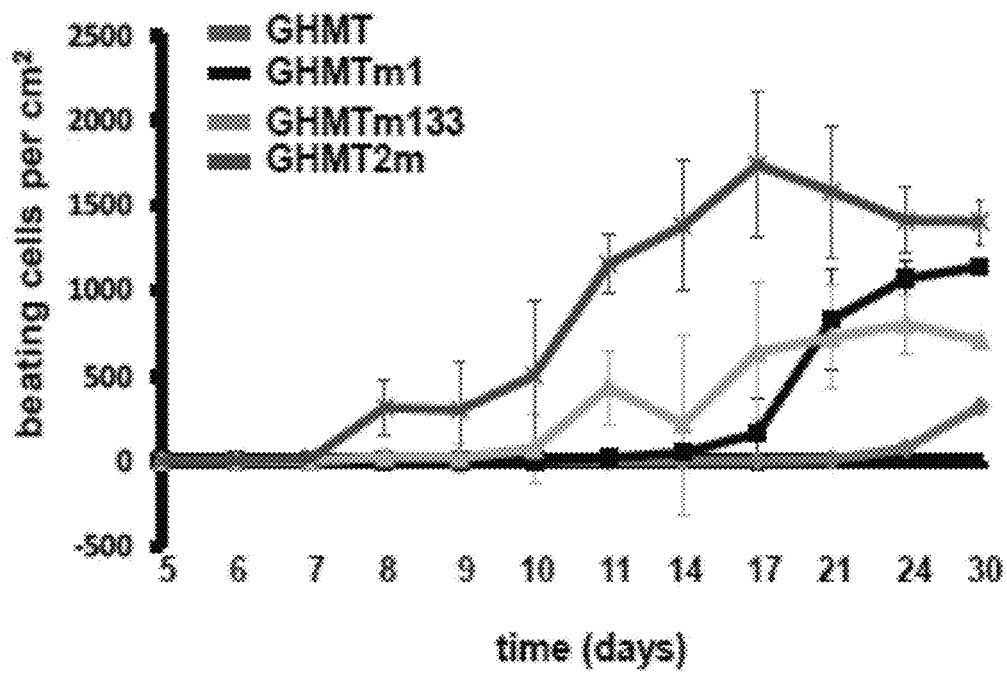
Figure 8:
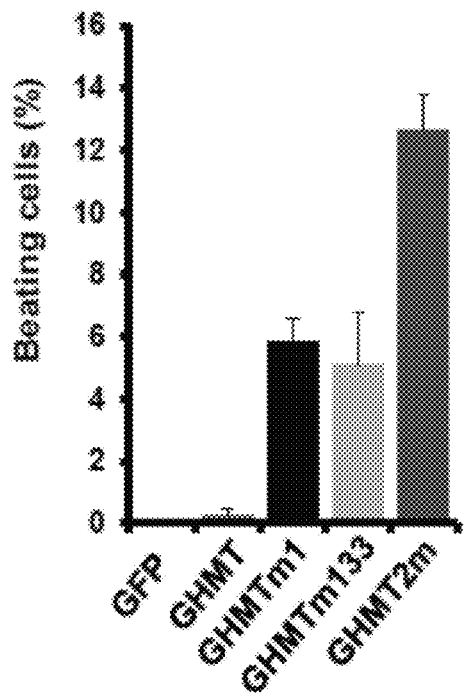

Next, spontaneously beating cells were examined. GHMT produced iCMs that started to beat by 3 weeks. GHMT plus miR-1 (GHMTm1) or GHMT plus miR-133 (GHMTm133) produced iCMs that started to beat by 2 weeks and GHMT2m produced iCMs that began beating by 8 days (FIG. 7). More beating iCMs were observed in GHMT2m-infected cultures than with the other conditions (FIG. 7). By 4 weeks, GHMT, GHMTm1, GHMTm133, and GHMT2m produced about 200, about 1100, about 700, and about 1400 beating iCMs per cm$^2$, respectively (FIG. 7). At day 25, GHMT2m induced approximately 12% of cultures to spontaneously contract, which is more than beating fractions induced by GHMT, GHMTm1 or GHMTm133 (FIG. 8). The data suggest that both miR-1 and miR-133 are required for generating maximal beating iCMs in GHMT-infected cultures.

To globally examine effect of miR-1 and miR-133 on gene expression, RNA-Seq was performed for gene expression profiling in GHMT- and GHMT2m-infected MEFs at day 7. Many cardiac ontologies are enriched among genes up-regulated in GHMT2m-infected cultures, whereas ECM ontologies are enriched among genes down-regulated in GHMT2m-infected cultures (Table 2). These data indicate that miR-1 and miR-133 enhance cardiac gene expression, but inhibit fibrotic gene expression.

TABLE 2

RNA-Seq analysis of MEFs infected with GHMT or GHMT2m at day 7.

| Genes | | GO Description | Enrichment Score | P-value |
|---|---|---|---|---|
| Up in GHMT2m | Cardiac Development | Contractile fiber part | 26.23 | 4.07E−12 |
| | | Muscle system process | 20.05 | 1.95E−09 |
| | | Regulation of heart contraction | 19.81 | 2.48E−09 |
| | | Myofibril assembly | 19.22 | 4.52E−09 |
| | | Muscle contraction | 17.51 | 2.49E−08 |
| | | Voltage-gated cation channel activity | 16.33 | 8.07E−08 |
| | | Striated muscle contraction | 15.91 | 1.23E−07 |
| | | Muscle structure development | 15.79 | 1.39E−07 |
| | | Voltage-gated channel activity | 14.13 | 7.29E−07 |
| | | Cardiac muscle contraction | 13.54 | 1.31E−06 |
| | | Calcium channel complex | 13.54 | 1.31E−06 |
| | | Cardiac muscle cell development | 12.29 | 4.60E−06 |
| | | Cardiac myofibril assembly | 12.22 | 4.94E−06 |
| | | Cardiac muscle fiber development | 10.04 | 4.35E−05 |
| | | Voltage-gated calcium channel complex | 9.27 | 9.40E−05 |
| | | Voltage-gated potassium channel activity | 9.04 | 1.19E−04 |
| | | Cardiac muscle tissue morphogenesis | 8.91 | 1.34E−04 |
| | | Heart development | 8.64 | 1.77E−04 |
| Down in GHMT2m | Fibrotic Events | Extracellular region | 7.23 | 7.24E−04 |
| | | Extracellular matrix | 6.94 | 9.70E−04 |
| | | Proteinaceous extracellular matrix | 6.6 | 1.36E−03 |
| | | Extracellular region part | 6.07 | 2.23E−03 |

RNA-Seq analysis of MEFs infected with GHMT or GHMT2m at day 7. Genes up-regulated ≥1.5 folds or down-regulated ≤0.5 folds in GHMT2m were used for gene ontology analysis.

Figure 9:
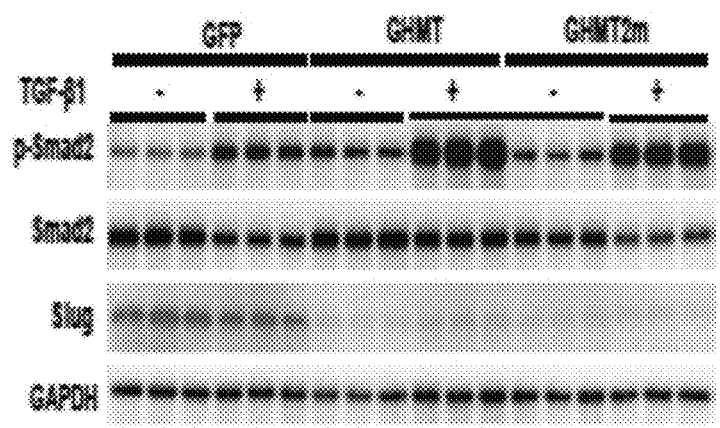
FIGS. 9-17: Stimulation of pro-fibrotic signaling by TGF-β1 inhibits cardiac reprogramming.
Figure 10:
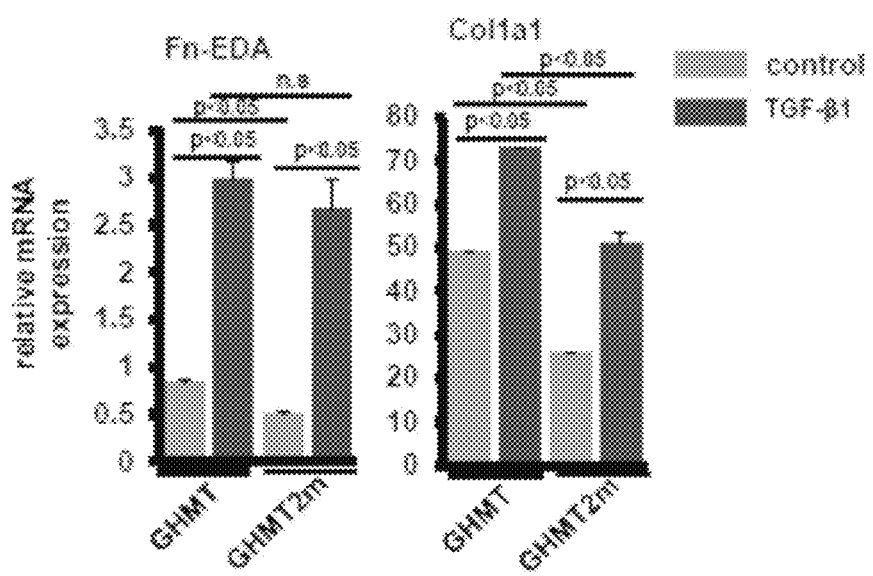
Figure 11:
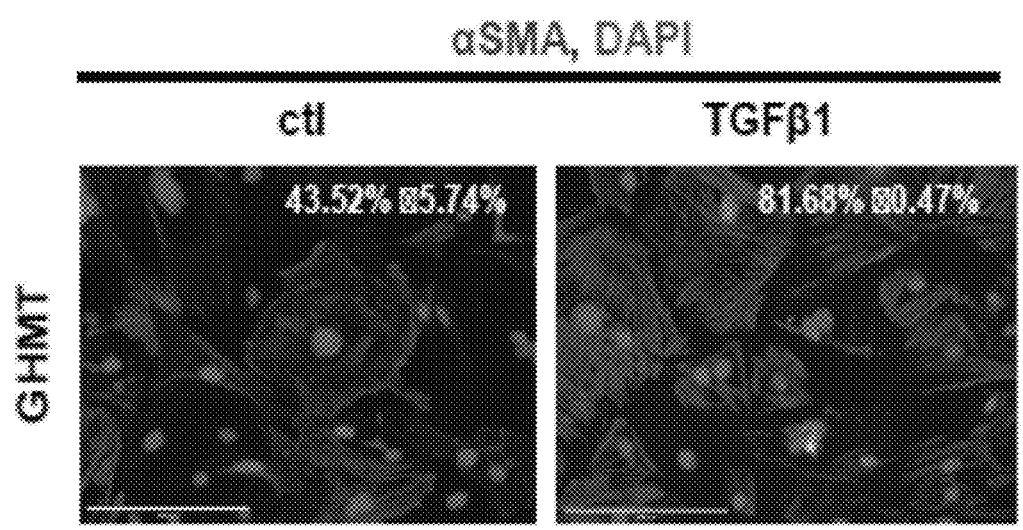

Example 4—Over-Activation of Pro-Fibrotic Signaling Inhibits Cardiac Reprogramming To assess whether pro-fibrotic signaling serves as a barrier to cardiac reprogramming, pro-fibrotic signaling was over-activated in reprogramming cells. Treatment of fibroblasts with TGF-β1 activates pro-fibrotic signaling cascades. TGF-β1 treatment increased the amount of phospho-Smad2, expression of Fn-EDA and Col1a1, and formation of αSMA stress fibers in GHMT-infected cultures at day 7, compared to non-treated cultures (FIGS. 9-11). This data suggests that TGF-β1 treatment over-activates pro-fibrotic signaling in GHMT-infected fibroblasts.

Addition of miR-1 and miR-133 (2 m) significantly down-regulated expression of Fn-EDA, Col1a1 in GHMT-infected cultures (FIG. 10). TGF-β1 treatment enhanced profibrotic gene Col1a1 expression in GHMT2m-fibroblasts; however, their levels were significantly less than that in GHMT-infected fibroblasts (FIG. 10). The data indicate that miR-1 and miR-133 suppress pro-fibrotic gene expression in GHMT-infected cells.

Figure 12:
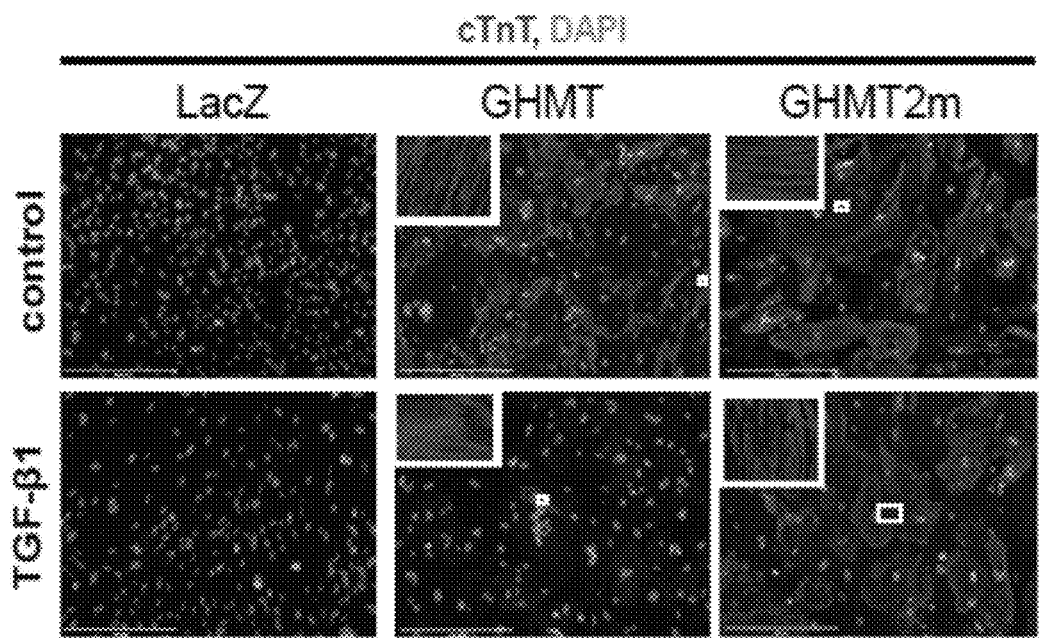
Figure 13:
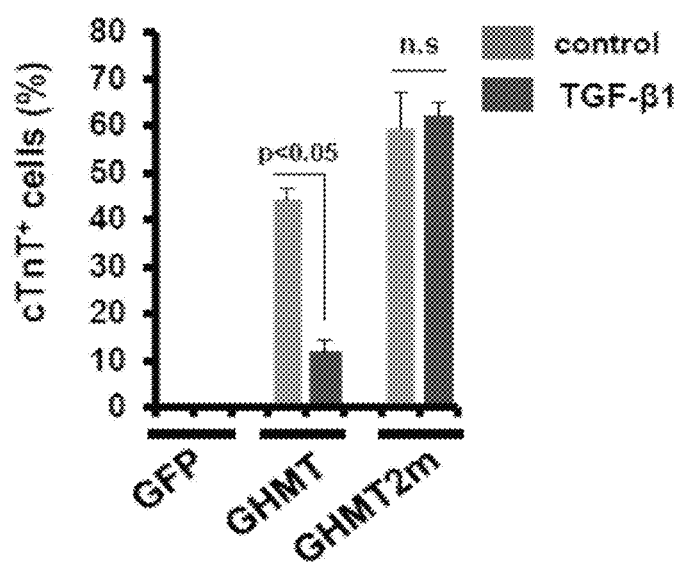
Figure 14:
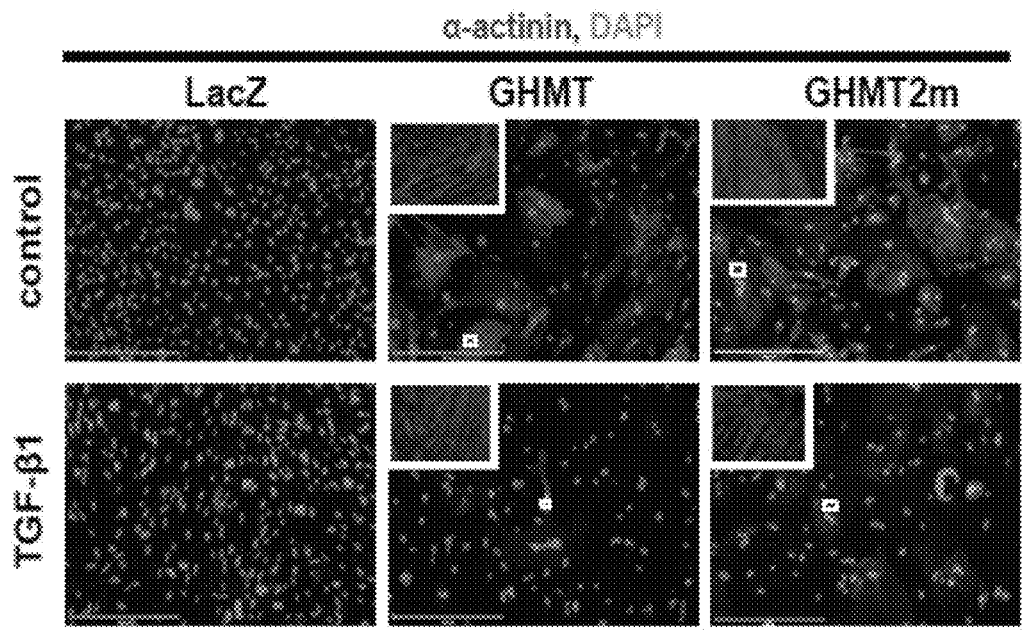
Figure 15:
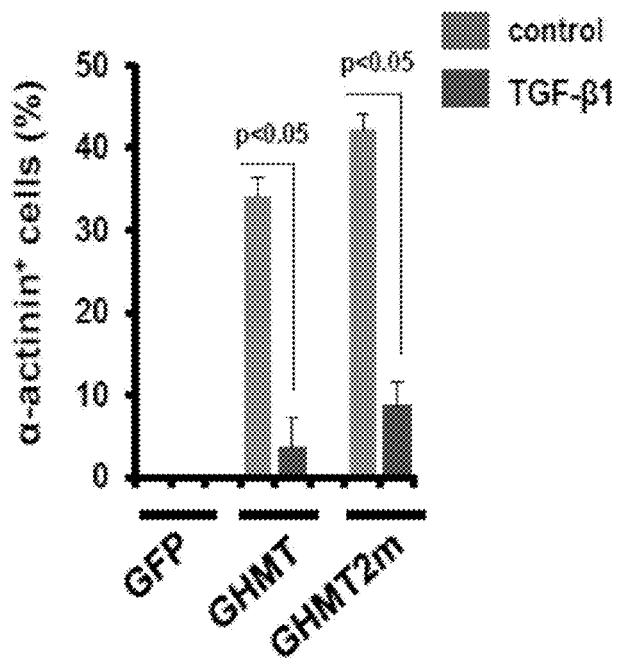
Figure 16:
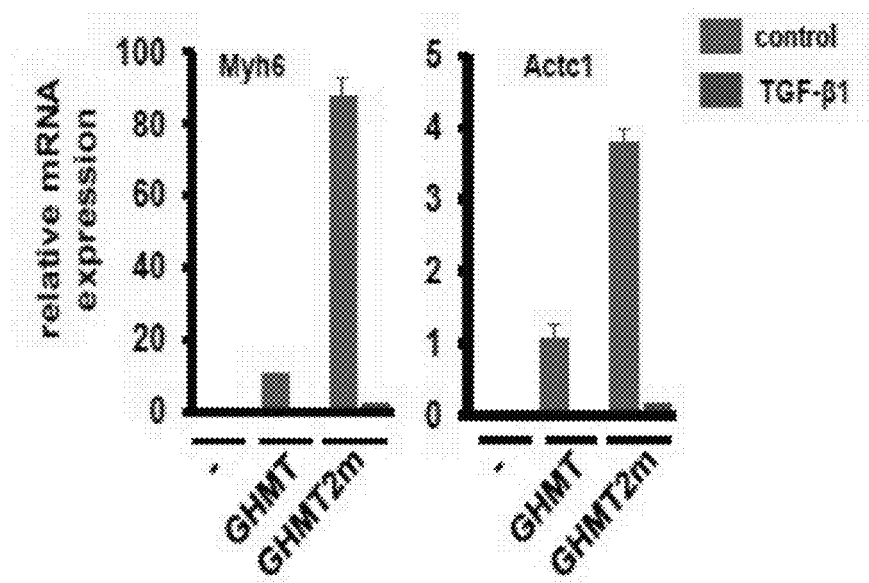

Next, over-activation of pro-fibrotic signaling in the suppression of cardiac reprogramming was investigated. GHMT induced approximately 29% of fibroblasts to be positive for cTnT$^{high}$ by day 7. Treatment of GHMT-infected cultures with TGF-β1 significantly reduced the cTnT$^{high}$ fraction to approximately 19%, the cTnT+ and α-actinin+ populations (FIGS. 12-15), and cardiac gene expression (FIG. 16). GHMT2m induced approximately 39% of fibroblasts to be positive for cTnT$^{high}$. Although, treatment with TGF-β1 did not significantly decrease the fraction of cTnT+ cells in GHMT2m-cultures at day 7 and day 14 (FIGS. 12 and 13), expression of other cardiomyocyte markers, including α-actinin, Myh6 and Actc1, was significantly down-regulated by treatment with this pro-fibrotic stimulus (FIGS. 14-16).

Figure 17:
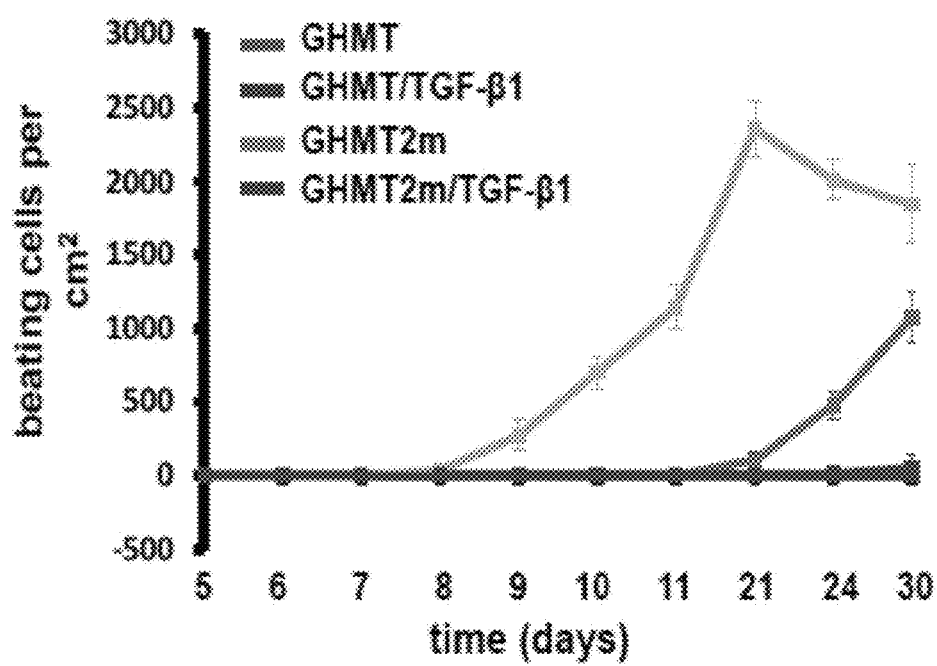
Figure 18:
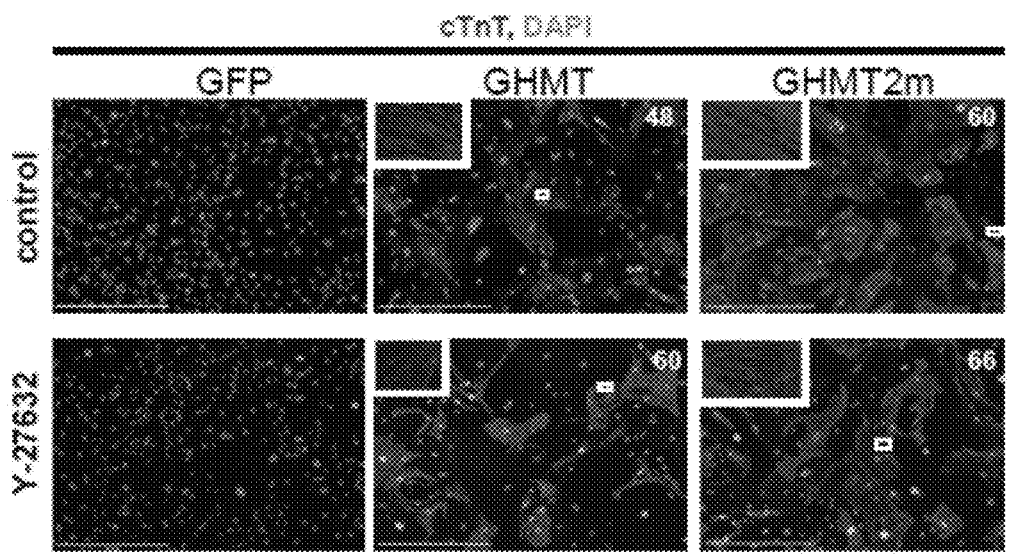
FIGS. 18-23: Inhibitors of TGF-β signaling decrease pro-fibrotic gene expression and enhance cardiac reprogramming.
Figure 19:
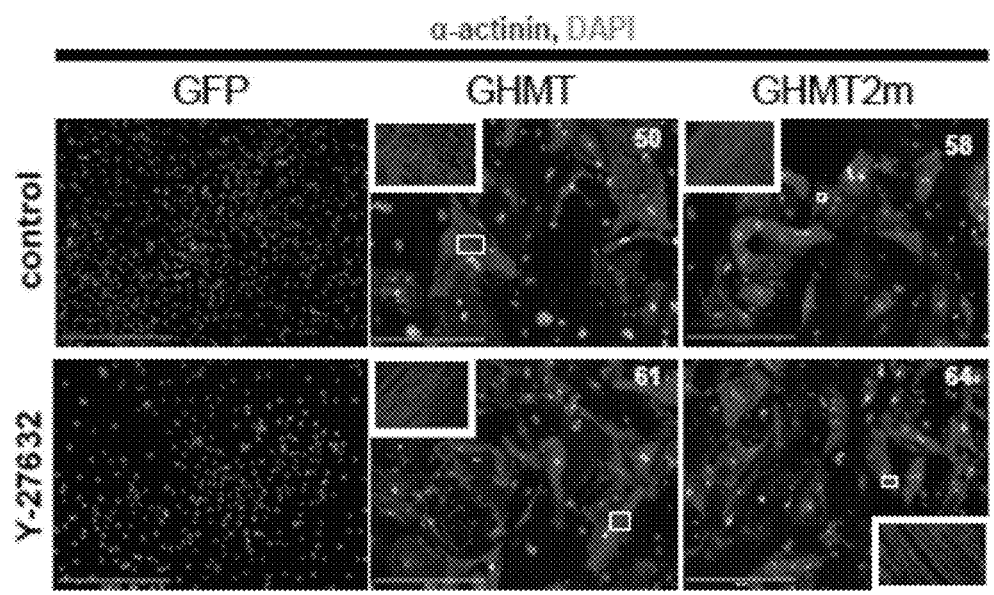

Next, the effect of TGF-β1 treatment on beating iCMs in GHMT- and GHMT2m-infected cultures was examined. GHMT produced about 200 beating cells per cm² by one month; however, this was completely abolished by TGF-β1 treatment (FIG. 17). By one month, GHMT2m produced about 1500 beating cells per cm². TGF-β1 treatment decreased beating cells in GHMT2m-infected cultures by 100-fold (FIG. 17). Taken together, these data demonstrate that over-activation of pro-fibrotic signaling attenuates GHMT-mediated reprogramming of fibroblast into beating iCMs, and two microRNAs enhance cardiac reprogramming at least in part, by attenuating pro-fibrotic gene expression.

Figure 24A:
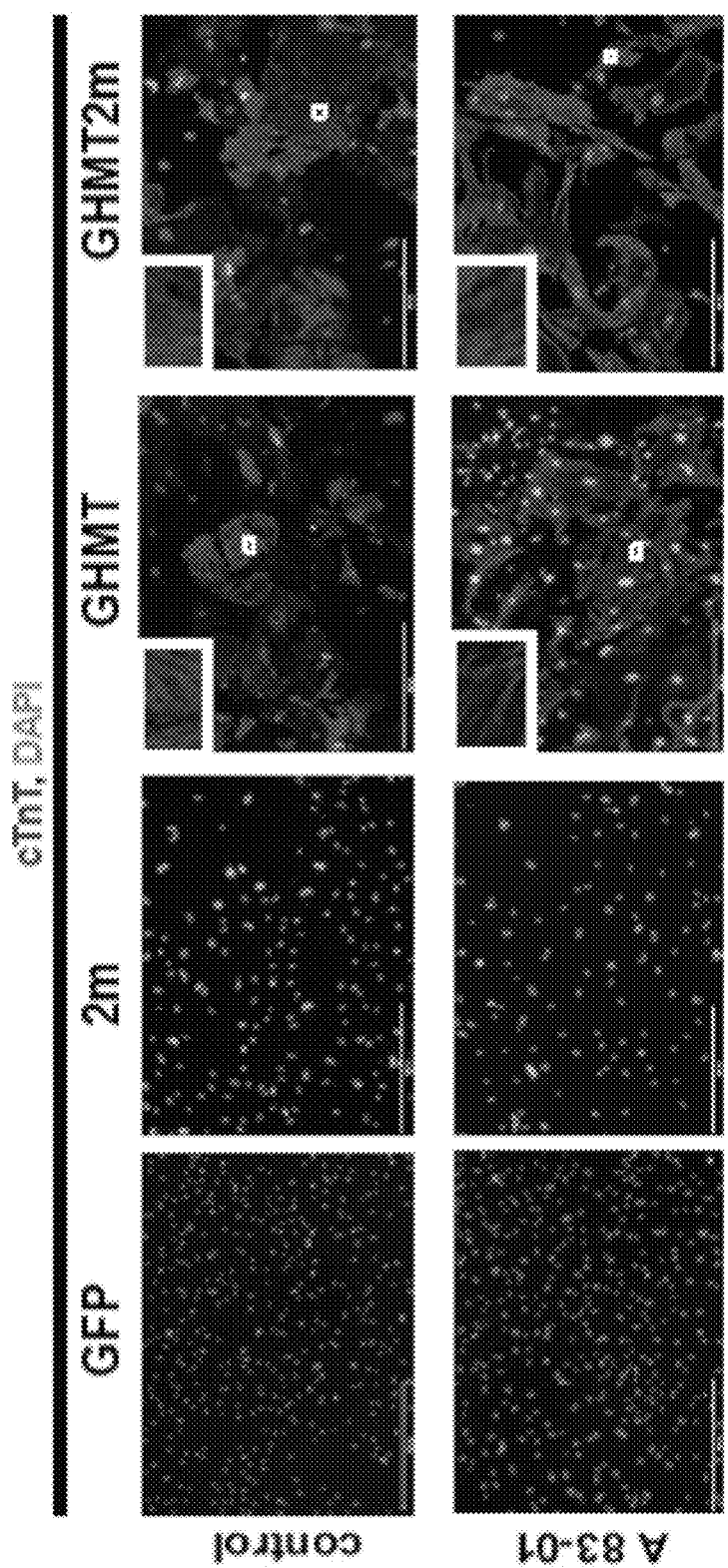
FIG. 24A is a set of six representative immunofluorescence images of MEFs stained for cTnT (red—appearing as larger, light gray objects in gray scale and only evident in the GHMT and GHMT2m samples) at day 14. White boxes are enlarged in insets. Scale bars, 400 μm.
Figure 24B:
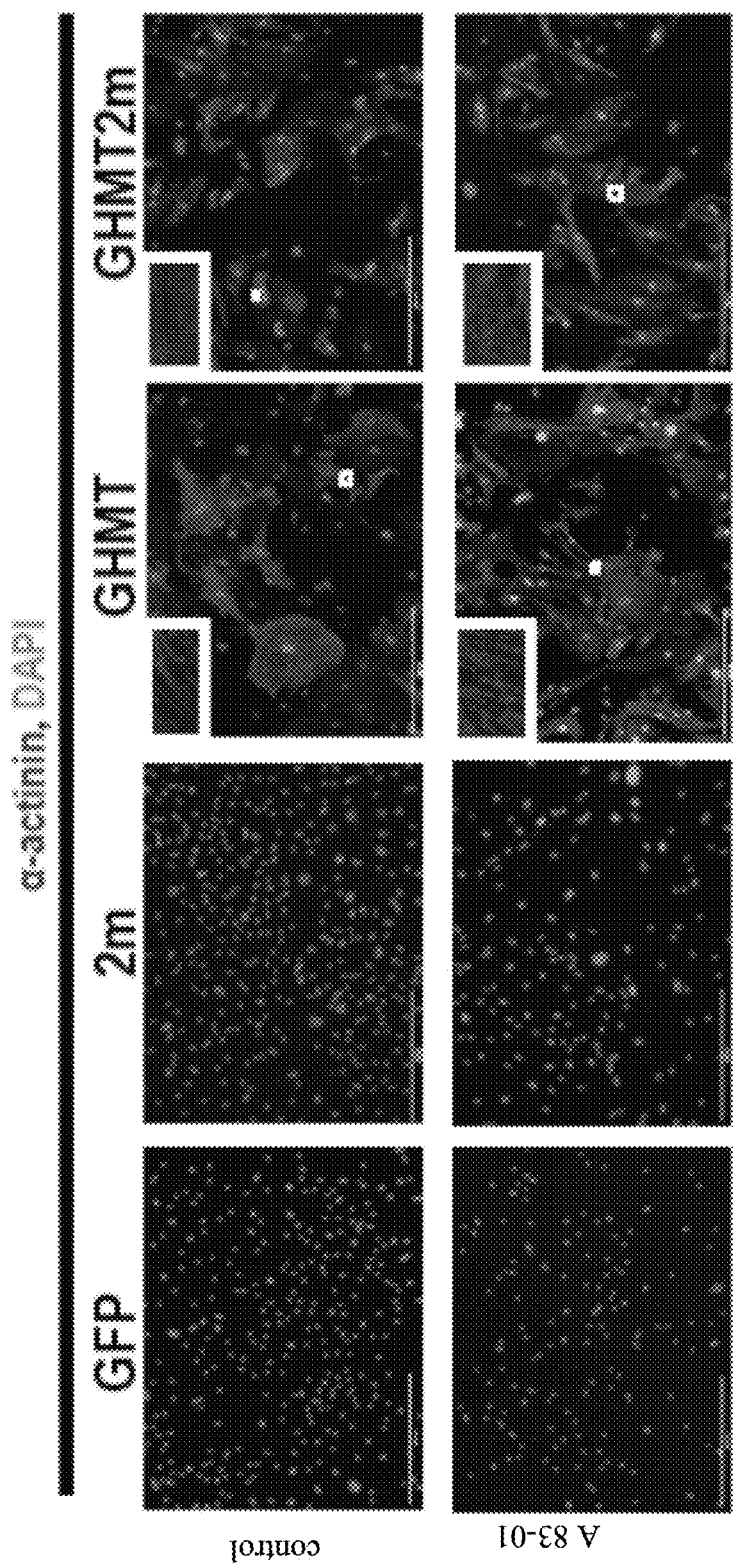
FIG. 24B is a set of six representative immunofluorescence images of MEFs stained for α-actinin (red—appearing as larger, light gray objects in gray scale and only evident in the GHMT and GHMT2m samples) at day 14. White boxes are enlarged in insets. Scale bars, 400 μm.
Figure 25:
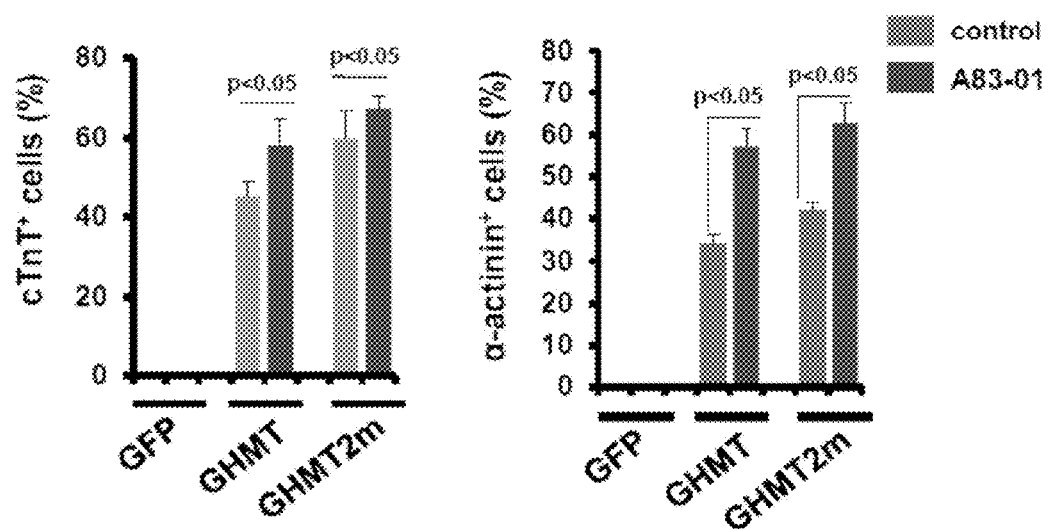
Figure 26:
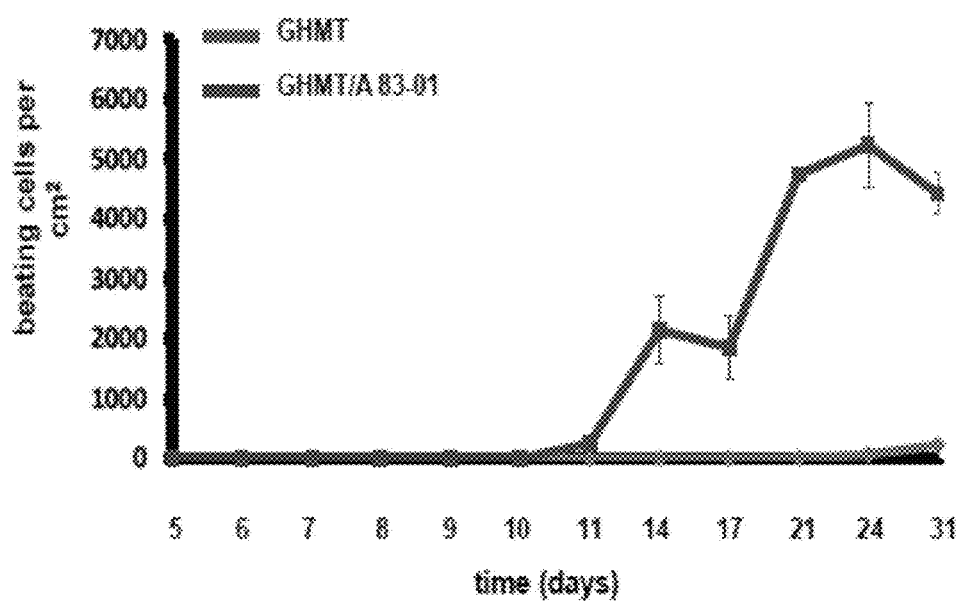

Example 5—ROCK Inhibitors Suppress Pro-Fibrotic Genes and Enhance Cardiac Reprogramming Inhibition of pro-fibrotic events was examined to assess whether this enhanced cardiac reprogramming. Pro-fibrotic events can be governed by RhoA-ROCK (Rho-associated protein kinase). In response to increased mechanical tension, RhoA triggers the formation of stress fibers and stimulates pro-fibrotic events via activation of its downstream effector, ROCK. Inhibition of RhoA-ROCK signaling was examined to see if it would also enhance cardiac reprogramming. The ROCK inhibitor Y-27632 decreased expression of Fn-EDA and αSMA, but did not change Snail and Slug expression in GFP-, GHMT- and GHMT2m-infected cultures (FIGS. 24-26). The data suggest that Y-27632 suppresses pro-fibrotic genes in reprogramming cells.

Figure 20:
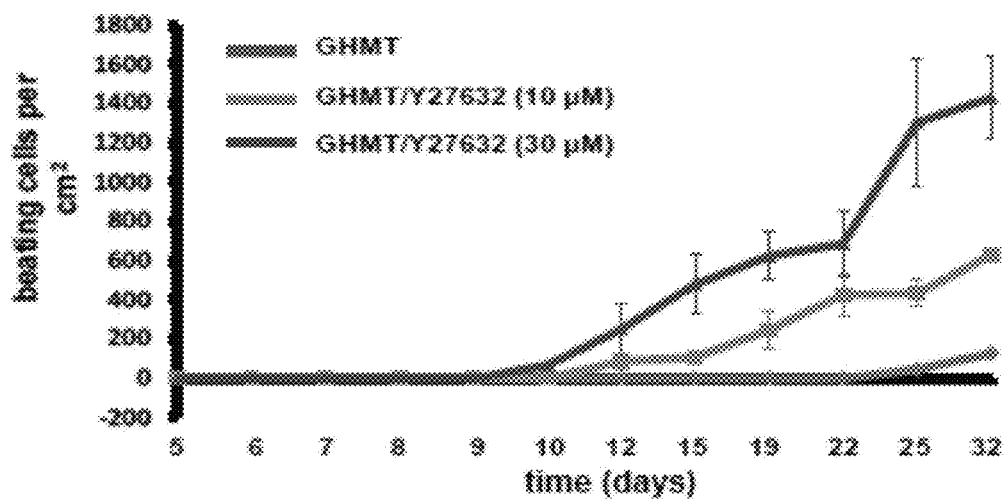
Figure 21:
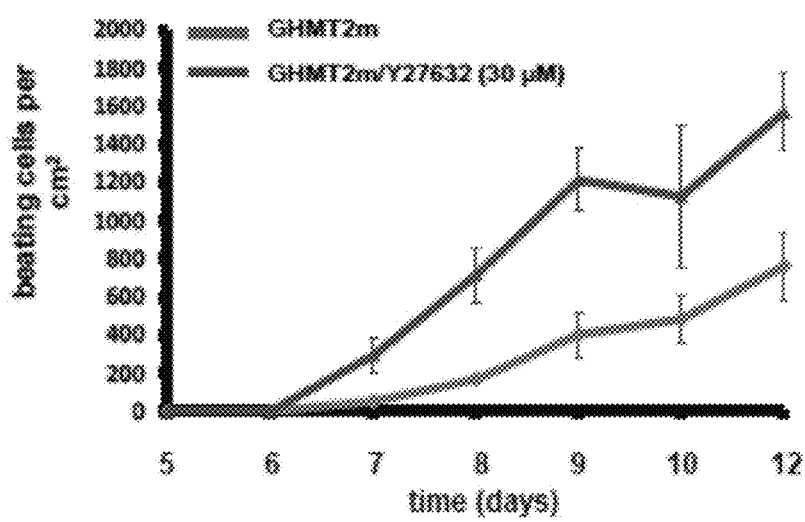
Figure 22:
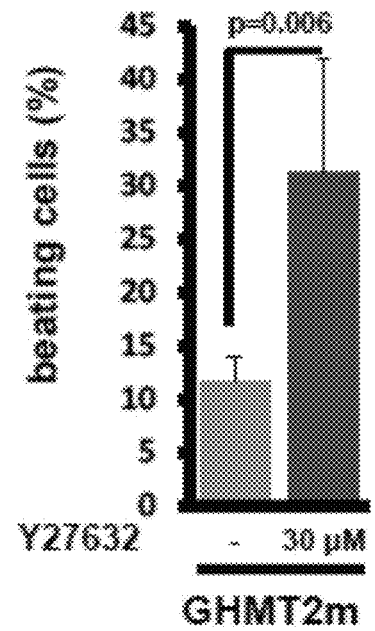
Figure 57:
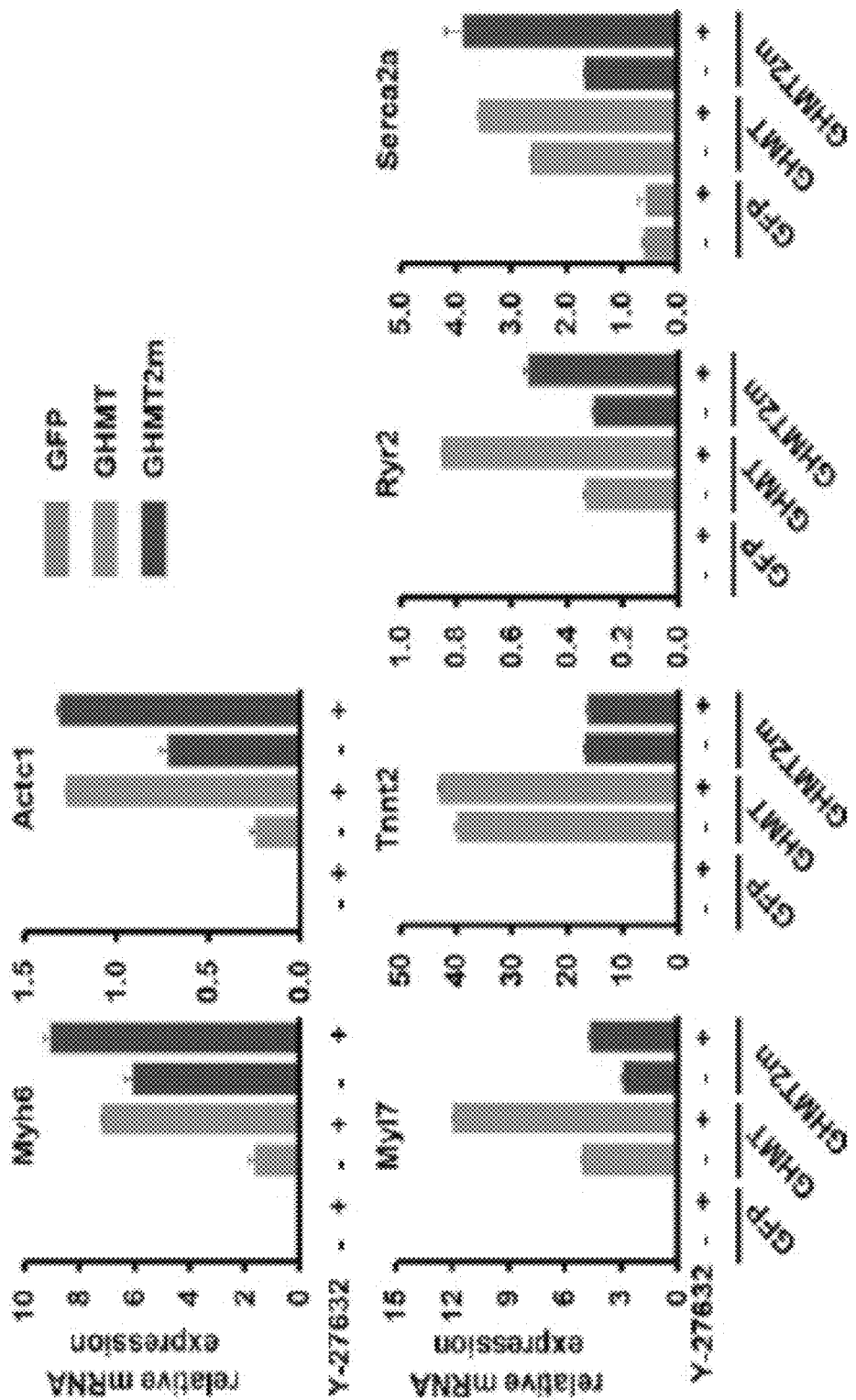

Next, the effect of Y-27632 on cardiac reprogramming was examined. Y-27632 treatment enhanced assembly of myocyte sarcomeres (FIGS. 51 and 52), and cardiomyocyte-specific gene expression (FIG. 57). As described previously, GHMT induced about 200 beating cells per cm² by 4 weeks. Adding Y-27632 (30 μM) produced contracting cells by 12 days, and increased the number of beating cells by 7-fold by 4 weeks (FIG. 20). By day 8, GHMT2m produced about 160 beating cells per cm², and GHMT2m plus Y-27632 induced about 700 beating cells per cm² (FIG. 21). By day 12, Y-27632 treatment increased beating cell population from about 10% to about ~30% in GHMT2m cultures (FIG. 22).

Figure 23:
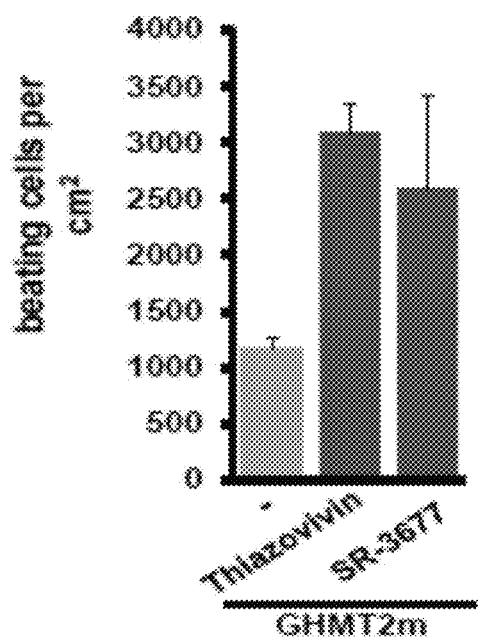

To exclude the possibility of Y27632 off-target effects, additional ROCK inhibitors were tested. Other ROCK inhibitors, including Thiazovivin [Xu, Y. et al., *Proc. Natl. Acad. Sci. U.S.A* 107, 8129-34 (2010)] and SR-3677 [Feng, Y. et al., *J. Med. Chem.* 51, 6642-5 (2008)], also enhanced cardiac reprogramming and promoted formation of spontaneously beating cells (FIG. 23). Taken together, these results indicate that small molecules that inhibit pro-fibrotic genes by targeting RhoA-ROCK signaling significantly enhance reprogramming of MEFs into beating iCMs.

Figure 58:
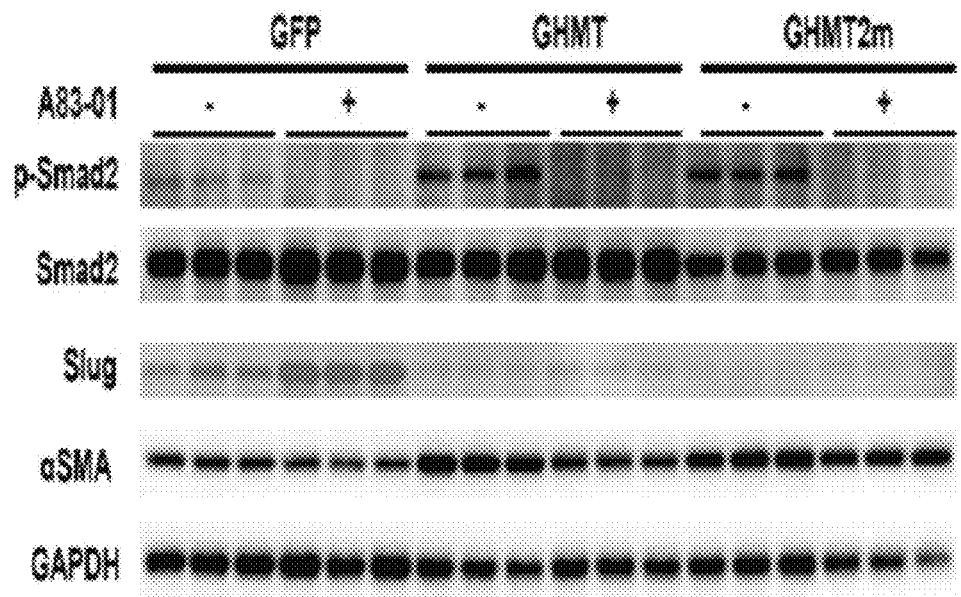
FIGS. 58-61: A83-01 enhances cardiac reprogramming.
Figure 59:
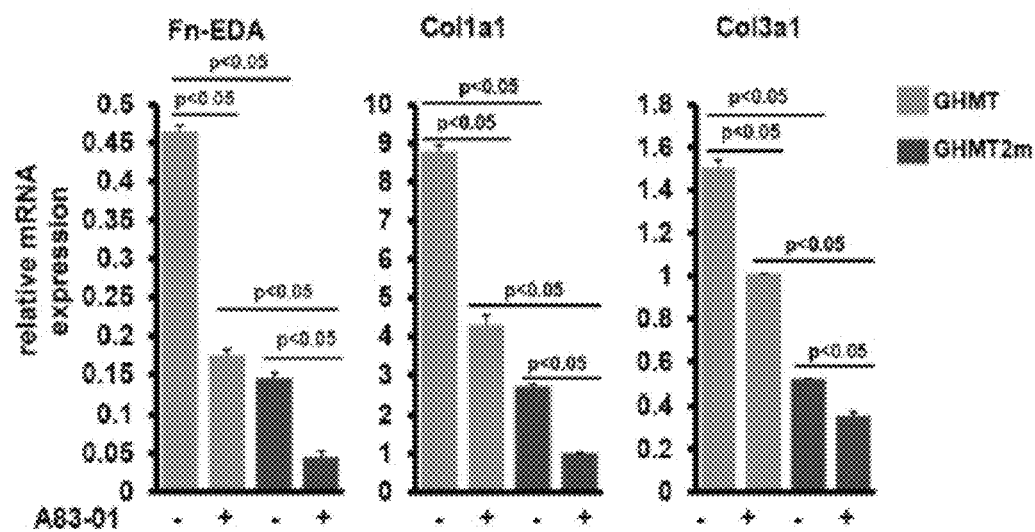
Figure 60:
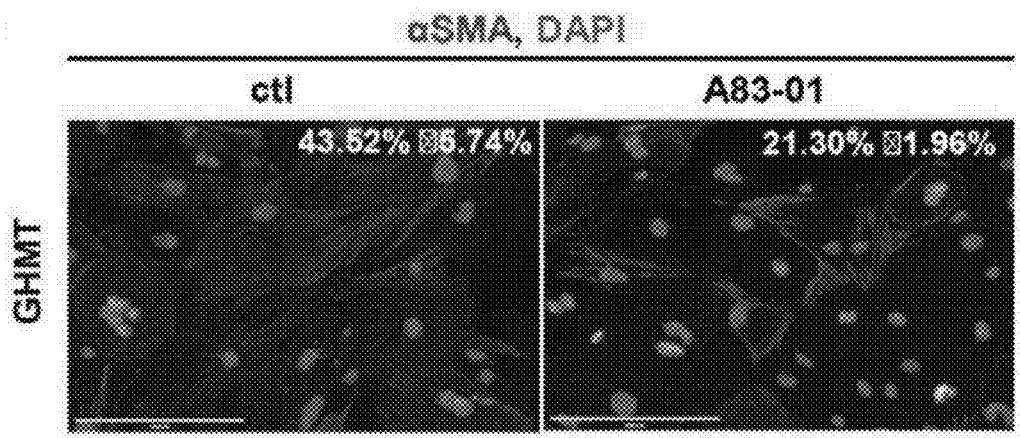

Example 6—Inhibitors of TGF-β Signaling Suppress Pro-Fibrotic Genes and Enhance Cardiac Reprogramming In addition to the ROCK pathway, the TGF-β pathway plays a critical role in pro-fibrotic gene expression. Treatment of MEFs with A83-01, a selective inhibitor of TGF-β signaling [Tojo, M. et al., *Cancer Sci.* 96, 791-800 (2005)] decreased phosphorylation of Smad2, and inhibited expression of Fn-EDA, Col1a1 and Col3a1, and formation of αSMA+ stress fibers in GHMT- and GHMT2minfected cultures (FIG. 58-60). The 2 m significantly decreased expression of Fn-EDA, Col1a1 and Col3a1 (FIG. 59). Among the four groups of cultures, GHMT, GHMT with A83-01, GHMT2m, and GHMT2m with A83-01, the lowest expression of pro-fibrotic genes was detected in GHMT2m-cultures treated with A83-01, indicating that two microRNAs and A83-01 synergistically suppress pro-fibrotic events in reprogramming cells.

Figure 61:
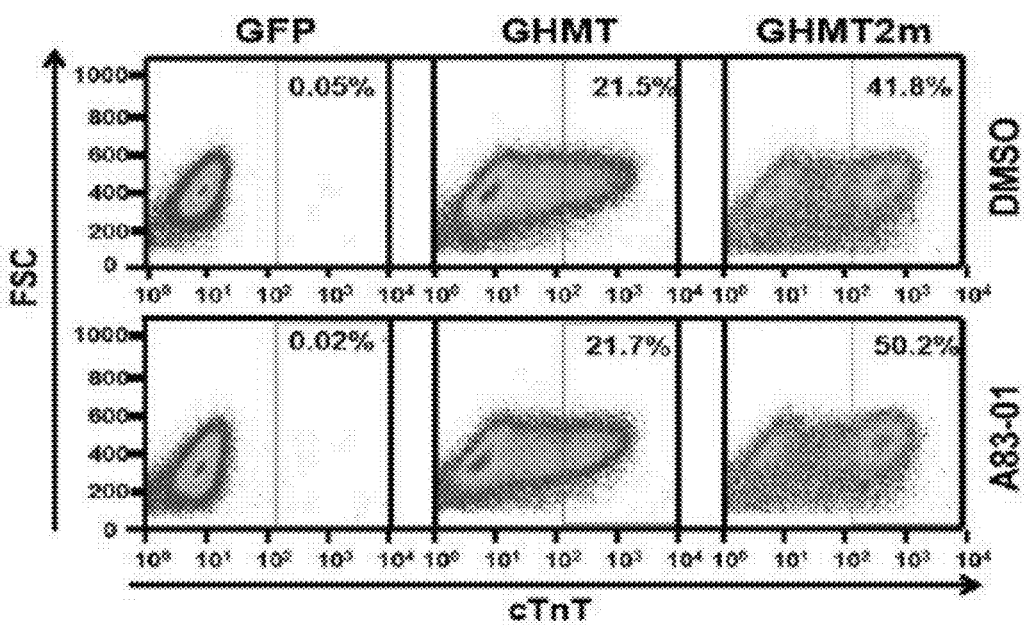
Figure 62:
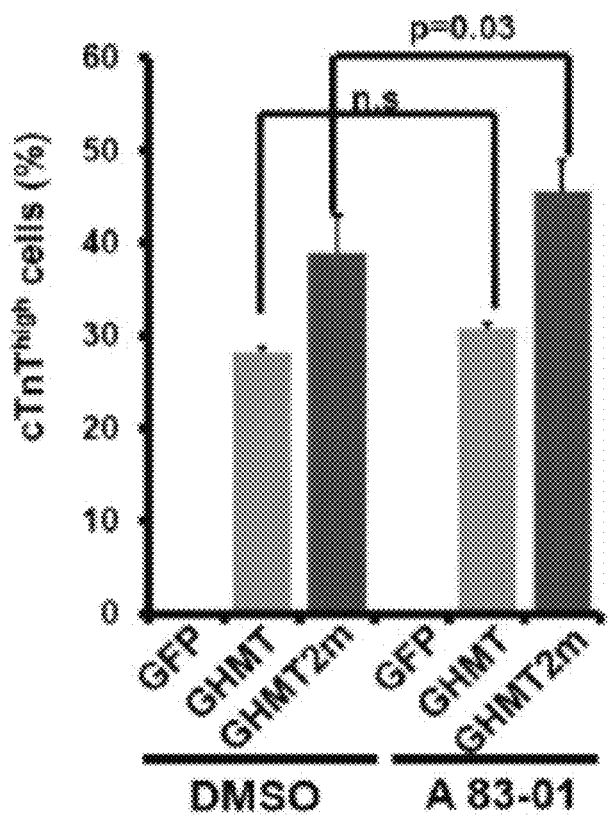
FIG. 62 is a histogram. Cells positive for cTnThigh were quantified (n=2 for GFP, n=4 for GHMT and GHMT2m). n.s, not significant.
Figure 63:
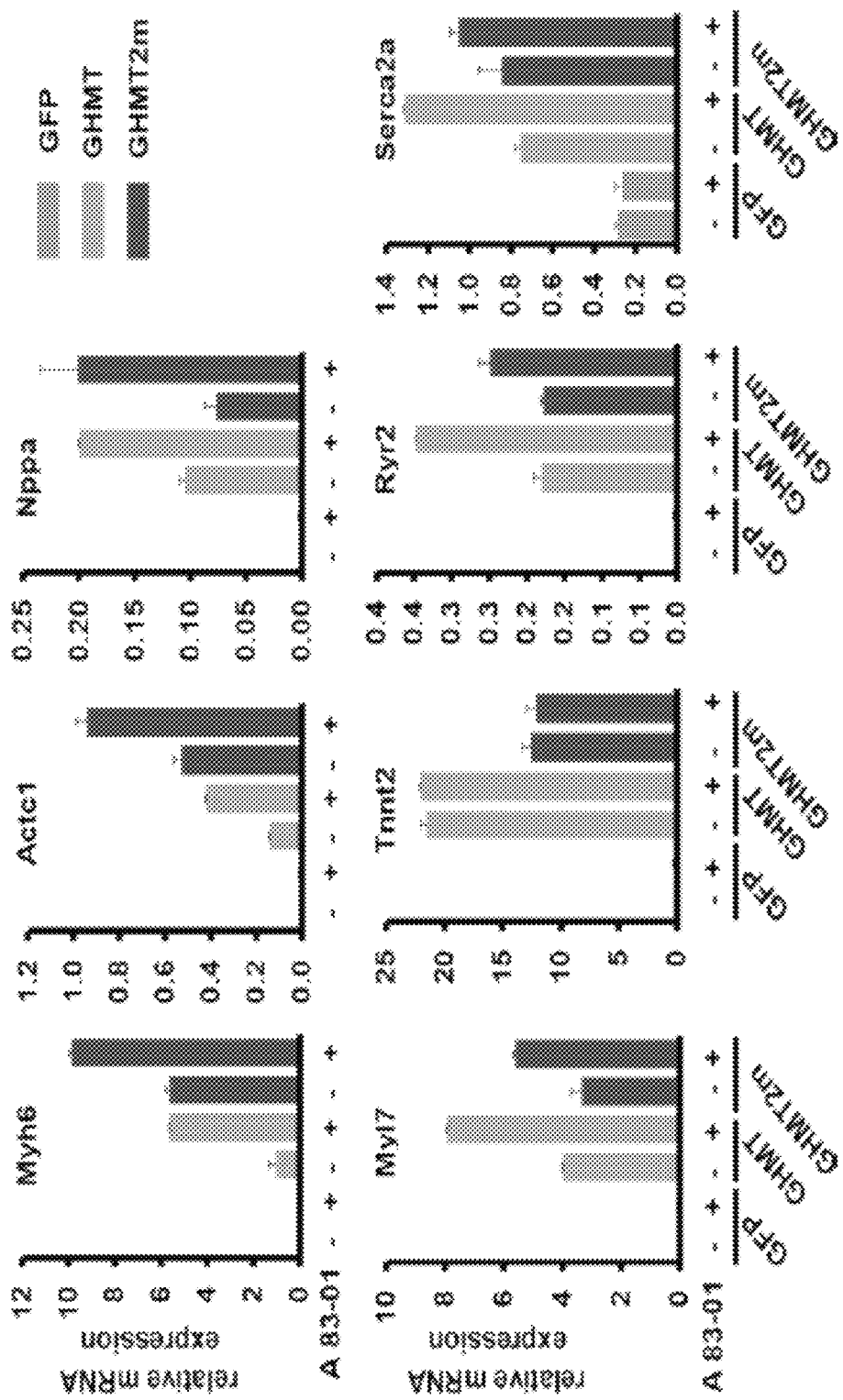
FIG. 63 is a set of seven histograms showing the results of qPCR analysis for expression of the indicated cardiac genes in reprogramming cells at day 7. MEFs expressing the indicated factors were treated with A83-01 or DMSO for 5 days. Gene expression was normalized to GAPDH.

Given the ability of A83-01 to inhibit pro-fibrotic signaling, the effects of A83-01 on cardiac reprogramming was examined. A83-01 alone did not induce cTnT+ cells, as determined by flow cytometry. In contrast, A83-01 increased cTnT$^{high}$ population from approximately 28.1% to approximately 30.7% in GHMT-infected cultures and from approximately 38.8% to approximately 45.6% in GHMT2m-infected cultures at day 7 (FIGS. 61 and 62). More significant increasing occurred at day 14. Immunostaining showed that A83-01 significantly increased the proportion of cTnT+ cells in GHMT- and GHMT2m-cultures from approximately 45% and approximately 60%, respectively, to approximately 58% and 67%, respectively (FIGS. 24 and 25). A83-01 also significantly increased the proportion of α-actinin+ cells in GHMT- and GHMT2m-cultures from approximately 34% and approximately 42%, respectively, to approximately 57% and 64%, respectively (FIGS. 24 and 25). A83-01 treatment also enhanced a program of cardiomyocyte gene expression in reprogramming cells (FIG. 63).

Figure 27:
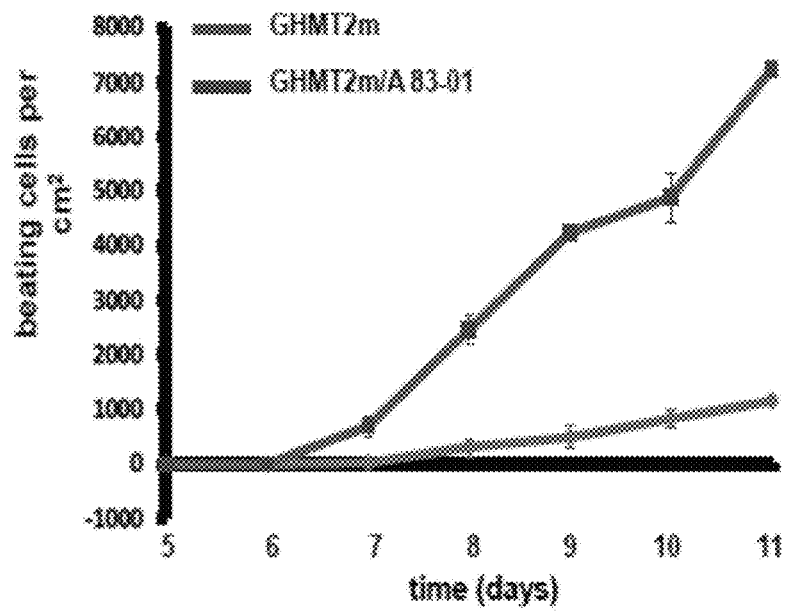
Figure 28:
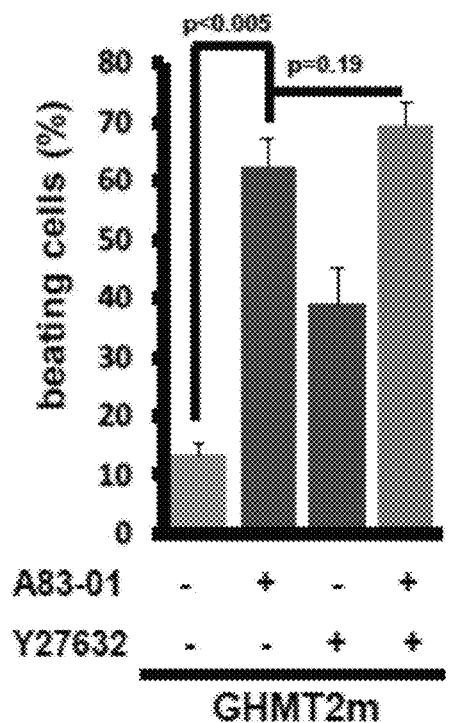

The most dramatic effect of blocking TGF-β signaling was observed at the level of cell contraction. In the absence of A83-01, beating cells were observed 3 weeks post-expression of GHMT, and reached approximately 200 cells per cm$^2$ by 4 weeks (FIG. 26). Treatment of GHMT-infected cultures with A83-01 led to cell beating by 11 days, which culminated in dramatic and spontaneous contraction of about 4400 cells per cm$^2$ by 4 weeks (FIG. 26). Even more pronounced changes were observed in GHMT2m-infected cultures. By day 8, GHMT2m reprogrammed a fraction of MEFs into beating cells (about 300 cells per cm$^2$), and A83-01 treatment increased the number of beating cells by 8-fold (FIG. 27). By day 11, GHMT2m produced approximately 13% beating cells. GHMT2m plus A83-01 produced approximately 63% beating cells, or approximately 7200 beating cells per cm$^2$ (FIGS. 27 and 28). This represents the highest efficiency of reprogramming, and correlates with the most significant loss of pro-fibrotic gene expression (FIGS. 58-60).

Adding A83-01 and Y27632 together slightly increased beating cell population, which is not significant, compared to that resulted from treatment with A83-01 alone (FIG. 28). These data suggest that other barriers to cardiac reprogramming exist.

Figure 29:
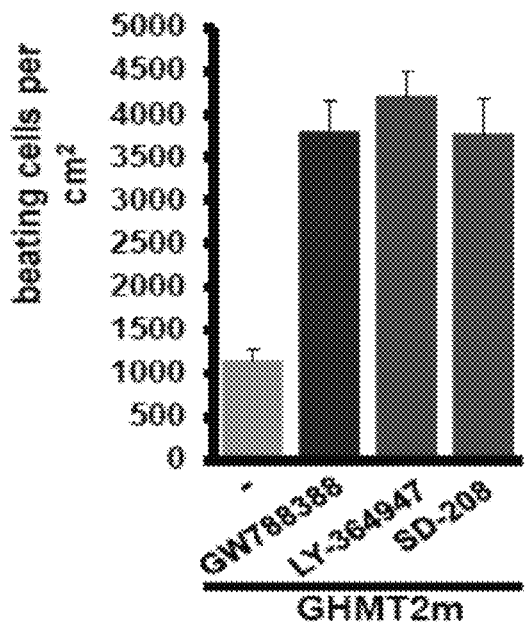

To exclude the possibility of off-target effects of A83-01, other inhibitors of TGF-β signaling were examined. Other ALK5 inhibitors, including LY-364947 [Sawyer, J. S. et al., *J. Med. Chem.* 46, 3953-6 (2003)], SD-208 [Uhl, M. et al., *Cancer Res.* 64, 7954-61 (2004)] and GW788388 [Tan, S. M et al., *Am. J. Physiol. Heart Circ. Physiol.* 298, H1415-25 (2010)] also enhanced cardiac reprogramming by inducing more spontaneously beating cells (FIG. 29).

Figure 30:
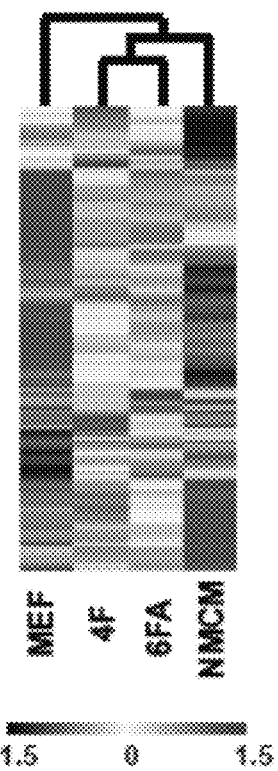

RNA-Seq analysis was performed on MEFs, GHMT-infected culture at day 7, GHMT2m+A83-01-cultures at day 7 and NMVM. The resultant heat map indicates that GHMT2m+A83-01 not only increases the efficiency, but also increases the similarity between iCMs and primary cardiac myocytes, compared to GHMT (FIG. 30). To globally examine effect of A83-01 on gene expression, RNA-Seq was performed for gene expression profiling in GHMT2m-infected MEFs treated with or without A83-01 at day 7. Top 10 ontologies that are enriched among genes up-regulated in A83-01-treated cultures are related to cardiomyocyte development, whereas ECM ontologies are enriched among genes down-regulated in A83-01-treated cultures (Table 3).

TABLE 3

Gene Ontology analysis of gens up- or down-regulated in GHMT2m-infected MEFs treated with A83-01, compared to GHMT2m-infected MEFs at day 7.

| Genes | | | GO Description | Enrichment Score | P-value |
| --- | --- | --- | --- | --- | --- |
| Up-regulated in GHMT at Day 7 | Cardiac Development | Cardiac Muscle Development | Contractile fiber part | 41.24 | 1.24E−18 |
| | | | Z disc | 31.31 | 2.53E−14 |
| | | | Muscle system process | 30.09 | 8.53E−14 |
| | | | Muscle contraction | 23.93 | 4.03E−11 |
| | | | Regulation of heart contraction | 23.64 | 5.44E−11 |
| | | | Regulation of heart rate | 23.23 | 8.18E−11 |
| | | | Sarcomere | 22.28 | 2.10E−10 |
| | | | Sarcoplasmic reticulum | 19.96 | 2.15E−09 |
| | | | Muscle tissue morphogenesis | 19.88 | 2.33E−09 |
| | | | Calcium ion binding | 19.83 | 2.43E−09 |
| | | | Striated muscle contraction | 19.24 | 4.41E−09 |
| | | | Cardiac muscle tissue morphogenesis | 18.99 | 5.68E−09 |

TABLE 3-continued

Gene Ontology analysis of gens up- or down-regulated in GHMT2m-infected MEFs treated with A83-01, compared to GHMT2m-infected MEFs at day 7.

| Genes | GO Description | Enrichment Score | P-value |
|---|---|---|---|
| Mitochodrion | Mitochondrion | 31.2 | 2.83E−14 |
| | Mitochondrial inner membrane | 26.72 | 2.50E−12 |
| | Mitochondrial membrane | 22.25 | 2.17E−10 |
| | Respiratory chain | 21.32 | 5.51E−10 |
| | Mitochondrial part | 20.08 | 1.91E−09 |
| | Mitochondrial membrane part | 19.71 | 2.76E−09 |
| | Transmembrane transporter activity | 19.27 | 4.29E−09 |
| Fibrotic Events | Extracellular matrix | 89.58 | 1.25E−39 |
| | Extracellular region | 87.72 | 7.98E−39 |
| | Proteinaceous extracellular matrix | 74.47 | 4.56E−33 |
| | Extracellular matrix part | 51.09 | 6.46E−23 |
| | Extracellular region part | 45.82 | 1.27E−20 |
| | Extracellular space | 44.41 | 5.15E−20 |
| | Extracellular matrix organization | 41.91 | 6.29E−19 |
| | Extracellular structure organization | 41.72 | 7.61E−19 |
| | Basement membrane | 28.97 | 2.63E−13 |
| | Collagen trimer | 28.48 | 4.30E−13 |

The data indicate that small molecules that suppress pro-fibrotic events by targeting TGF-β signaling dramatically enhance GHMT-mediated reprogramming of MEFs into beating iCMs. Adding miR-1 and miR-133 further decreases pro-fibrotic gene expression and dramatically increases beating iCMs in A83-01 treated GHMT-cultures.

Figure 31:
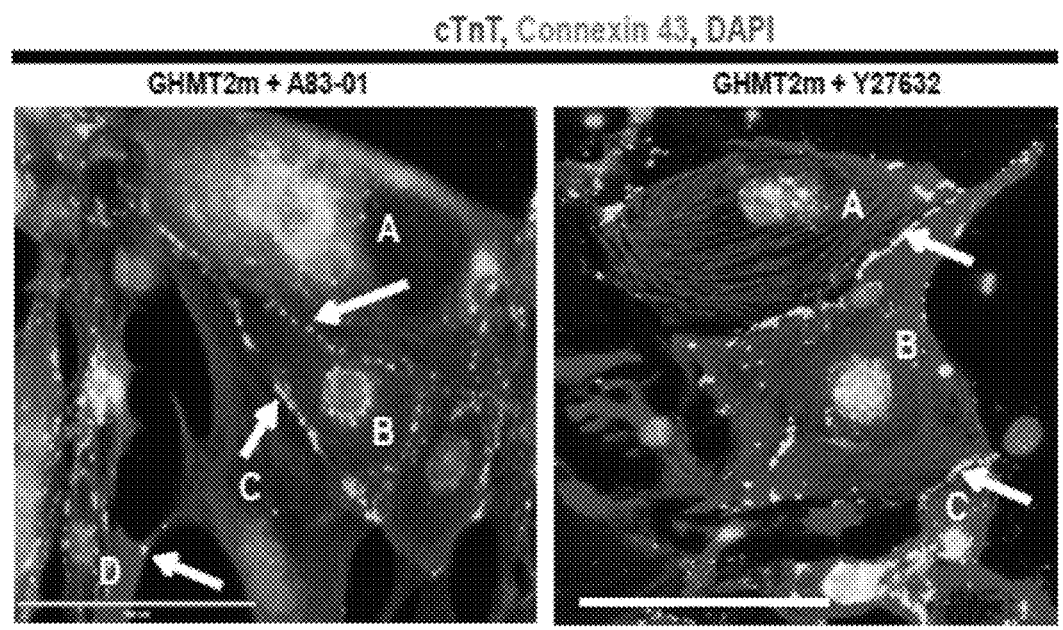
FIGS. 31-34: Induced cardiomyocytes display electrophysiological characteristics.
Figure 32:
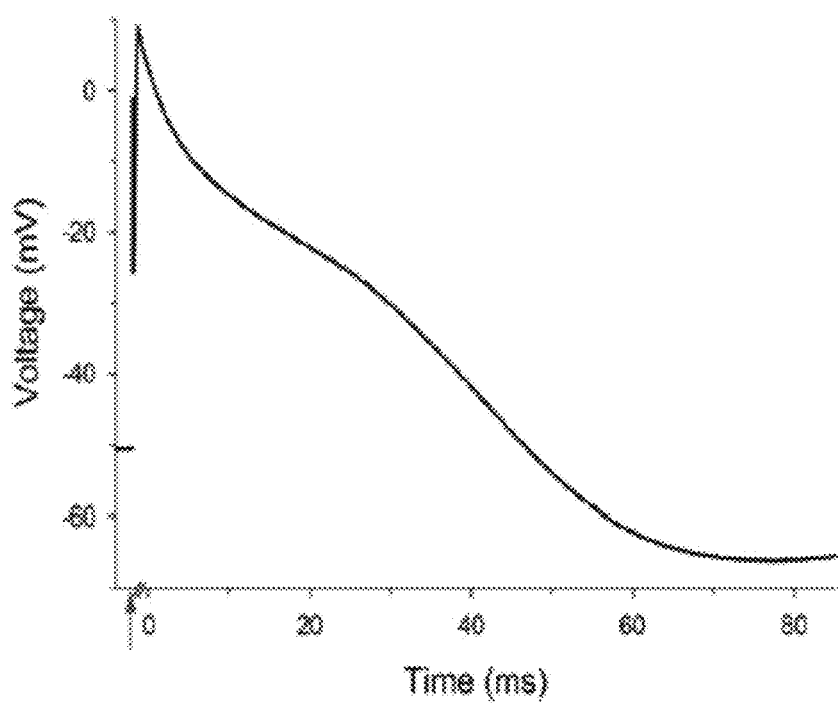
Figure 33:
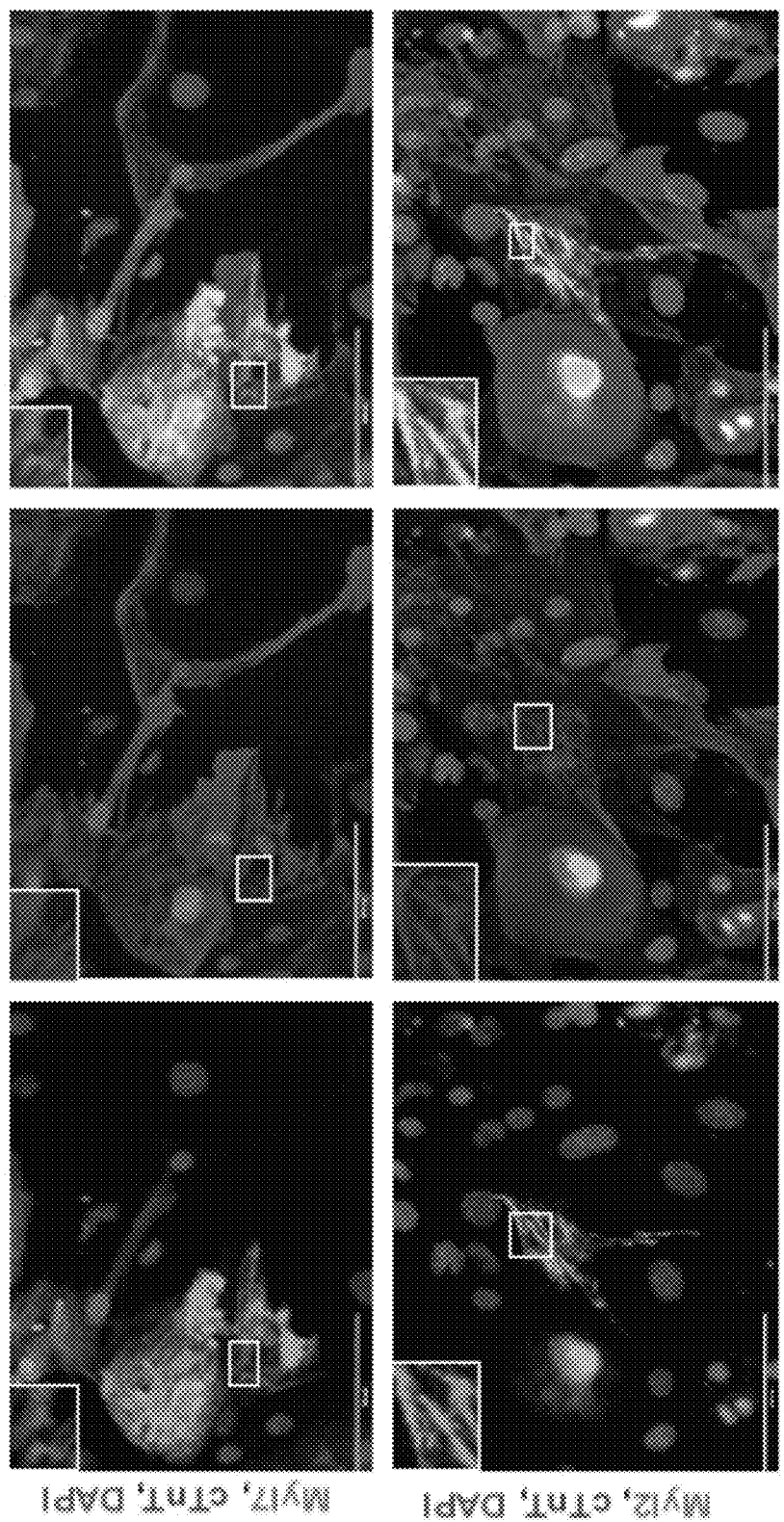

Example 7—Induced Cardiomyocytes Displayed Cardiac Electrophysiological Features A gap junction protein, connexin-43 (Cx43), is responsible for electrical coupling and intercellular communication of cardiomyocytes. Immunostaining revealed that Cx43 can be detected along the periphery of induced cardiomyocytes (FIG. 31), indicating development of gap junction channels. By day 14, immunostaining analysis indicated that expression of myosin light chain-2a (Myl7), an atrial-specific marker, was expressed in most of the induced cardiomyocytes, whereas, the ventricular-specific marker Myl2 was detected in a few of the cells (FIG. 33). The spontaneous action potentials (APs) of beating cells induced by GHMT2m plus A83-01 at day 9 was recorded. Consistently, it was found that half of the induced cardiomyocytes showed atrial or nodal-like APs, and the remainder of them displayed immature APs (FIG. 34; Table 4). The provoked action potentials (APs) were able to be elicited by current injection in amphotericin perforated patch current-clamp recordings from spontaneously-beating iCMs (FIG. 32). The provoked APs have a characteristic cardiomyocyte waveform, with fast upstroke, rapid repolarization, and plateau phases.

Figure 34:
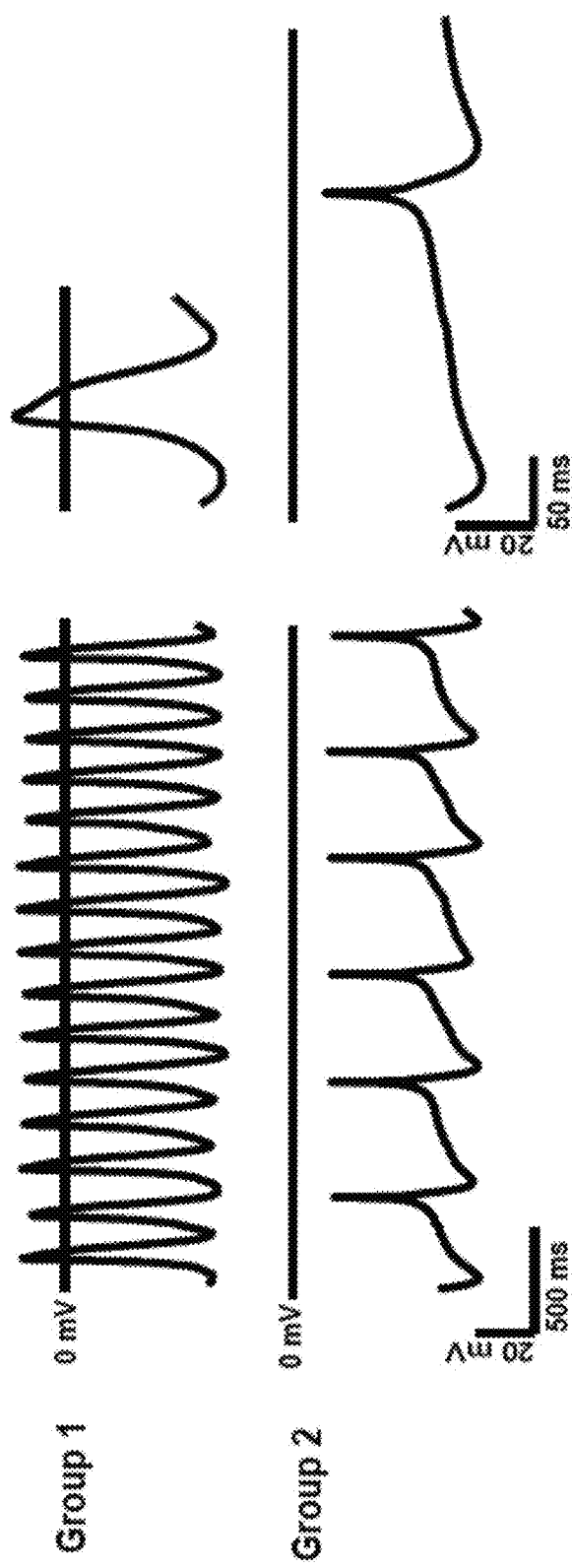

We next sought to characterize functional properties of these induced cardiomyocytes by electrophysiological analysis. Action potentials (APs) were recorded from single spontaneously beating cells on day 9 of reprogramming. Induced cardiomyocytes fired spontaneous APs (FIG. 34). Frequency and shapes of APs varied, consistent with a wide range of development or differentiation on day 9 of reprogramming (FIG. 34; Table 4). APs of induced cardiomyocytes mimic those of fetal (or nodal) cardiomyocytes by showing high rate of spontaneous firing, short AP durations and slow upstroke velocity (Table 4). During cardiac development in vitro and in vivo, early differentiated cardiomyocytes fire nodal-like APs that specialize into atrial-, ventricular- and nodal-like APs at later differentiation stages. Therefore, iCMs formed on day 9 appear to mimic early development of cardiomyocytes.

Figure 68:
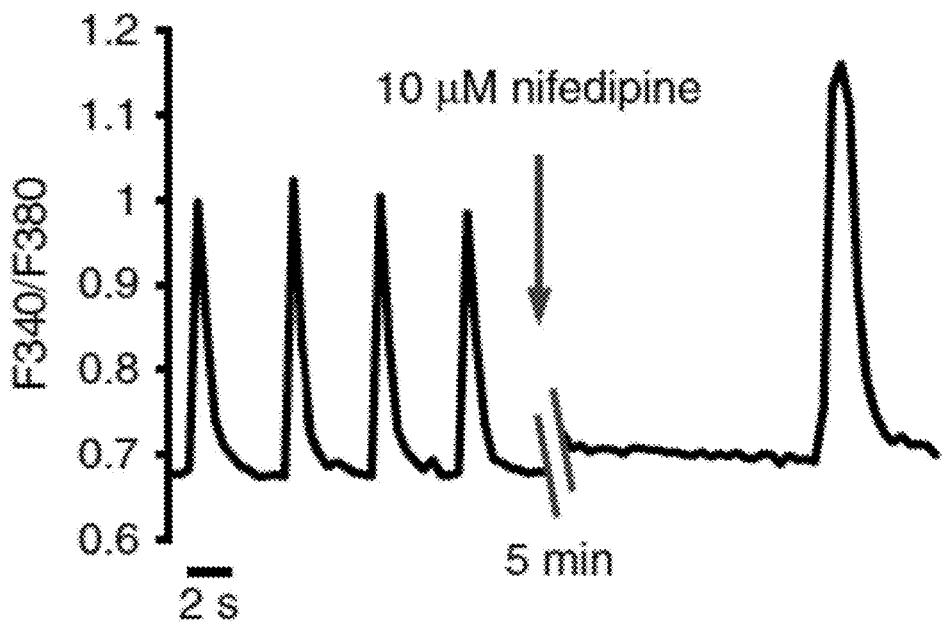
FIG. 68 is a line graph of recorded calcium transients showing the effect of 10 mM nifedipine on the calcium-transient frequency of iCMs. F340/F380, ratio of fluorescence intensity at 340 and 380 nm.
Figure 69:
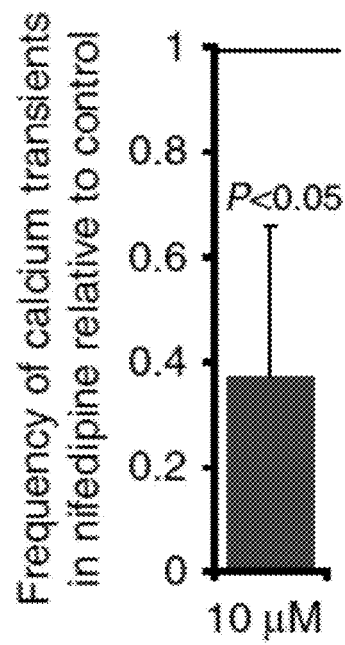
FIG. 69 is a bar graph showing the quantification of calcium-transient frequency from experiments shown in FIG. 68. Data are presented as mean+s.d. $P<0.05$ versus calcium-transient frequencies before nifedipine treatment by Student's t-test. N=10.

To determine whether iCMs were developing functional excitation-contraction (EC) coupling, we imaged spontaneous calcium transients from Fura-2 AM-loaded iCMs. Spontaneous calcium transients were detected in spontaneously beating cells on days 10-12 (FIGS. 68-71). Addition of nifedipine, a blocker of L-type calcium channels, significantly decreased the frequency of calcium transients, indicating that L-type calcium channels contribute to EC coupling in the iCMs as they do primary cardiomyocytes (FIGS. 68-69). To determine whether iCMs are able to appropriately respond to hormone stimulation, a critical function of normal cardiomyocytes, we measured calcium transients in response to the b-adrenergic agonist isoproterenol (Iso).

TABLE 4

Table of action potential waveform parameters recorded from group 1 and group 2 induced cardiomyocytes including firing rate frequency, the most negative and positive membrane potentials (Vmin, Vmax), action potential amplitude, maximum upstroke velocity (dv/dtMax) and the action potential duration at 10% and 90% repolarization, respectively (APD50, APD90).

| | Frequency (AP/min) | Vmin (mV) | Vmax (mv) | Amplitude | Dv/dtMax (mV/ms) | APD 50 (ms) | APD 90 (ms) |
|---|---|---|---|---|---|---|---|
| Group 1 (n = 4) | 174.8 ± 33.3 | −48.6 ± 3.9 | 5.5 ± 5.3 | 54.1 ± 7.4 | 1.4 ± 0.4 | 39.7 ± 12.0 | 99.9 ± 22.5 |
| Group 2 (n = 5) | 98.9 ± 14.5 | −48.4 ± 2.6 | 45.7 ± 5.9 | 32.7 ± 3.3 | 2.2 ± 1.0 | 27.7 ± 7.0 | 85.2 ± 24.3 |

Figure 70:
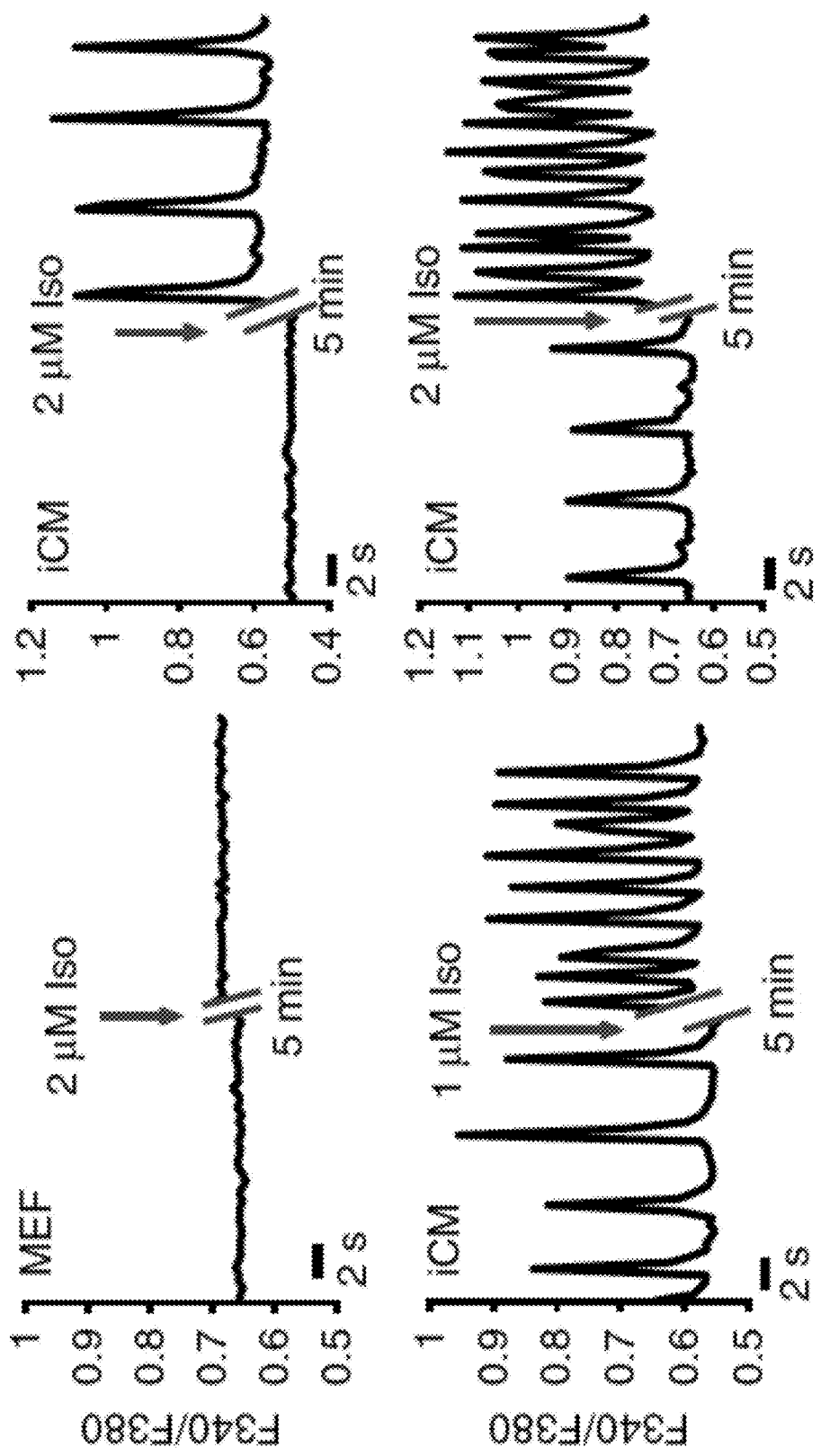
FIG. 70 is a set of graphs of recorded calcium transients showing that treatment with Iso (1 or 2 μM) increases calcium-transient frequency of iCM. F340/F380, ratio of fluorescence intensity at 340 and 380 nm.
Figure 71:
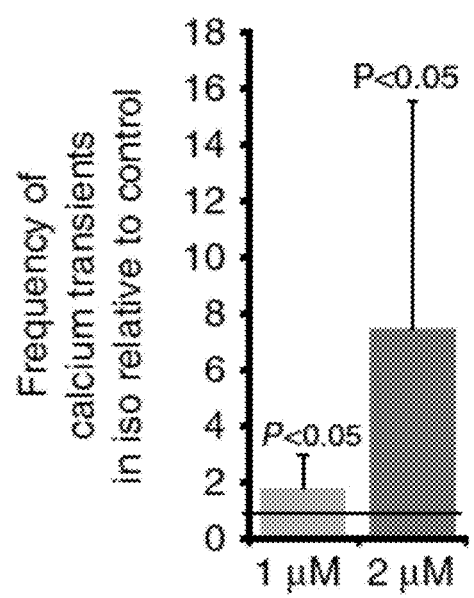
FIG. 71 is a graph of the quantification of calcium-transient frequency from experiments shown in FIG. 70. Data are presented as mean+s.d. $P<0.05$ versus calcium-transient frequencies before Iso treatment by Student's t-test. N=21 for the group treated with 1 μM Iso, n=14 for the group treated with 2 μM Iso.

Addition of 1 or 2 mM Iso significantly increased frequency of cell contraction and spontaneous calcium transients (FIGS. 70-71). In the presence of Iso, some cells that did not beat began to spontaneously contract (FIG. 70). These data suggest that the development of functional EC coupling machinery and b-adrenergic signalling components in iCMs.

Figure 64:
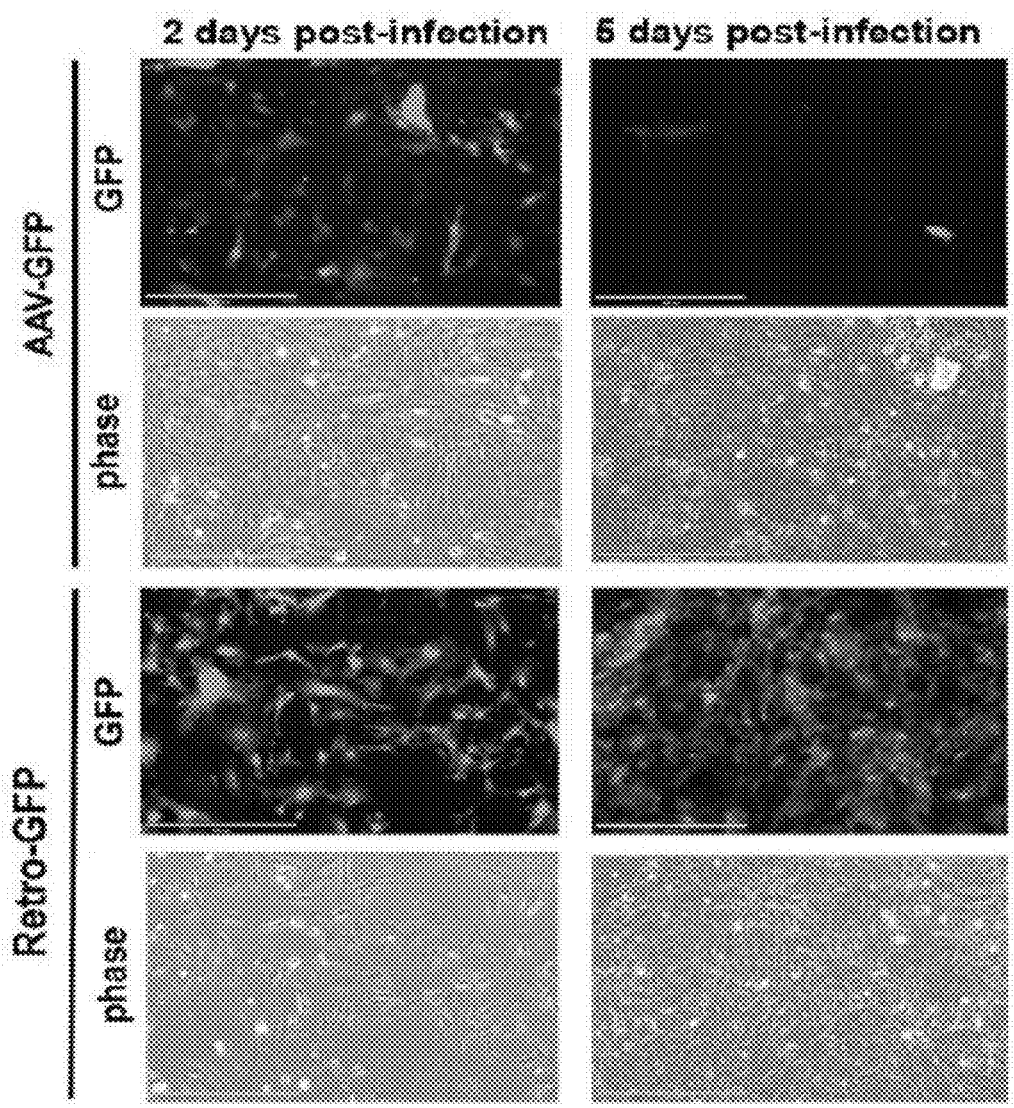
FIGS. 64-65: GHMT2m induces beating cardiomyocytes through an Adeno-associated viral (AAV) delivery system.
Figure 65:
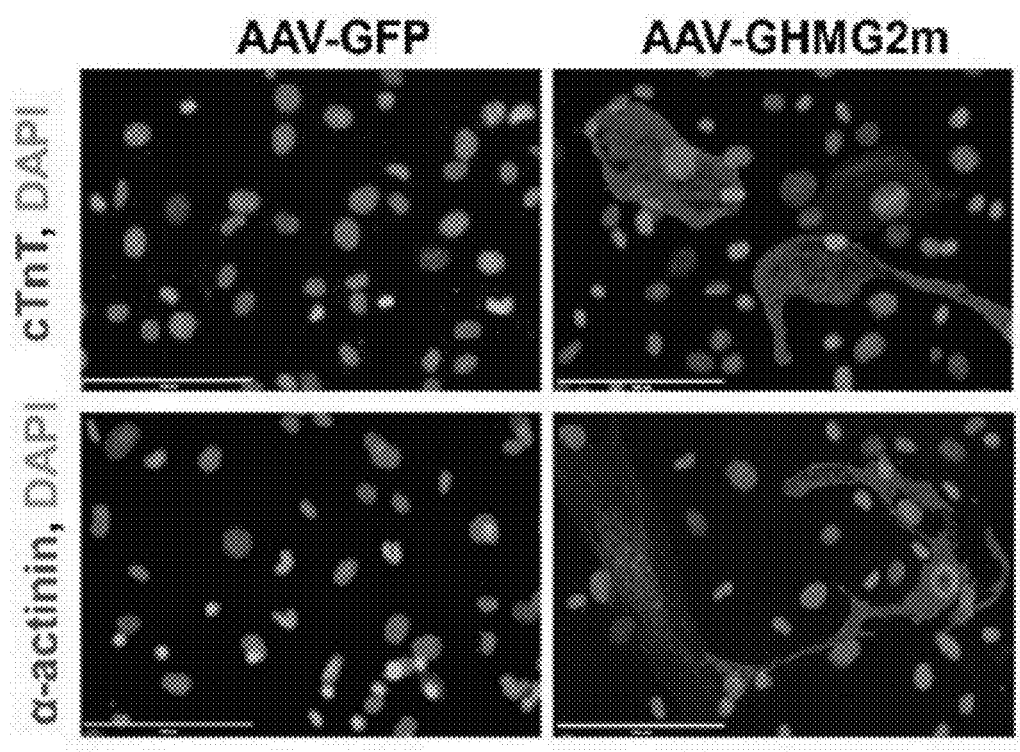

Example 8—Induction of Spontaneously Beating iCMs from MEFs by Using an Adeno-Associate Viral Delivery System Delivery of reprogramming factors to injured hearts via a retrovirus or lentivirus raises safety issues in clinical applications due to the potential consequences of the viral delivery vector. Clinical trials using adeno-associated virus (AAV) for gene therapy have shown safety and efficacy. AAV is a delivery system with very low chance of genome integration. A stereotype of AAV, AAV-DJ, was identified that infected MEFS with a short expression period (FIG. 64). AAV-GHMT2m plus A83-01 induced a small fraction of fibroblasts to be positive for cTnT, α-actinin, and spontaneously contract by day 12 (FIG. 65). Although the efficiency of AAV-mediated reprogramming is not comparable to retrovirus-mediated reprogramming, the data indicate that an episomal system can be used to reprogram fibroblasts into beating cardiomyocytes.

Example 9—Induction of Spontaneously Beating iCMs from Adult Mouse Fibroblasts

Adult fibroblasts are less amenable to reprogramming than embryonic fibroblasts. [Stadtfeld, M., et al., *Nat. Methods*. 7, 53-5 (2010)] The efficiency of reprogramming adult fibroblasts into beating cardiomyocytes is less than 0.1%, which is quiet inefficient. It was therefore examined whether inhibiting pro-fibrotic events could enhance reprogramming of adult fibroblasts including adult cardiac fibroblasts (ACFs) and adult tail-tip fibroblasts (ATTFs).

Figure 35:
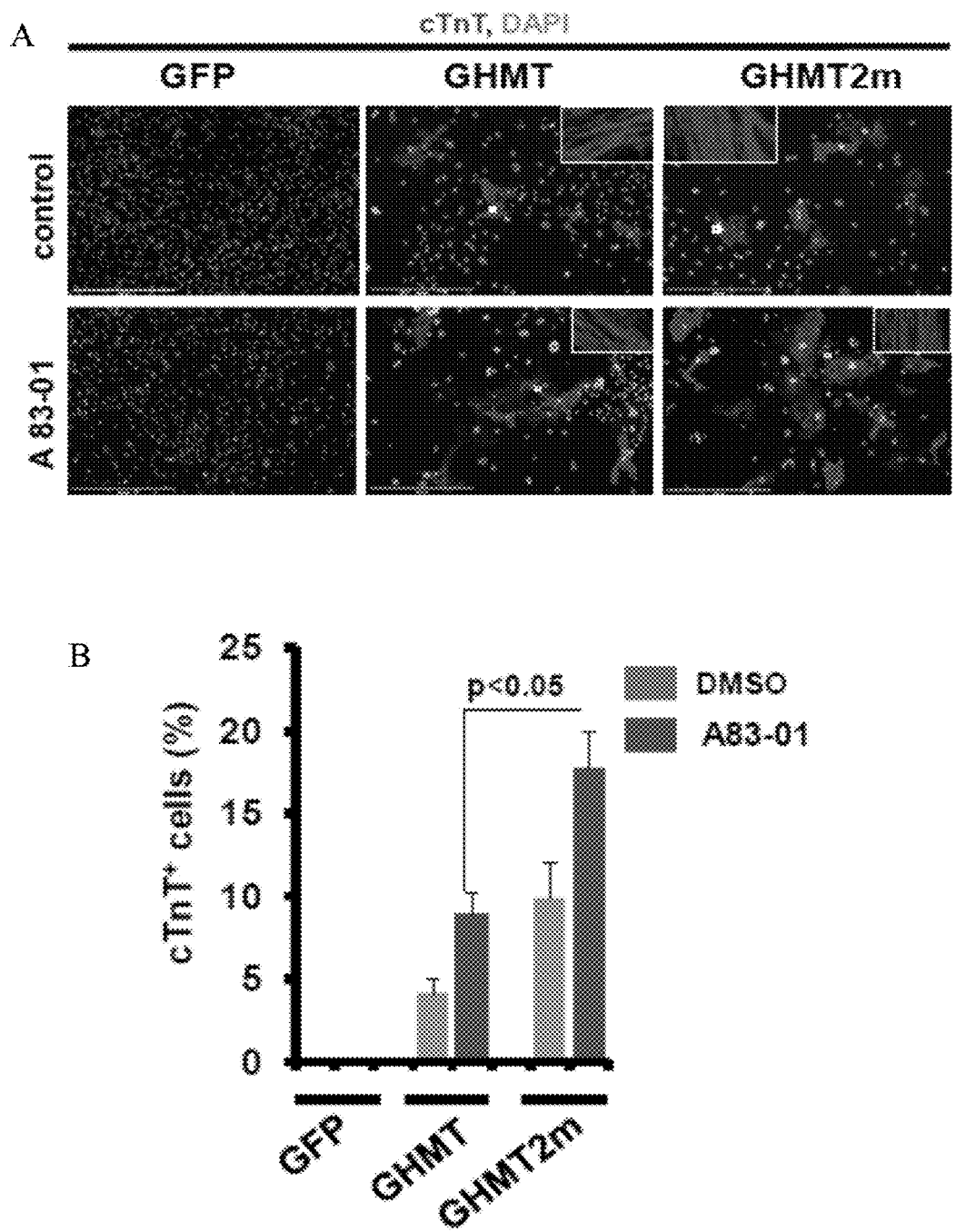
FIGS. 35-41: A83-01 enhances reprogramming of adult fibroblasts into beating iCMs.
Figure 36:
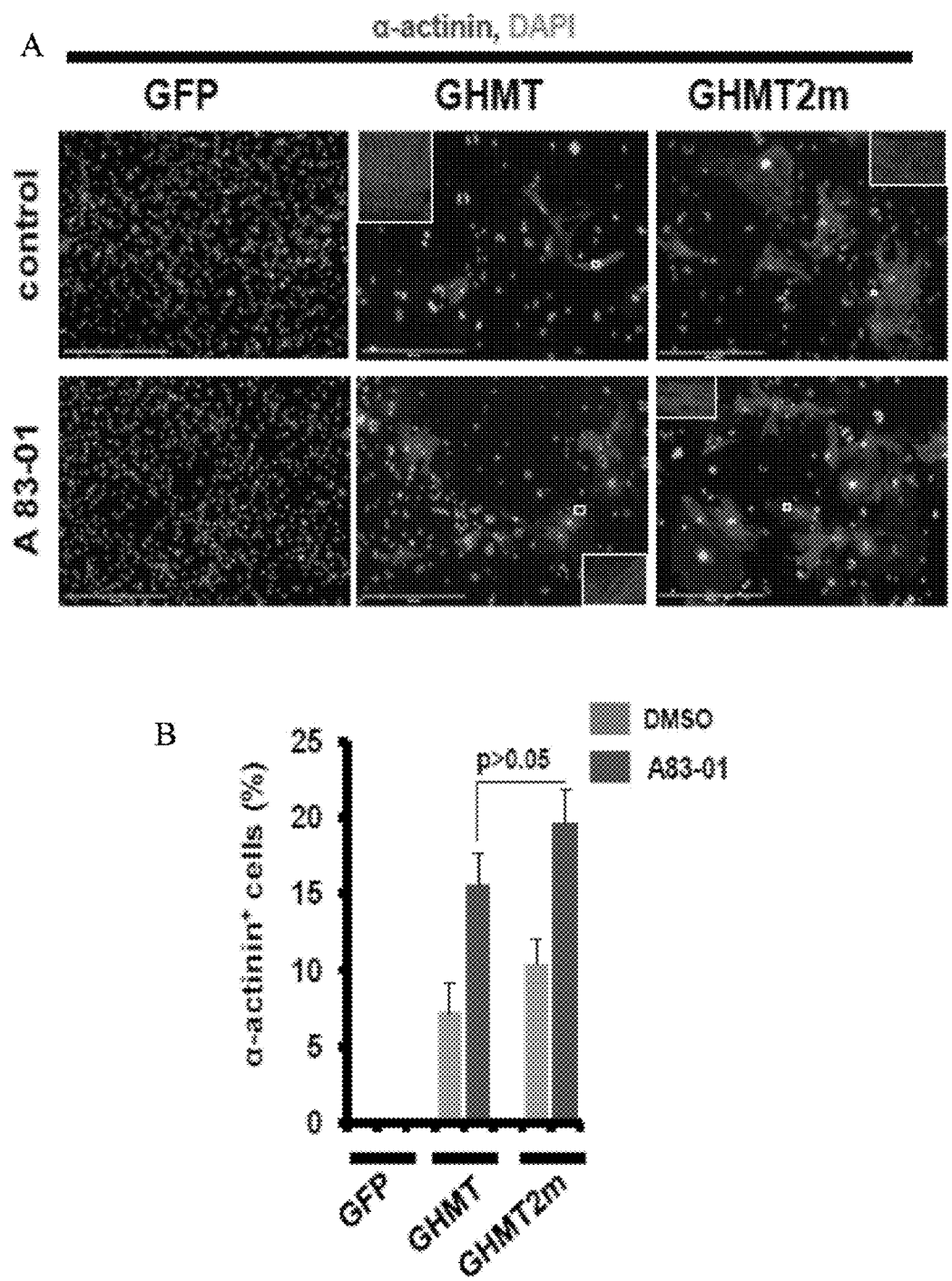
Figure 37:
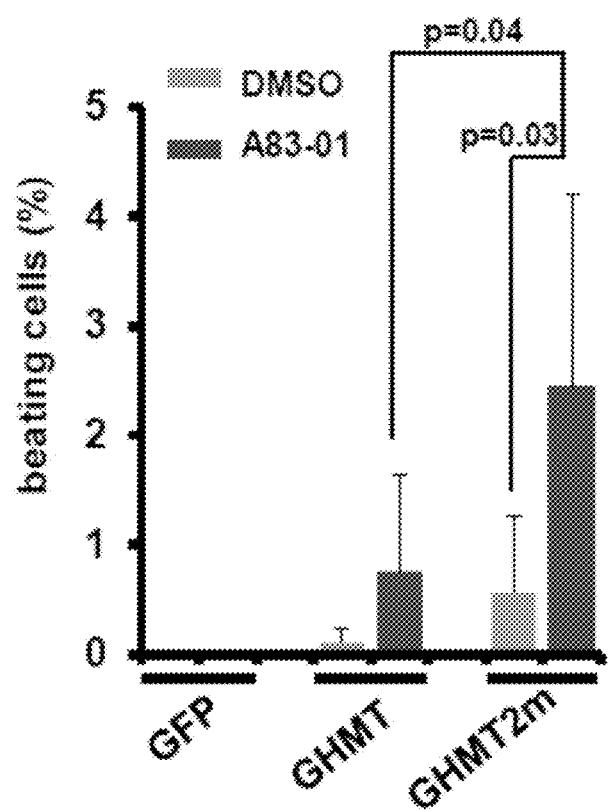
Figure 66:
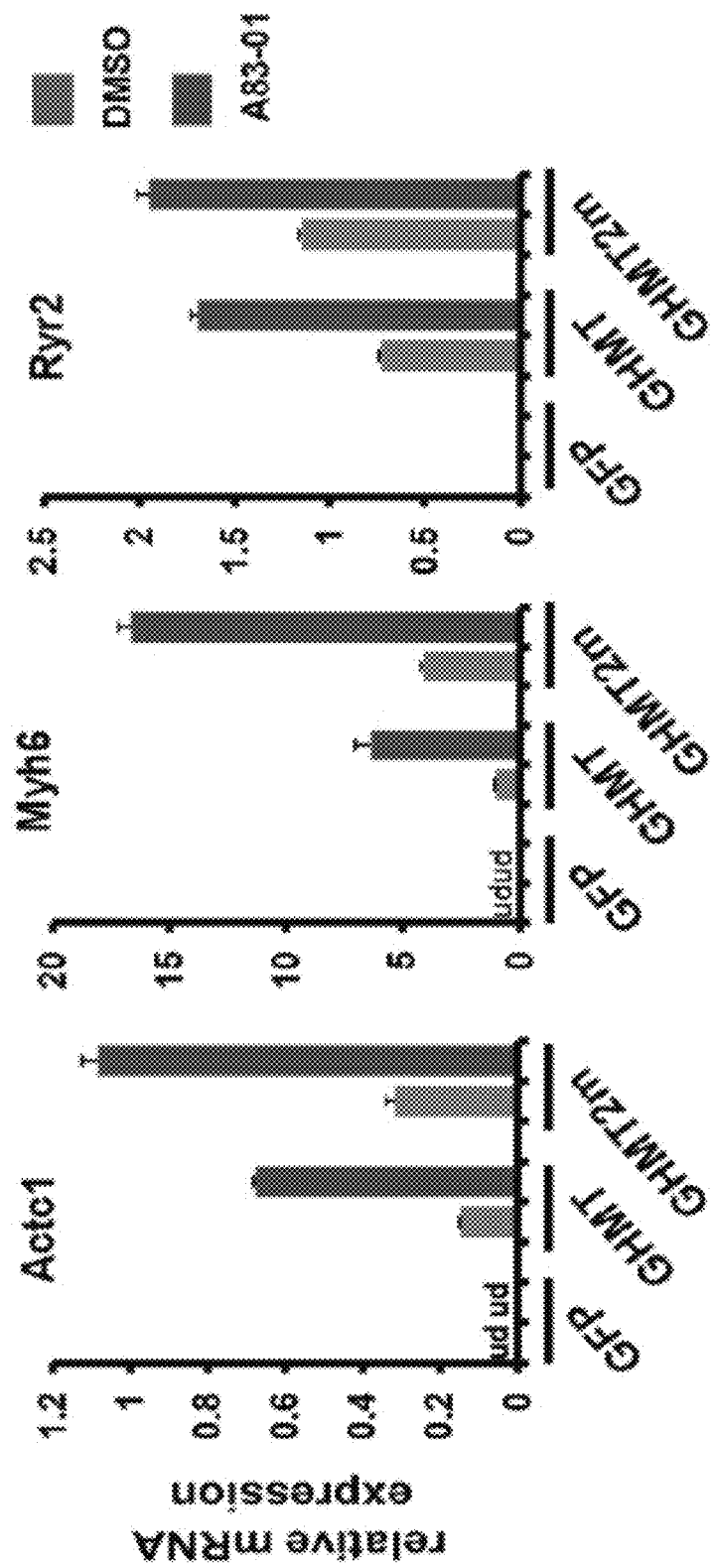
FIGS. 66-67: Inhibition of pro-fibrotic signaling enhances cardiac reprogramming of adult fibroblasts.

By 4 weeks, GHMT induced approximately 5% of ACFs to be positive for cTnT. Adding of A83-01 significantly increased the cTnT+ population to approximately 10% (FIG. 35). GHMT2m induced approximately 10% of ACFs to be positive for cTnT. Adding of A83-01 significantly increased the cTnT+ population to approximately 18% (FIG. 35). GHMT2m plus A83-01 induced approximately 18% of ACFs to be positive for another cardiomyocyte marker α-actinin (FIG. 36), which is significantly more than the α-actinin+ fraction induced by GHMT plus A83-01. GHMT plus A83-01 induced approximately 2.5% of ACFs to spontaneously contract by 5 weeks (FIG. 37). A83-01 also enhanced expression of other cardiac genes, Actc1, Myh6 and Ryr2 (FIG. 66). Therefore, GHMT2m plus A83-01 represents the most optimized combination among the 4 combinations to reprogram ACFs into beating cardiomyocytes.

Figure 38:
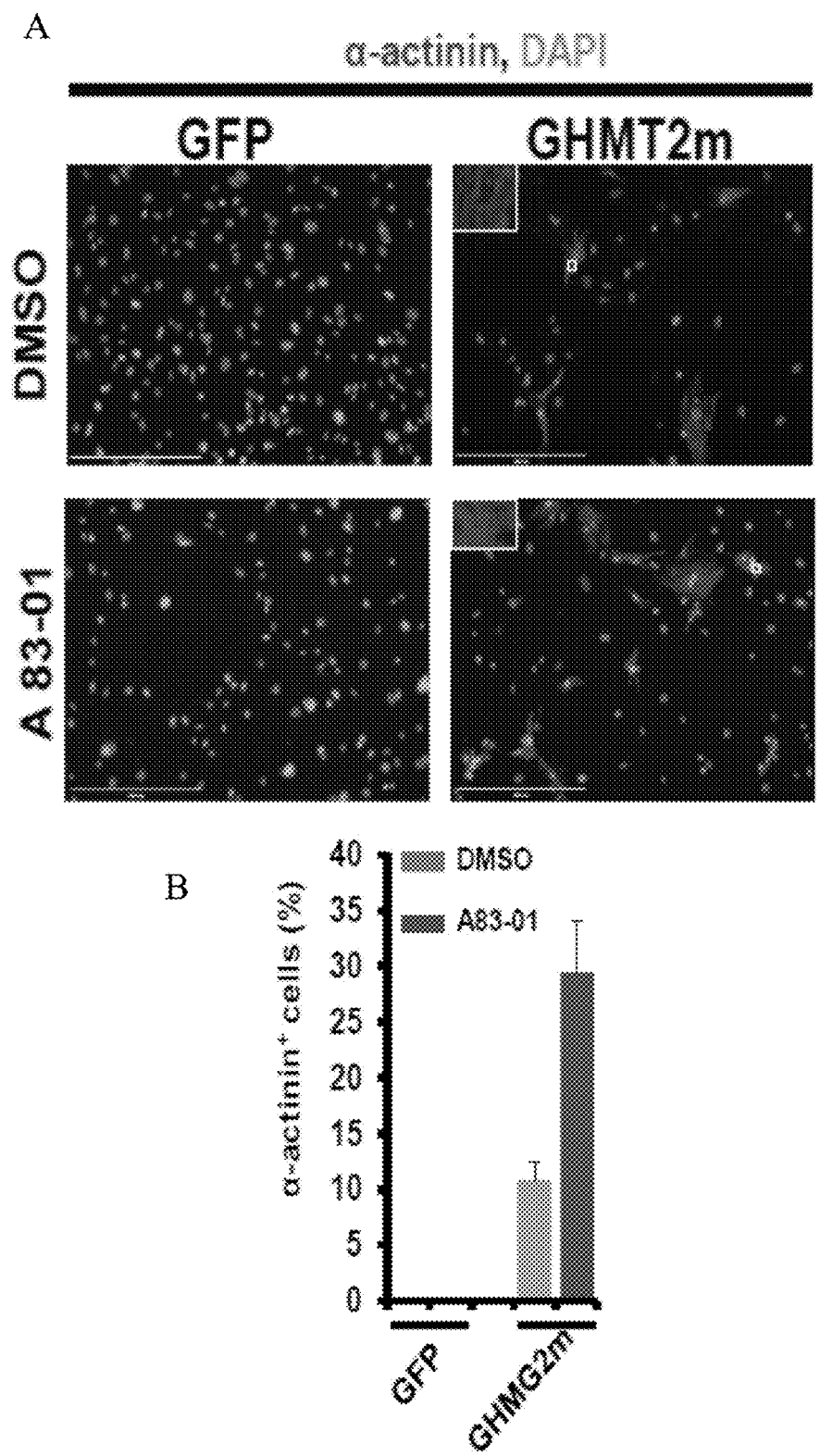
Figure 39:
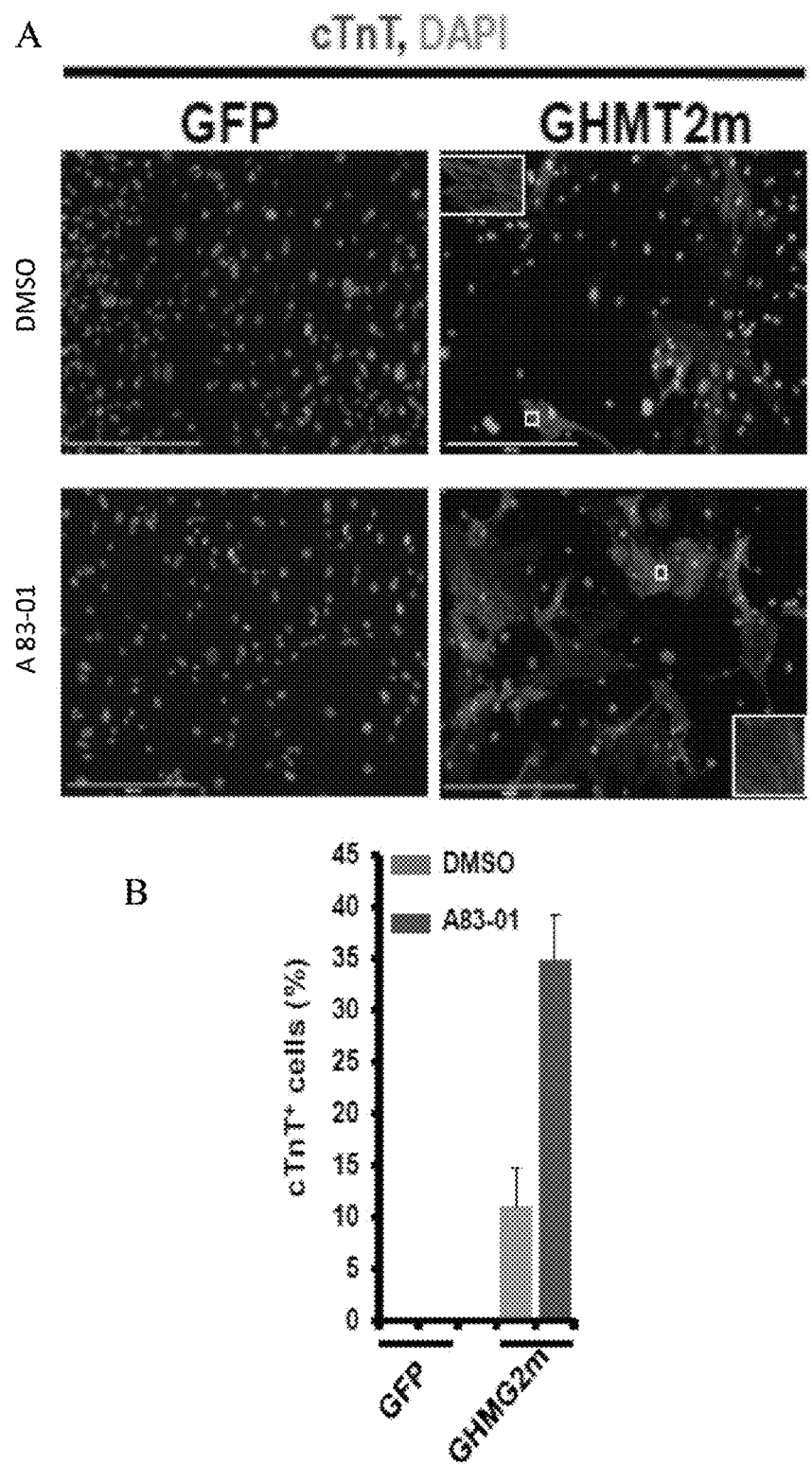
Figure 40:
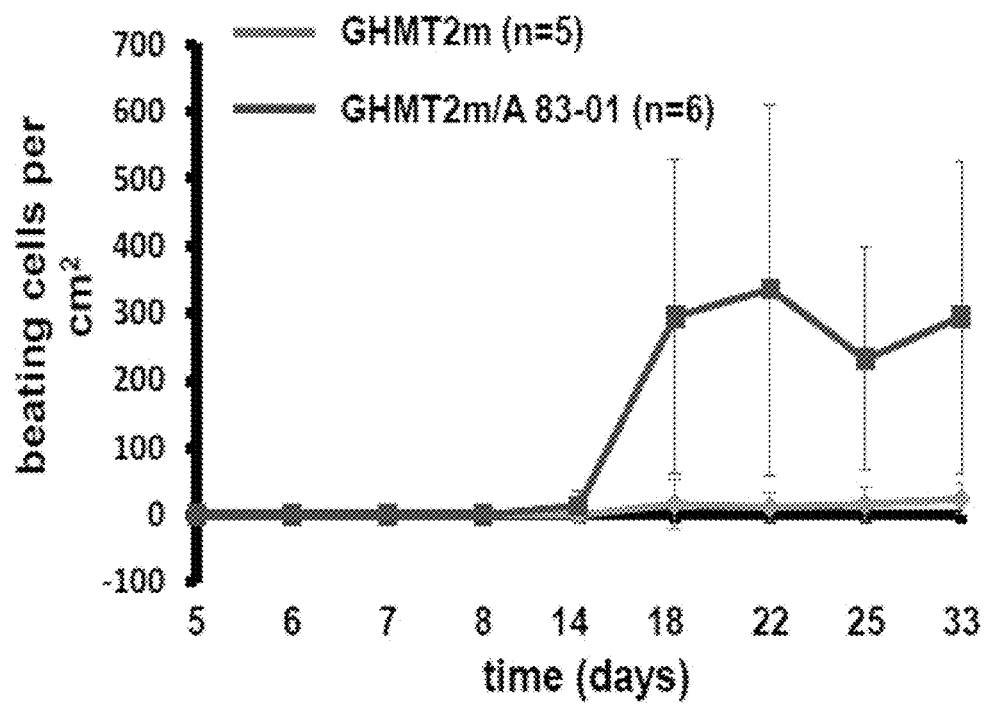
Figure 41:
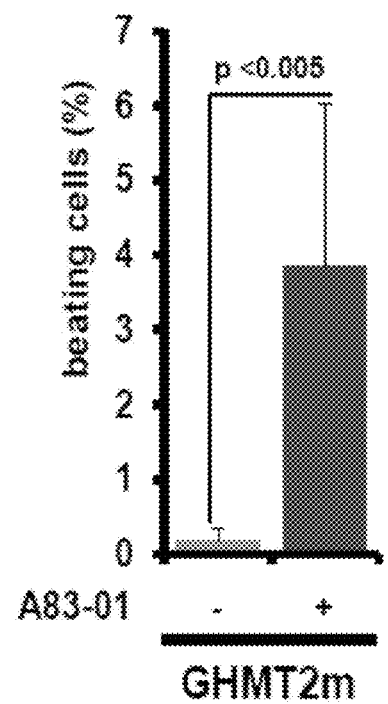
Figure 67:
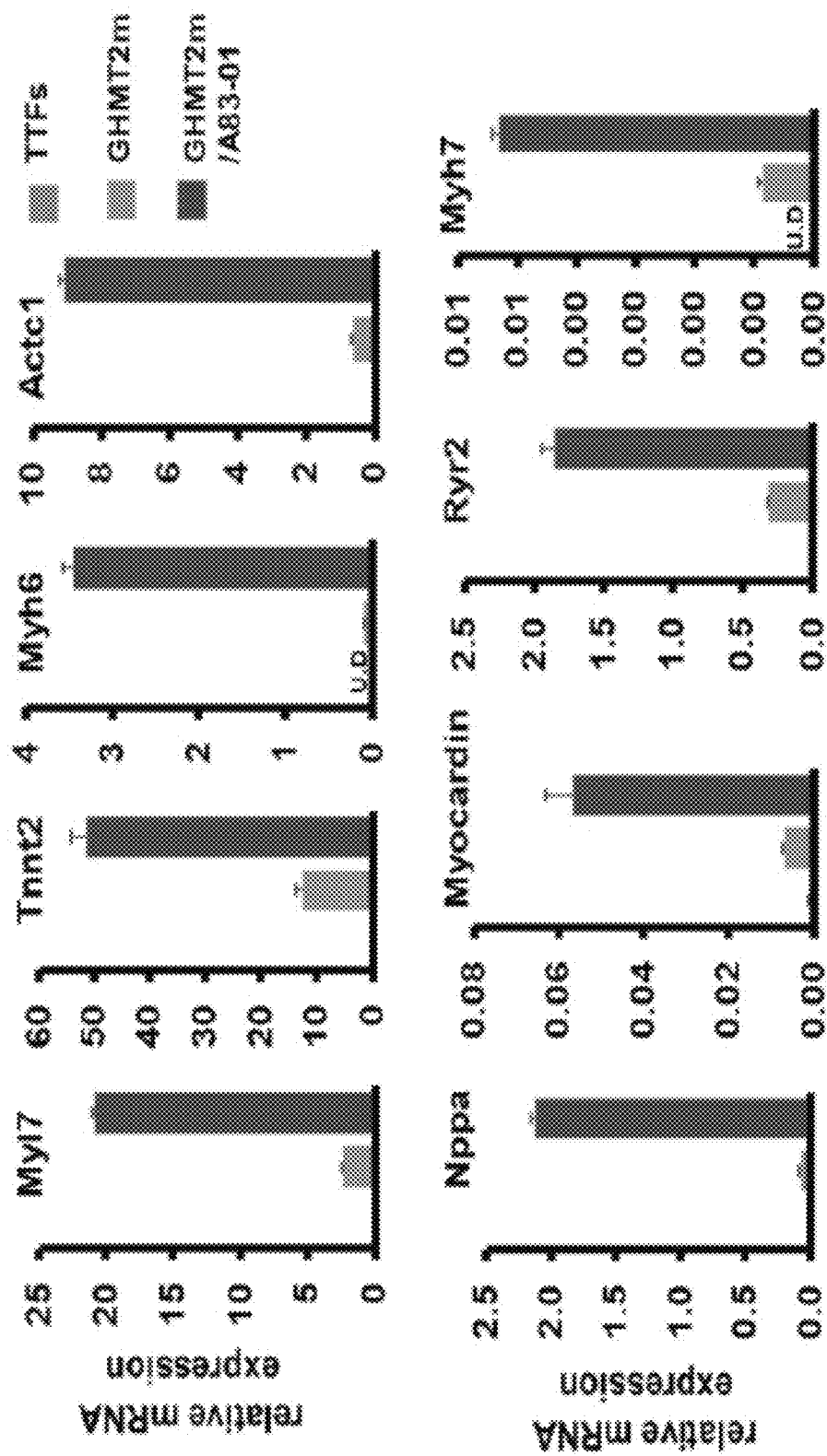

Next, we examined whether GHMT2m plus A83-01 could convert adult dermal fibroblasts, ATTFs into beating cardiomyocytes. GHMT2m reprogrammed a population (about 10%) of adult TTFs to be positive for cTnT and α-actinin (FIGS. 38 and 39). Adding A83-01 significantly increased the cell population positive for these markers to approximately 30% (FIGS. 38 and 39). Enhanced cardiomyocyte gene expression was detected in GHMT2m-TTFs treated with A83-01 (FIG. 67). GHMT2m induced approximately 40 beating cells per cm$^2$ after one month. Spontaneously beating cells appeared in A83-01 treated cultures by 2-3 weeks. By 4 weeks, approximately 300 cells per cm$^2$ (or about 4%) spontaneously contracted in A83-01 treated cultures (FIGS. 40 and 41). Thus, inhibition of pro-fibrotic signaling also increases the efficiency of reprogramming of adult fibroblasts into beating cardiomyocytes.

Example 10—Materials and Methods

Animal Experiments:

All research involving animals complied with protocols approved by the Institutional Animal Care and Use Committee (IACUC) of University of Colorado.

Preparation of Mouse Embryonic Fibroblasts (MEFs):

C57BL6 pregnant mice at E13 were order from Charles River's laboratory. Embryos at E14.5 were harvested and their internal organs and head were removed. The body below the liver was minced using blade to fine pieces. Minced embryos were incubated with 2 ml of 0.25% trypsin/1 mM EDTA, Phenol Red (Gibco) for 40 mins at 37° C. with 5% CO2. Cells were suspended in 25 ml of growth medium (DMEM/Hi glucose (Hyclone) 10% FBS (Gemini), 1.1% Penicillin-Streptomycin (Gibco) and 1.1% GlutaMAX supplement (Gibco)) and then plated on a 15 cm dish. In 24 hours, the media was aspirated and new 25 ml of growth medium was added. In 72 hours, MEFs were harvested and stored for future use.

Derivation of Adult Mouse Cardiac Fibroblasts (CFs) and Tail-Tip Fibroblasts (TTFs):

Hearts or skinned tails from adult C57BL6 mice were cut into small pieces with ~1 mm diameter. The biopsies were seeded on a 10 cm culture dish and incubated with 10 mL of growth medium (DMEM/Hi glucose (Hyclone), 10% FBS (Gemini:), 1.1% Penicillin-Streptomycin (Gibco) and 1.1% GlutaMAX supplement (Gibco)) at 37° C. with 5% CO$_2$. TTFs migrated out of the biopsies after 3 days. The media were changed every other day. Once the TTFs have reached a 70-80% confluence, the cells were harvested and stored for future use.

Generation of Retroviruses:

Twelve micrograms of retroviral plasmid DNA was transfected using Fugene 6 (Promega) into Platinum E cells (Cell Biolabs) which were plated on a 10-cm tissue culture dish at a density of 3×10$^6$ cells per dish, 24 hours prior to transfection. Twenty-four hours after transfection, viral medium was harvested and filtered through a 0.45 μm cellulose filter. The viral supernatant was mixed with polybrene (Sigma) to a final concentration of 6 μg/ml.

Viral Transduction:

Fibroblasts were plated on tissue culture dishes pre-coated with SureCoat (Cellutron) at a density of ~40 cells/mm$^2$ before transduction. The fibroblast growth medium was replaced with freshly made viral mixture containing polybrene (Sigma). Twenty four hours later, fibroblasts were infected again with viral mixture containing polybrene. Twenty fours later, the viral medium was replaced with induction medium, composed of DMEM/199 (4:1) (Gibco), 10% FBS (Gemini), 5% horse serum(Gemini), antibiotics (Gibco), 1× non-essential amino acids (Gibco), 1× essential amino acids (Gibco), 1× B-27(Gibco), 1× insulin-selenium-transferin (Gibco), 1× vitamin mixture (Gibco), and 1× sodium pyruvate (Gibco). Medium was changed every two-three days until cells were examined.

Intracellular Staining for Flow Cytometry:

Adherent fibroblasts were washed with DPBS (Gibco). Cells were detached from culture dish by treatment with 0.25% Trypsin/EDTA (Gibco) for 3 min at 37° C. Cells were then washed with 4 ml of 5% FBS (Gemini) in DPBS filtered through a cell strainer and centrifuge at 1200 rpm×6 mins.

Cells were washed with 500 ul of 1% BSA in DPBS. Cells were fixed with BD Cytofix/Cytoperm™ solution in 0.2 ml/1 million cells in 1.5 ml eppendorf tube for 20 min on ice. Cells were washed with 1 ml of BD perm/wash buffer and Centrifuged for 6 min at 1200 rpm. The supernatant was discarded; cells were washed again with 1 ml of BD Perm/wash buffer and left overnight at 4° C. The next day, Cells were centrifuged for 6 min at 1200 rpm, the supernatant discarded and 100 μl of Blocking buffer made with 5% goat, donkey serum (Sigma: G9023 and D9663) in Perm/wash buffer was added to the cells and incubated for 30 min at RT. A primary antibody: Mouse Troponin T (cTnT) antibody (Thermo Scientific, ms-295-p, 1:200), mouse anti-C-Myc antiboby (BD Pharmingen, 551102, 1:200) in 100 μl BD Perm/Wash buffer was added to the cells and incubated for 1 hr at RT. One ml cold BD Perm/wash buffer was added to the cells and centrifuged for 6 min at 1200 rpm. Cells were washed one more time with 1 ml of ice cold BD Perm/wash buffer as above. A secondary antibody: Anti-mouse Alexa 647 (Life technologies, A-31571, 1:200) in 100 μl BD Perm/wash buffer was added to the cells and incubated for 45 min at RT on a shaker. The cells were protected from light. Cells were washed twice with 1 ml cold BD Perm/wash buffer. Cells were re-suspended in 300 ul of 1% BSA/DPBS and then analyzed using FACS Caliber (BD Sciences) and FlowJo software.

Quantitative RT-PCR (qPCR):

Cells were harvested in TRizol reagent (Ambion) for RNA isolation. RNA was extracted with the RNeasy® Plus Universal Mini Kit (Qiagen). RT-PCR was performed using the Superscript III first-strand synthesis system (Invitrogen). qPCR was performed using the SYBR® Green PCR master mix (Applied Biosystems) or StepOne™ Real-Time PCR Systems (Applied Biosystems). Primers are listed in Supplementary Table 1. Ryr2 (Mm00465877_m1) and Myh7 (Mm01319006_91) are Taqman probes (Life technologies).

TABLE 5 qPCR primers

| Primers | Primer Sequence | Reference |
|---|---|---|
| αaSMA.F | TCAGCGCCTCCAGTTCCT | Henderson, N.C. et al., *Proc. Natl. Acad. Sci. U. S. A.* 103, 5060-5 (2006) |
| αSMA.R | AAAAAAACCACGAGTAACAAATCAA | |
| Fn-EDA.F | TTGATTTCTTTCATTGGTCCTGTCTT | Baelde, H.J. et al. *J. Pathol.* 204, 248-57 (2004) |
| Fn-EDA.R | AAACAGAAATGACCATTGAAGGTTTG | |
| Col1a1.F | AGACATGTTCAGCTTTGTGGAC | Smith, CL., et al., *Circ. Res.* 108, e15-26 (2011) |
| Col1a1.R | GCAGCTGACTTCAGGGATG | |
| Col3a1.F | ACGTAGATGAATTGGGATGCAG | Smith, CL., et al., *Circ. Res.* 108, e15-26 (2011) |
| Col3a1.R | GGGTTGGGGCAGTCTAGTG | |
| Snai2 (Slug).F | CATTGCCTTGTGTCTGCAAG | Smith, CL., et al., *Circ. Res.* 108, e15-26 (2011) |
| Snai2 (Slug).R | CAGTGAGGGCAAGAGAAAGG | |
| Snai1.F | GCGGAAGATCTTCAACTGCAAATATTGTAAC | Luo, D., et al., *Molecular cancer research: MCR.* 9, 234-45 (2011) |
| Snai1.R | GCAGTGGGAGCAGGAGAATGGCTTCTCAC | |
| GAPDH.F | GCAGTGGCAAAGTGGAGATTG | |
| GAPDH.R | GGAGATGATGACCCTTTTGGCTCC | |
| Tgfb1.F | TGGAGCAAC ATGTGGAACTC | Imai, K. et al., *J. Exp. Clin. Cancer Res.* 31, 3 (2012) |
| Tgfb1.R | GTCAGCAGCCGGTTACCA | |
| Tgfb2.F | AGGAGTGGCTTCACCACAAAGACA | Zhang, M. et al., *J. Am. Coll. Cardiol.* 56, 2021-30 (2010) |
| Tgfb2.R | ATTAGACGGCACGAAGGTACAGCA | |
| Tgfbr1.F | CATTCACCACCGTGTGCCAAATGA | Gore, A.J., et al., *Reprod. Biol Endocrinol.* 3:73 (2005) |
| Tgfbr1.R | ACCTGATCCAGACCCTGATGTTGT | |
| Tgfbr2.F | TCCCAAGTCGGATGTGGAAATGGA | Gore, A.J., et al., *Reprod. Biol Endocrinol.* 3:73 (2005) |
| Tgfbr2.R | TCGCTGGCCATGACATCACTGTTA | |
| Nppa.F | TTCTTCCTCGTCTTGGCCTTT | Matsumoto, E. et al., *Genes to Cells* 18, 544-53 (2013) |
| Nppa.R | GACCTCATCTTCTACCGGCATCT | |
| Myh6.F | GCCCAGTACCTCCGAAAGTC | http://pga.mgh.harvard.edu/primerbank/ (ID: 6754774a1) |
| Myh6.R | GCCTTAACATACTCCTCCTTGTC | |
| TnnT2.F | CAGAGGAGGCCAACGTAGAAG | http://pga.mgh.harvard.edu/primerbank/ (ID: 6754774a1) |
| TnnT2.R | CTCCATCGGGGATCTTGGGT | |
| Myl7.F | GGCACAACGTGGCTCTTCTAA | http://pga.mgh.harvard.edu/primerbank/ (ID: 6754774a1) |
| Myl7.R | TGCAGATGATCCCATCCCTGT | |
| Actc1.F | GTATGCTTCTGGAAGAACTACA | |
| Actc1.R | GCAGTGGTGACAAAGGAGTAC | |
| Myocardin.F | CTGTGTGGAGTCCTCAGGTCAAACC | Zhao, R. et al., *Mol. Cell Biol.* 25, 2622-31 (2005) |

TABLE 5-continued qPCR primers

| Primers | Primer Sequence | Reference |
|---|---|---|
| Myocardin.R | GATGTGCTGCGGGCTCTTCAG | |
| SERCA2a.F | GGCCAGATCGCGCTACA | Ferguson, B.S. et al., Proc. Natl. Acad. Sci. U. S. A. 110, 9806-11 (2013) |
| SERCA2a.R | GGGCCAATTAGAGAGCAGGTTT | |

ChIP-Seq:

Chromatin immunoprecipitation with antibody against H3K4me2 (Abcam, Ab7766) was performed according to the Young lab protocol [Lee, T. I. et al., Cell 125, 301-313 (2006)] with modifications. Cells were cross-linked with 1/10 volume of fresh 11% Formaldehyde Solution (50 mM Hepes-KOH, pH 7.5, 100 mM NaCl, 1 mM EDTA, 0.5 mM EGTA, 11% Formaldehyde) at room temperature for 10 minutes. Then, 1/20 volume of 2.5 M glycine was added to quench formaldehyde. Cells were rinsed twice with 5 ml 1×PBS for each. Cells were harvested with a silicon scraper. Cells were centrifuged at 1,350×g for 5 minutes at 4° C. The Cell pellet was re-suspended in PBS with 10 ml per $10^8$ cells. Cells were centrifuged at 1,350×g for 5 minutes at 4° C. The cell pellet was quickly frozen in liquid nitrogen and stored at −80° C.

The cell pellet with $10^8$ cells was re-suspended in 5 ml of Lysis Buffer 1 (50 mM Hepes-KOH, pH 7.5, 140 mMNaCl, 1 mM EDTA, 10% glycerol, 0.5% NP-40, 0.25% Triton X-100, protease inhibitors (Roche)). Cells were rocked at 4° C. for 10 mins, and harvested by a centrifuge at 1,350×g for 5 minutes at 4° C. The cell pellet was re-suspended in in 5 ml of Lysis Buffer 2 (10 mM Tris-HCl, pH 8.0, 200 mM NaCl, 1 mM EDTA, 0.5 mM EGTA, protease inhibitors (Roche)). Cells were gently rocked at room temperature for 10 min, and then centrifuged at 1,350×g for 5 minutes at 4° C. The pellet was resuspended in 3 ml of Lysis Buffer 3 (10 mM Tris-HCl, pH 8.0, 100 mM NaCl, 1 mM EDTA, 0.5 mM EGTA, 0.1% Na-Deoxycholate, 0.5% N-lauroylsarcosine, protease inhibitors (Roche)). Cell suspension was sonicated with a microtip attached to FB-120 sonicator (Fisher) to produce DNA fragments ranging from 100 bp to 600 bp. Samples should be kept in an ice water bath during sonication. Cell suspension was centrifuged at 20,000×g for 10 minutes at 4° C. Supernatants were harvested for immuno-precipitation. Ten microliter of supernatants was used as an input control for deep sequencing.

Sonicated DNA was incubated with 20 μl magnetic bead (Thermo Scientific, 26162) and 8 μl antibody against H3K4me2 (Abcam, Ab7766) at 4° C. overnight. Complex of beads-antibody-DNA was collected by a MagneSphere® Technology Magnetic Separation Stand (Promega, Z5342), and then washed in 1 ml Wash Buffer-RIPA (50 mM Hepes-KOH, pH 7.6, 500 mM LiCl, 1 mM EDTA, 1% NP-40, 0.7% Na-Deoxycholate) three to seven times. The complexes were washed once with 1 ml TE containing 50 mM NaCl, and harvested by centrifuge at 960×g for 3 minutes at 4° C. The complexes were incubated with 210 μl of elution buffer (50 mM Tris-HCl, pH 8.0, 10 mM EDTA, 1% SDS) at 65° C. for 15 mins. The sample was centrifuged at 16,000×g for 1 minute at room temperature. Supernatant was transferred to a new tube. DNA-protein crosslink was reversed by incubating at 65° C. overnight. DNA was purified using MinElute PCR Purification Kit (QIAGEN, 28004). ChIP-seq library preparation and deep sequencing were performed at Genomics and Microarray Core at University of Colorado-Auschutz Medical Campus. Illumina HiSeq fastq files were processed to trim off 3-prime end low quality bases, mapped to the mm9 genome with the Genomic Short-read Nucleotide Alignment Program v2012-17-20 (GSNAP) and the resulting SAM files converted to sorted, indexed BAM files with SAMtools v0.1.19-44428cd. [Wu, T. D. & Nacu, S., Bioinformatics 26:873-881 (2010); Li, H. et al., Bioinformatics 25, 2078-9 (2009)] The BAM files were analyzed by PhantomPeaks v2.0. [Kharchenko, P. K., et al., Nat. Biotechnol. 26, 1351-9 (2008)] Peaks were called using the Hypergeometric Optimization of Motif EnRichment suite v4.7 (HOMER) by the findPeaks command using input DNA as the background with the following options: size 1000, minDist 2500 and fraglength equal to the DNA fragmentation length determined by Phantom-Peaks (ranging from 250-297). Differential peaks were determined using the getDifferentialPeaks HOMER command with the default settings and all peaks were annotated using the HOMER annotatePeaks.pl program against mm9. Peak shifts were calculated using the HOMER mergePeaks command with the -venn and -prefix options. ChIP-seq peaks were visualized by uploading bedGraph files, generated using the HOMER makeUCSCfile command, into the UCSC genome browser [Kent, et al., Genome Res. 12, 996-1006 (2002)] as custom tracks.

Recombinant Peptide and Small Molecules:

Cells were treated with the following compounds: A 83-01 (R&D Systems-Tocris 2939), Y27632 (Enzo life science ALX-270-333-M005), Recombinant Mouse TGF-beta 1 (R&D Systems 7666-MB-005), GW788388 (Sigma-SML0116-5 mg), LY-364947 (Sigma-L6293-5MG), SD-208 (Sigma-S7071-5MG), Thiazovivin (Sigma-SML1045-5 mg), SR-3677 (Sigma-SML0774-5 mg).

Western Blot:

Samples were placed on ice and washed with ice-cold DPBS (Gibco) twice, then ice-cold lysis buffer (150 mM NaCl, 50 mM Tris-Cl pH7.4, 1 mM EDTA, 1% Triton, Complete mini tablet (Roche), 1 mM PMSF freshly added before use) was added to the cells. Cells were scraped and transferred to a pre-chilled 1.5 Eppendorf tube and frozen in liquid N2. Before used, the lysate was thawed on ice. The lysate was passed carefully through a 25 g needle for 5 times and then centrifuge at 14,000 rpm for 15 minutes at 4° C. The supernatant was transferred to a new 1.5 ml tube. The protein concentration was measured and 20 ug of lysate for each sample was loaded to SDSPAGE. Proteins were then transferred to PVDF. The PDVF membrane was blocked in 2.5% BSA in 1×TBST for 30 mins at room temperature (RT). The primary antibody was added in blocking buffer for 60 mins at RT. Wash in 1×TBST (20 mM Tris-Cl, pH7.4; 150 mM NaCl; 0.1% Tween20) three times at RT, each for 15 mins. The Secondary antibody was added in blocking buffer for 45 mins at RT. The membrane was washed in 1×TBST for 15 mins, 1×TBST for 5 mins, then TBS (10 mM Tris-Cl pH8, 150 mM NaCl) for 5 mins. The membrane was resolved with Super Signal® West Pico (34080) or Femto (34095) substrate (Thermo Scientfic). The primary antibodies include: Snail (Cell Signaling, 3879S, 1:1000), Slug (Cell Signaling, 9585S, 1:1000), P-Smad2 (Cell Signaling, 23108P, 1:1000), Smad2 (Cell Signaling, 5339, 1:1000), αSMA (Santa Cruz, SC-32251, 1:10000), cTnI (Phospho Solutions, 2010-TNI, 1:1000), cTnT (Sigma, T6277, 1:1000), and GAPDH (Ambion, AM4300). The secondary antibodies include: Goat Anti-Mouse IgG (H+L) (Southern Biotech, 1031-05, 1:2000), Goat Anti-Rabbit IgG (Life Technologies, 65-6120, 1:2000). For separation of α- and β-myosin heavy chain, samples were run by modified 6% SDS-PAGE (separating acrylamide/bis ratio 1:100; resolving gel buffer pH 9.0; running gel buffer pH 8.2; β-mercaptoethanol 600 µl/l inner gel buffer). Gels were run overnight at 4° C. and stained with BioSafe Coomassie Blue protein stain.

Immunocytochemistry:

Cells were fixed in 2% PFA for 15 min on ice then washed with DPBS (Gibco) three times at RT. The cells were permeabilized in 0.5% Triton X-100 (made in PBS) for 20 min at RT. After washing the cells with DPBS (Gibco), cells were incubated with the primary antibody against α-actinin (Sigma A7811, 1:300), Connexin 43 (Sigma, C6219, 1:500), Troponin T (Thermo Scientific MS-245-P, 1:500), α-SMA (Santa Cruz Biotechnology, SC-32251, 1:800), Myl2 (Proteintech, 10906-1-AP, 1:200), or Myl7 (Proteintech, 17283-1-AP, 1:200) in 10% FBS(Gemini) in DPBS for 1 hour at RT. Cells were wash with DPBS three times, 5 min each. Cell were incubated with the secondary antibody (Alexa Fluor 555 Molecular Probes A21422, 1:1000) and Hoechst (Molecular Probes 33342, 1:5000) for 30 mins at RT.

Counting of Beating Cells:

Cells in 60 mm dishes were examined under an EVOS® FL Color imaging system (Life Technologies) at 25° C. Beating cells were counted at a field with an area of 0.89 mm². Ten to fifteen fields in each dish were randomly chosen.

Recording Videos of Beating Cells:

Beating cells were visualized on an inverted microscope (Nikon Diaphot 300), and videos were obtained using a CCD camera (Point Grey Research, Flea 2) at 250 C.

Recording of Spontaneous and Provoked Action Potentials:

Fragments of glass coverslips plated with iCMs at day 9 were transferred to a recording chamber (200 µl) on the stage of an inverted microscope. Cells were constantly perfused (1-2 mL/minute) with normal Tyrode's solution at 35±1° C. (in mM, 140 NaCl, 5.4 KCl, 1.2 KH2PO4, 5 HEPES, 5.55 glucose, 1 MgCl2, 1.8 CaCl2; pH adjusted to 7.4 with NaOH). Spontaneous action potentials were recorded from spontaneously beating cells in the amphotericin perforated-patch configuration in current-clamp mode (Axopatch 200B, Molecular Devices). Provoked action potentials were elicited by 200 pA, 20 ms current injections at a frequency of 1 Hz, and recorded from spontaneously beating cells. The pipette solution contained (in mM) 135 KCl, 0.1 CaCl2, 1 MgCl2, 5 NaCl, 10 EGTA, 4 Mg-ATP, and 10 HEPES, with pH adjusted to 7.2 with KOH and Amphotericin-B (Fisher Scientific, BP928) added at a final concentration of 100 µg/mL.

Nucleic Acid Delivery

In certain embodiments, expression cassettes are employed to express a transcription factor product, either for subsequent purification and delivery to a cell/subject, or for use directly in a genetic-based delivery approach. Expression requires that appropriate signals be provided in the vectors, and include various regulatory elements, such as enhancers/promoters from both viral and mammalian sources that drive expression of the genes of interest in cells. Elements designed to optimize messenger RNA stability and translatability in host cells also are contemplated.

The term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter as used herein refers to a group of transcriptional control modules that are clustered around the initiation site for RNA polymerase II. Viral promoters were some of the first to be studied, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. One such example is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promoters such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Of particular interest are muscle specific promoters, and more particularly, cardiac specific promoters. These include the myosin light chain-2 promoter (Franz et al., 1994; Kelly et al., 1995), the α-actin promoter (Moss et al., 1996), the troponin 1 promoter (Bhaysar et al., 1996); the Na+/Ca2+ exchanger promoter (Barnes et al., 1997), the dystrophin promoter (Kimura et al., 1997), the α7 integrin promoter (Ziober and Kramer, 1996), the brain natriuretic peptide promoter (LaPointe et al., 1996) and the aB-crystallin/small heat shock protein promoter (Gopal-Srivastava, 1995), α-myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine 2000™ is widely used and commercially available.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Methods of Treating Myocardial Infarction (MI)

The present invention provides for new post-MI therapies. In one embodiment of the present invention, methods for the treatment of subjects following an MI provides for one or more of the following outcomes as compared to an untreated patient: increased exercise capacity, increased blood ejection volume, decreased left ventricular end diastolic pressure, decreased pulmonary capillary wedge pressure, increased cardiac output, improved cardiac index, decreased pulmonary artery pressures, decreased left ventricular end systolic and diastolic dimensions, and decreased left ventricular wall stress, decreased wall tension and decreased wall thickness-same for right ventricle. In addition, the treatment may prevent progression to cardiac hypertrophy and ultimately heart failure.

Treatment regimens would vary depending on the clinical situation. However, in general, the treatment would begin at a time following an MI when the patient has been stabilized, but before significant cardiac fibroblast mobilization and scarring has begun. The patient may or may not be undergoing one or more other therapies for either prevention or treatment of an MI, or prevention or treatment of MI-related sequelae. This would mean initiating a treatment within about 24, 36, 38, 72, 96 hours of an MI, or within about 5, 6, 7, 8, 9 or 10 days of an MI. The therapy may continue for as long as cardiac fibroblasts would be active within the ischemic zone, such as up to 7 days, 14 days, 21 days, 28 days, 1 month, 2 months, 3 months or longer.

Glossary of Claim Terms

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" whereever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of converting a fibroblast into a cardiomyocyte comprising the step of delivering to the fibroblast a combination of reprogramming factors comprising GATA4, Hand2, MEF2C, Tbx5, miR-1, and miR-133.

2. The method according to claim 1 further comprising delivering to the fibroblast the small molecule A83-01.

3. A method of converting a fibroblast into a cardiomyocyte comprising the step of contacting the fibroblast with Y27632, the reprogramming factors miR-1, miR-133, GATA4, Hand2, MEF2C, and Tbx5 and the small molecule A83-01.

4. A method of treating myocardial infarction in a subject comprising delivering to the heart of the subject reprogramming factors GATA4, Hand2, MEF2C, Tbx5, miR-1, and miR-133 expression cassettes in combination with a molecule that inhibits TGF-β signaling or a small molecule that targets RhoA-ROCK signaling.

5. The method according to claim 4 wherein the small molecule that targets RhoA-ROCK signaling is delivered to heart of the subject and the small molecule is selected from the group consisting of Y-27632, GW788388, Thiazovivin and SR-3677.

6. The method according to claim 4 wherein the small molecule that inhibits TGF-β signaling is delivered to heart of the subject and the small molecule is selected from the group consisting of A 83-01, LY-364947, SD-208 and GW788388.

7. The method according to claim 4 wherein the expression cassettes are comprised in replicable vectors.

8. A method of converting a fibroblast into a cardiomyocyte comprising the step of delivering to the fibroblast the small molecule A83-01 and a combination of reprogramming factors comprising GATA4, Hand2, MEF2C, Tbx5, and miR-133.

9. A method of converting a fibroblast into a cardiomyocyte comprising the step of delivering to the fibroblast the small molecule A83-01 and a combination of reprogramming factors comprising GATA4, Hand2, MEF2C, Tbx5, and miR-1.

10. A method of converting a fibroblast into a cardiomyocyte comprising the step of delivering to the fibroblast a small molecule that targets RhoA-ROCK signaling, reprogramming factors miR-1 or miR-133, and a combination of reprogramming factors GATA4, Hand2, MEF2C, and Tbx5.

11. The method according to claim 10 wherein the small molecule that targets RhoA-ROCK signaling is a ROCK inhibitor selected from the group consisting of Y-27632, GW788388, Thiazovivin and SR-3677.

12. A method of converting a fibroblast into a cardiomyocyte comprising the step of delivering to the fibroblast a small molecule that targets TGF-β signaling, reprogramming factors miR-1 or miR-133, and a combination of reprogramming factors GATA4, Hand2, MEF2C, and Tbx5.

13. The method according to claim 12 wherein the small molecule that targets TGF-β signaling is a TGF-β inhibitor selected from the group consisting of A 83-01, LY-364947, SD-208 and GW788388.

* * * * *